United States Patent
Norizuki et al.

(10) Patent No.: US 10,732,333 B2
(45) Date of Patent: Aug. 4, 2020

(54) INFRARED SENSOR, NEAR-INFRARED RAY ABSORPTION COMPOSITION, PHOTOSENSITIVE RESIN COMPOSITION, COMPOUND, NEAR-INFRARED RAY ABSORPTION FILTER, AND IMAGE PICK-UP DEVICE

(71) Applicant: FUJIFILM Corporation, Tokyo (JP)

(72) Inventors: Yutaro Norizuki, Haibara-gun (JP); Takashi Katoh, Haibara-gun (JP); Satoru Murayama, Haibara-gun (JP); Yoshihiro Jimbo, Haibara-gun (JP); Daisuke Sasaki, Haibara-gun (JP); Keisuke Arimura, Haibara-gun (JP); Takuya Tsuruta, Haibara-gun (JP)

(73) Assignee: FUJIFILM Corporation, Tokyo (JP)

( * ) Notice: Subject to any disclaimer, the term of this patent is extended or adjusted under 35 U.S.C. 154(b) by 401 days.

(21) Appl. No.: 15/297,230

(22) Filed: Oct. 19, 2016

(65) Prior Publication Data
US 2017/0038507 A1 Feb. 9, 2017

Related U.S. Application Data

(63) Continuation of application No. PCT/JP2015/062345, filed on Apr. 23, 2015.

(30) Foreign Application Priority Data

May 1, 2014 (JP) ................ 2014-094647
Feb. 20, 2015 (JP) ................ 2015-031681

(51) Int. Cl.
| C09K 3/00 | (2006.01) |
| G02B 5/20 | (2006.01) |
| C07F 5/02 | (2006.01) |
| C09B 23/00 | (2006.01) |
| G02B 5/22 | (2006.01) |
| C09B 57/10 | (2006.01) |
| C09B 57/00 | (2006.01) |
| G02B 5/28 | (2006.01) |
| C07D 487/04 | (2006.01) |
| C09B 69/10 | (2006.01) |
| H04N 5/33 | (2006.01) |
| G02B 1/04 | (2006.01) |

(52) U.S. Cl.
CPC .......... *G02B 5/208* (2013.01); *C07D 487/04* (2013.01); *C07F 5/02* (2013.01); *C09B 23/00* (2013.01); *C09B 57/00* (2013.01); *C09B 57/10* (2013.01); *C09B 69/105* (2013.01); *G02B 5/201* (2013.01); *G02B 5/223* (2013.01); *G02B 5/281* (2013.01); *H04N 5/33* (2013.01); *G02B 1/04* (2013.01)

(58) Field of Classification Search
USPC ......................................................... 257/40
See application file for complete search history.

(56) References Cited

U.S. PATENT DOCUMENTS

| 5,973,158 A | 10/1999 | Usami et al. |
| 9,150,670 B2 | 10/2015 | Kato et al. |
| 2011/0070407 A1 | 3/2011 | Kato et al. |
| 2013/0126849 A1* | 5/2013 | Arakane ............... C09K 11/06 257/40 |

FOREIGN PATENT DOCUMENTS

| JP | 10-105076 A | 4/1998 |
| JP | 10-231435 A | 9/1998 |
| JP | 2007-163644 A | 6/2007 |
| JP | 2008-091535 A | 4/2008 |
| JP | 2009-092784 A | 4/2009 |
| JP | WO2010041769 | * 1/2010 |
| JP | WO2010/041769 | * 4/2010 |
| JP | 2010-222557 A | 10/2010 |
| JP | 2011-068731 A | 4/2011 |
| JP | 2012-007038 A | 1/2012 |
| JP | 2013-037212 A | 2/2013 |
| WO | 2010/041769 A1 | 4/2010 |

OTHER PUBLICATIONS

International Preliminary Report on Patentability, dated Nov. 10, 2016, from the International Bureau in counterpart International Application No. PCT/JP2015/062345.
Office Action dated Oct. 18, 2017 from the Korean Intellectual Property Office in counterpart Korean Application No. 10-2016-7029943.
International Search Report of PCT/JP2015/062345 dated Jul. 14, 2015 [PCT/ISA/210].
Written Opinion of PCT/JP2015/062345 dated Jul. 14, 2015 [PCT/ISA/237].
Office Action dated Sep. 12, 2018, from the Taiwanese Intellectual Property Office in counterpart Taiwanese Application No. 104113623.
Office Action dated Sep. 26, 2017 from the Japanese Patent Office in counterpart Japanese Application No. 2016-516348.

(Continued)

*Primary Examiner* — Monique R Peets
(74) *Attorney, Agent, or Firm* — Sughrue Mion, PLLC

(57) ABSTRACT

The present invention relates to an infrared sensor, a near-infrared ray absorption composition, a photosensitive resin composition, a compound, a near-infrared ray absorption filter, and an image pick-up device. Provided is an infrared sensor 100 that detects an object by detecting light in wavelengths of 900 nm to 1,000 nm, including infrared ray transmission filters 113 and near-infrared ray absorption filters 111, in which the near-infrared ray absorption filters 111 contains a near-infrared ray absorption substance having a maximum absorption wavelength in wavelengths of 900 nm to 1,000 nm.

5 Claims, 3 Drawing Sheets

(56) References Cited

OTHER PUBLICATIONS

Office Action dated Jul. 13, 2018, issued by the State Intellectual Property Office of the P.R.C. in corresponding Chinese Application No. 201580023788.0.
Office Action dated Mar. 11, 2019, issued by the State Intellectual Property Office of the P.R.C. in corresponding Chinese Application No. 201580023788.0.

* cited by examiner

INFRARED SENSOR, NEAR-INFRARED RAY ABSORPTION COMPOSITION, PHOTOSENSITIVE RESIN COMPOSITION, COMPOUND, NEAR-INFRARED RAY ABSORPTION FILTER, AND IMAGE PICK-UP DEVICE

CROSS-REFERENCE TO RELATED APPLICATIONS

This application is a Continuation of PCT International Application No. PCT/JP2015/062345 filed on Apr. 23, 2015, which claims priority under 35 U.S.C. § 119(a) to Japanese Patent Application No. 2014-094647 filed on May 1, 2014 and Japanese Patent Application No. 2015-031681 filed on Feb. 20, 2015. Each of the above application(s) is hereby expressly incorporated by reference, in its entirety, into the present application.

BACKGROUND OF THE INVENTION

1. Field of the Invention

The present invention relates to an infrared sensor, a near-infrared ray absorption composition, a photosensitive resin composition, a compound, a near-infrared ray absorption filter, and an image pick-up device.

2. Description of the Related Art

In a video camera, a digital still camera, or a cellular phone with a camera function, a charge coupled device (CCD) or a complementary metal-oxide-semiconductor (CMOS) which is a solid-state imaging device for a color image is used. In such a solid-state imaging device, a silicon photodiode having sensitivity to a near infrared ray in a light receiving section thereof is used. Therefore, visibility correction is required and near-infrared ray absorption filters are used in many cases.

As a compound having a near-infrared ray absorption function, a pyrrolopyrrole coloring agent or the like is known (for example, JP2010-222557A and JP2011-68731A).

SUMMARY OF THE INVENTION

The use of solid-state imaging devices for various purposes has been reviewed.

Since near infrared rays have a longer wavelength than visible light, near infrared rays hardly scatter and can be used for distance measurement or three-dimensional measurement. Near infrared rays are not observed by the eyes of humans, animals, or the like, and thus can be used in photographing a subject at night without irritating the subject, for the use of photographing a nocturnal wild animal or for security use, without being noticed by the subject even if the subject is illuminated by a light source of near infrared rays.

In this manner, the use of such a solid-state imaging device in an infrared sensor that detects an object by detecting near infrared rays has been reviewed.

An object of the invention is to provide an infrared sensor having excellent detectability and an excellent image quality, a near-infrared ray absorption composition, a photosensitive resin composition, a compound, a near-infrared ray absorption filter, and an image pick-up device.

Under these circumstances, the present inventors have diligently conducted research to find that the above object can be achieved by using a near-infrared ray absorption substance having a maximum absorption wavelength in a specific wavelength range in an infrared sensor, so as to complete the invention.

Specifically, the above objects are solved by the means <1>, preferably by means <2> to <17>.

<1> An infrared sensor that detects an object by detecting light in wavelengths of 900 nm to 1,000 nm, comprising: an infrared ray transmission filter; and a near-infrared ray absorption filter, in which the near-infrared ray absorption filter contains a near-infrared ray absorption substance having a maximum absorption wavelength in wavelengths of 900 nm to 1,000 nm.

<2> The infrared sensor according to <1>, in which the near-infrared ray absorption substance is a compound represented by Formula (1) below,

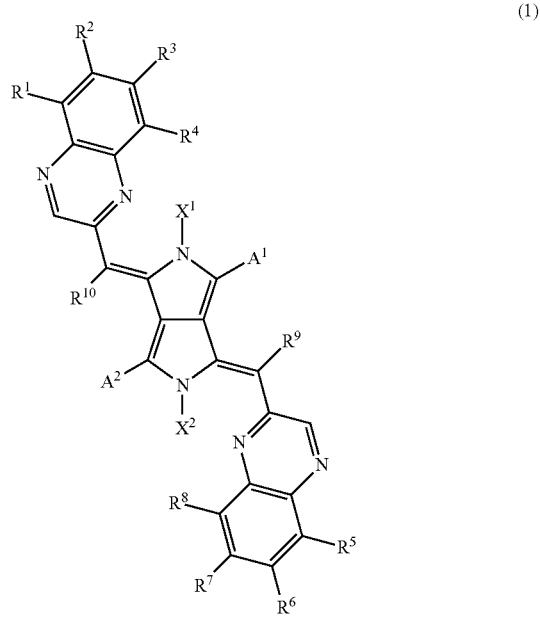

in Formula (1), $X^1$ and $X^2$ each independently represent a hydrogen atom or a substituent, $A^1$ and $A^2$ each independently represent a substituent, $R^1$ to $R^{10}$ each independently represent a hydrogen atom or a substituent, and at least one of $R^1$, $R^2$, $R^3$, $R^4$, $R^5$, $R^6$, $R^7$, and $R^8$ represents a substituent.

<3> The infrared sensor according to <2>, in which in Formula (1) above, at least one of $R^1$, $R^2$, $R^3$, $R^4$, $R^5$, $R^6$, $R^7$, and $R^8$ is a halogen atom, an alkyl group, an alkoxy group, an aryl group, a cyano group, or a group represented by $-L^{100}-X^{100}$, and in which $L^{100}$ represents a single bond or a divalent linking group, and $X^{100}$ represents a reactive group.

<4> The infrared sensor according to <2> or <3>, in which, in Formula (1) above, at least one of $R^1$, $R^2$, $R^3$, $R^4$, $R^5$, $R^6$, $R^7$, and $R^8$ is a halogen atom or a group represented by $-L^{100}-X^{100}$, and in which $L^{100}$ represents a single bond or a divalent linking group, and $X^{100}$ represents a reactive group.

<5> The infrared sensor according to any one of <2> to <4>, in which, in Formula (1) above, at least one of $R^1$, $R^2$, $R^3$, and $R^4$ is a halogen atom or a group represented by $-L^{100}-X^{100}$, and at least one of $R^5$, $R^6$, $R^7$, and $R^8$ is a halogen atom or a group represented by $-L^{100}-X^{100}$, and in which $L^{100}$ represents a single bond or a divalent linking group, and $X^{100}$ represents a reactive group.

<6> The infrared sensor according to any one of <3> to <5>, in which the halogen atom is a chlorine atom.

<7> The infrared sensor according to any one of <2> to <6>, in which, in Formula (1) above, $A^1$ and $A^2$ each independently represent an aryl group or a heteroaryl group, and $R^9$ and $R^{10}$ each independently represent an electron-withdrawing group.

<8> The infrared sensor according to any one of <2> to <7>, in which, in Formula (1) above, $R^9$ and $R^{10}$ are cyano groups.

<9> The infrared sensor according to any one of <2> to <8>, in which in Formula (1) above, $X^1$ and $X^2$ each independently represent a hydrogen atom or a group represented by Formula (2) below,

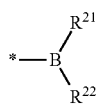

(2)

in Formula (2), $R^{21}$ and $R^{22}$ each independently represent a substituent, $R^{21}$ and $R^{22}$ may be bonded to each other to form a ring and * represents an atomic bond.

<10> A near-infrared ray absorption composition used for forming a near-infrared ray absorption filter of an infrared sensor that detects an object by detecting light in wavelengths of 900 nm to 1,000 nm, comprising: a near-infrared ray absorption substance having a maximum absorption wavelength in wavelengths of 900 nm to 1,000 nm.

<11> A photosensitive resin composition comprising: a compound represented by Formula (1) below,

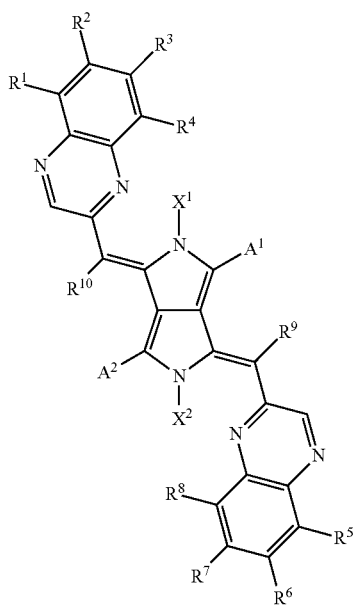

(1)

in Formula (1), $X^1$ and $X^2$ each independently represent a hydrogen atom or a substituent, $A^1$ and $A^2$ each independently represent a substituent, $R^1$ to $R^{10}$ each independently represent a hydrogen atom or a substituent, and at least one of $R^1$, $R^2$, $R^3$, $R^4$, $R^5$, $R^6$, $R^7$, and $R^8$ is a substituent.

<12> The photosensitive resin composition according to <11> further comprising: a curable compound.

<13> A compound represented by Formula (1) below,

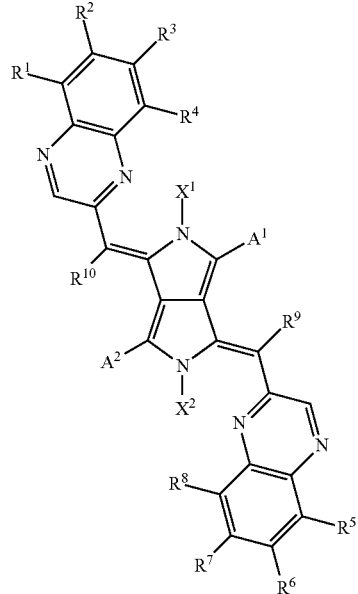

(1)

in Formula (1), $X^1$ and $X^2$ each independently represent a hydrogen atom or a substituent, $A^1$ and $A^2$ each independently represent a substituent, $R^1$ to $R^{10}$ each independently represent a hydrogen atom or a substituent, and at least one of $R^1$, $R^2$, $R^3$, $R^4$, $R^5$, $R^6$, $R^7$, and $R^8$ represents a substituent.

<14> The compound according to <13>, in which, in Formula (1) above, at least one of $R^1$, $R^2$, $R^3$, and $R^4$ is a halogen atom or a group represented by -$L^{100}$-$X^{100}$, and at least one of $R^5$, $R^6$, $R^7$, and $R^8$ is a halogen atom or a group represented by -$L^{100}$-$X^{100}$, and in which $L^{100}$ represents a single bond or a divalent linking group, and $X^{100}$ represents a reactive group.

<15> The compound according to <14>, in which the halogen atom represented by $R^1$ to $R^8$ is a chlorine atom.

<16> A near-infrared ray absorption filter obtained by hardening the photosensitive resin composition according to <11> or <12>.

<17> An image pick-up device comprising: the infrared sensor according to <1>.

According to the invention, it is possible to provide an infrared sensor having excellent detectability and an excellent image quality. It is possible to provide a near-infrared ray absorption composition, a photosensitive resin composition, a compound, a near-infrared ray absorption filter, and an image pick-up device.

DESCRIPTION OF THE PREFERRED EMBODIMENTS

Figure 1:
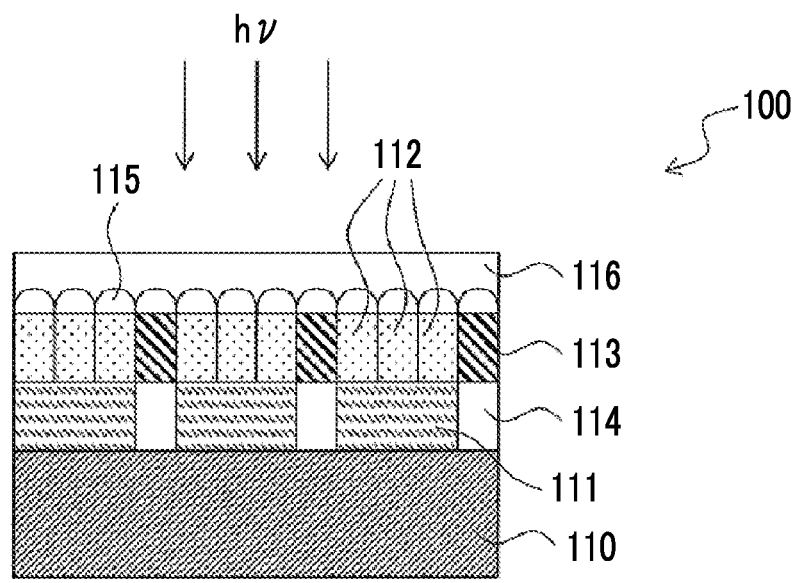
FIG. 1 is a cross-sectional view schematically illustrating a configuration according to an embodiment of an infrared sensor of the invention.

Hereinafter, the content of the invention is described in detail.

In this specification, the expression "to" is used in a meaning of including numerical values indicated before and after the expression as a lower limit and an upper limit.

In the description of a group (atomic group) in this specification, a denotation without substitution and unsubstitution include a group (atomic group) with a substituent, together with a group (atomic group) without a substituent. For example, an "alkyl group" includes not only an alkyl group (unsubstituted alkyl group) without a substituent but also an alkyl group (substituted alkyl group) with a substituent.

In this specification, "(meth)acrylate" represents acrylate and methacrylate, "(meth)acryl" represents acryl and methacryl, "(meth)allyl" represents allyl and methallyl, and "(meth)acryloyl" represents acryloyl and methacryloyl.

The monomer is differentiated from an oligomer and a polymer, and refers to a compound having a weight-average molecular weight of 2,000 or less.

In this specification, a polymerizable compound refers to a compound having a polymerizable functional group. A polymerizable compound may be a monomer or may be a polymer. The polymerizable functional group refers to a group participating in polymerization reaction.

A method for measuring a weight-average molecular weight and a number-average molecular weight of a compound used in the invention can be measured by gel permeation chromatography (GPC), and defined as a value in terms of polystyrene by GPC measurement. For example, a weight-average molecular weight and a number-average molecular weight can be obtained by using HLC-8220 (manufactured by Tosoh Corporation), using TSK gel Super AWM-H (manufactured by Tosoh Corporation, 6.0 mm ID×15.0 cm) as a column and using 10 mmol/L lithium bromide NMP (N-methylpyrrolidinone) solution as an eluent.

A near infrared ray refers to light having a maximum absorption wavelength range of 700 to 2,500 nm (electromagnetic wave).

In this specification, a total solid content refers to total mass of a content except for a solvent from the entire content of a composition. A solid content according to the invention is a solid content at 25° C.

<Near-Infrared Ray Absorption Composition>

The near-infrared ray absorption composition according to the invention contains the near-infrared ray absorption substance having a maximum absorption wavelength at wavelengths of 900 nm to 1,000 nm.

The expression "having a maximum absorption wavelength at wavelengths of 900 nm to 1,000 nm" means to have a wavelength exhibiting maximum absorbance in the wavelength range of 900 nm to 1,000 nm in an absorption spectrum.

The near-infrared ray absorption substance according to the invention preferably has a maximum absorption wavelength in wavelengths of 905 nm to 995 nm and more preferably has a maximum absorption wavelength in wavelengths of 910 nm to 990 nm.

As a near-infrared ray absorption substance having a maximum absorption wavelength at wavelengths of 900 nm to 1,000 nm, a compound is preferable, a pyrrolopyrrole compound is more preferable, a quinoxaline-type pyrrolopyrrole compound is even more preferable, and a compound represented by Formula (1) below is particularly preferable. A compound represented by Formula (1) below has a maximum absorption wavelength on a long wavelength side and has excellent light fastness. It is assumed that the reason for having such characteristics that monomers are obliquely deviated and are easily overlapped with each other by introducing a substituent to a quinoxaline part such that J-aggregation is improved and thus an absorption wavelength is shifted to a longer wavelength side. Specific reasons are not clear, but light fastness was improved by introducing a substituent to a quinoxaline part.

Hereinafter, a compound represented by Formula (1) is described.

<<Compound Represented by Formula (1)>>

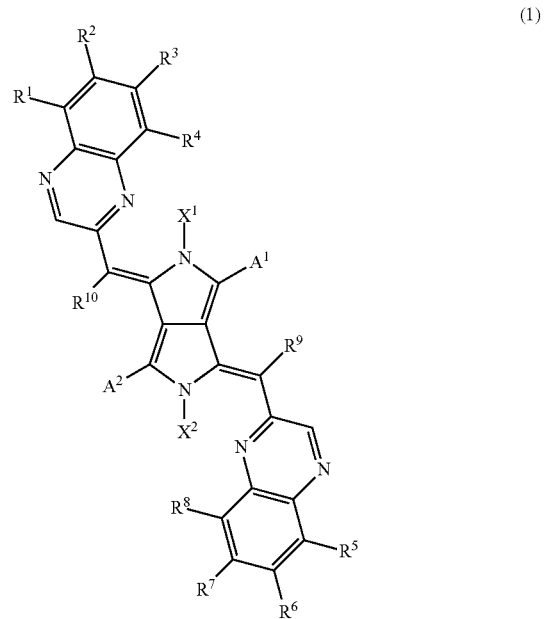

(1)

In Formula (1), $X^1$ and $X^2$ each independently represent a hydrogen atom or a substituent, $A^1$ and $A^2$ each independently represent a substituent, $R^1$ to $R^{10}$ each independently represent a hydrogen atom, or a substituent, and at least one of $R^1$, $R^2$, $R^3$, $R^4$, $R^5$, $R^6$, $R^7$, or $R^8$ represents a substituent.

Examples of the substituent represented by $A^1$ and $A^2$ include an aryl group and a heteroaryl group.

As an aryl group, an aryl group having 6 to 20 carbon atoms is preferable, and an aryl group having 6 to 12 carbon atoms is more preferable. Phenyl or naphthyl is particularly preferable.

The heteroaryl group may be a monocyclic ring or may be a polycyclic ring. The number of hetero atoms configuring a heteroaryl group is preferably 1 to 3. A hetero atom configuring a heteroaryl group is preferably a nitrogen atom, an oxygen atom, or a sulfur atom. The number of carbon atoms of a heteroaryl group is preferably 3 to 30, more preferably 3 to 18, and further preferably 3 to 12. Specific examples of a heteroaryl group include imidazolyl, pyridyl, quinolyl, furyl, thienyl, benzoxazolyl, benzimidazolyl, benzothiazolyl, naphthothiazolyl, m-carbazolyl, and azepinyl.

The aryl group and the heteroaryl group described above may have substituents or may be unsubstituted. In view of improving solubility to a solvent, an aryl group and a heteroaryl group preferably have substituents. Examples of the substituent include an alkyl group, an alkenyl group, an alkoxy group, and a group represented by -L-$R^{x1}$ described below, and a group represented by -$L^{100}$-$X^{100}$ described below.

The number of carbon atoms of the alkyl group is preferably 1 to 40, more preferably 1 to 30, and particularly preferably 1 to 25. An alkyl group may have any one of a linear shape, a branched shape, or a cyclic shape, but a linear shape or a branched shape is preferable, and a branched shape is particularly preferable.

The number of carbon atoms of the alkenyl group is preferably 2 to 40. For example, the lower limit thereof is more preferably 3 or greater, even more preferably 5 or greater, still even more preferably 8 or greater, and particularly preferably 10 or greater. The upper limit thereof is more preferably 35 or less and even more preferably 30 or less. The alkenyl group may have any one of a linear shape, a branched shape, or a cyclic shape, but a linear shape or a branched shape is preferable, and a branched shape is particularly preferable.

The number of carbon atoms of the alkoxy group is preferably 1 to 40, more preferably 1 to 30, and particularly preferably 1 to 25. The alkoxy group may have any one of a linear shape, a branched shape, or a cyclic shape, but a linear shape or a branched shape is preferable, and a branched shape is particularly preferable.

In a group represented by -L-$R^{x1}$, L represents a group obtained by —CO—, —COO—, —OCO—, —$(OR^{x2})_m$—, —$(R^{x2}O)_m$—, and a combination thereof, $R^{x1}$ represents an alkyl group, an alkenyl group, or an aryl group, $R^{x2}$ represents an alkylene group or an arylene group, m represents an integer of 2 or greater, m $R^{x2}$'s may be identical to each other or may be different from each other.

L is preferably —$(OR^{x2})_m$— or —$(R^{x2}O)_m$—.

An alkyl group, an alkenyl group, and an aryl group represented by $R^{x1}$ described above have the same meanings as an alkyl group, an alkenyl group, and an aryl group, and preferable ranges thereof are also the same. $R^{x1}$ is preferably an alkyl group or an alkenyl group, and more preferably an alkyl group. An alkyl group, an alkenyl group, and an aryl group represented by $R^{x1}$ may be unsubstituted or may have a substituent. As the substituent, substituents represented by $R^9$ and $R^{10}$ described below include a group represented by -$L^{100}$-$X^{100}$ described below.

The number of carbon atoms of the alkylene group represented by $R^{x2}$ is preferably 1 to 20, more preferably 1 to 10, and even more preferably 1 to 5. The alkylene group may have a linear shape, a branched shape, or a cyclic shape, but a linear shape or a branched shape is preferable.

The number of carbon atoms of the arylene group represented by $R^{x2}$ is preferably 6 to 20 and more preferably 6 to 12.

m represents an integer of 2 or greater, preferably 2 to 20 and more preferably 2 to 10.

In a group represented by -$L^{100}$-$X^{100}$, $L^{100}$ represents a single bond or a divalent linking group, and $X^{100}$ represents a reactive group. As the reactive group, one or more types selected from a vinyl group, a (meth)allyl group, a (meth)acryloyl group, an epoxy group, an oxetanyl group, an isocyanate group, a hydroxyl group, an amino group, a carboxyl group, a thiol group, an alkoxysilyl group, a methylol group, a sulfo group, a styryl group, and a maleimide group are preferable, and a vinyl group, a (meth)allyl group, a (meth)acryloyl group, a hydroxyl group, and a carboxyl group are more preferable. As the reactive group, at least one type represented by Formulae (A-1) to (A-3) below is preferable.

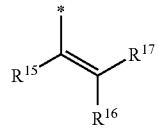

(A-1)

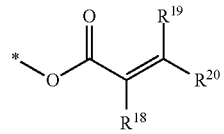

(A-2)

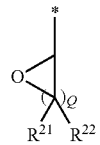

(A-3)

In Formula (A-1), $R^{15}$, $R^{16}$ and $R^{17}$ each independently represent a hydrogen atom, a linear or branched alkyl group having 1 to 18 carbon atoms, a linear or branched alkenyl group having 1 to 18 carbon atoms, a linear or branched alkynyl group having 1 to 18 carbon atoms, a cycloalkyl group having 3 to 18 carbon atoms, a cycloalkenyl group having 3 to 18 carbon atoms, a cycloalkynyl group having 3 to 18 carbon atoms or an aryl group having 6 to 18 carbon atoms.

The number of carbon atoms of the alkyl group is preferably 1 to 10, more preferably 1 to 6, further preferably 1 to 3, and particularly preferably 1.

The number of carbon atoms of the alkenyl group is preferably 1 to 10, more preferably 1 to 6, and further preferably 1 to 3.

The number of carbon atoms of the alkynyl group is preferably 1 to 10, more preferably 1 to 6, and further preferably 1 to 3.

The number of carbon atoms of the cycloalkyl group is preferably 3 to 10, more preferably 3 to 8, and further preferably 3 to 6.

The number of carbon atoms of the cycloalkenyl group is preferably 3 to 10, more preferably 3 to 8, and further preferably 3 to 6.

The number of carbon atoms of the cycloalkynyl group is preferably 3 to 10, more preferably 3 to 8, and further preferably 3 to 6.

The number of carbon atoms of the aryl group is preferably 6 to 12, more preferably 6 to 8, and further preferably 6.

In Formula (A-1), $R^{15}$ is preferably a hydrogen atom or an alkyl group having 1 to 18 carbon atoms and more preferably a hydrogen atom. In Formula (A-1), $R^{16}$ and $R^{17}$ each independently preferably represent a hydrogen atom or an alkyl group having 1 to 18 carbon atoms, and more preferably a hydrogen atom.

In Formula (A-2), $R^{18}$, $R^{19}$ and $R^{20}$ each independently represent a hydrogen atom, a methyl group, a fluorine atom, or —$CF_3$. In Formula (A-2), $R^{18}$ is preferably a methyl group. In Formula (A-2), $R^{19}$ and $R^{20}$ are preferably hydrogen atoms.

In Formula (A-3), $R^{21}$ and R each independently represent a hydrogen atom, a methyl group, a fluorine atom, or —$CF_3$, and a hydrogen atom is preferable. In Formula (A-3), Q represents 1 or 2.

In a case where $L^{100}$ represents a divalent linking group, $L^{100}$ is preferably an alkylene group having 1 to 20 carbon atoms, an arylene group having 6 to 18 carbon atoms, an heteroarylene group having 3 to 18 carbon atoms, —O—, —S—, —CO—, —COO—, —OCO—, or a combination of these groups.

$R^1$ to $R^{10}$ each independently represent a hydrogen atom or a substituent, and at least one of $R^1$, $R^2$, $R^3$, $R^4$, $R^5$, $R^6$, $R^7$, or $R^8$ represents a substituent. It is preferable that 2 to 8 items of $R^1$ to $R^8$ are substituents, 2 to 6 items are more preferably substituents, and 2 to 4 items are particularly preferably substituents.

Examples of the substituent represented by $R^1$ to $R^8$ include a halogen atom, an alkyl group, an alkoxy group, an aryl group, a cyano group, a group represented by -$L^{100}$-$X^{100}$ described above.

As the halogen atom, a fluorine atom, a chlorine atom, a bromine atom, and an iodine atom are preferable, and a chlorine atom is particularly preferable.

The number of carbon atoms of the alkyl group is preferably 1 to 40, more preferably 1 to 30, and particularly preferably 1 to 25. The alkyl group is any one of a linear shape, a branched shape, or a cyclic shape, but a linear shape or a branched shape is preferable, and a linear shape is particularly preferable.

The number of carbon atoms of the alkoxy group is preferably 1 to 40, more preferably 1 to 30, and particularly preferably 1 to 25. The alkoxy group may have any one of a linear shape, a branched shape, or a cyclic shape, but a linear shape or a branched shape is preferable, and a linear shape is particularly preferable.

The number of carbon atoms of the aryl group is preferably 6 to 20 and more preferably 6 to 12.

Substituents represented by $R^1$ to $R^8$ are preferably a halogen atom and a group represented by -$L^{100}$-$X^{100}$ described above, a halogen atom is more preferable, and a chlorine atom is particularly preferable.

It is preferable that at least one of $R^1$, $R^2$, $R^3$, or $R^4$ is a halogen atom or a group represented by -$L^{100}$-$X^{100}$, and at least one of $R^5$, $R^6$, $R^7$, or $R^8$ is a halogen atom or a group represented by -$L^{100}$-$X^{100}$.

Examples of the substituents represented by $R^9$ and $R^{10}$ include an alkyl group (preferably having 1 to 30 carbon atoms, more preferably having 1 to 20 carbon atoms, and particularly preferably having 1 to 10 carbon atoms, and examples thereof include methyl, ethyl, iso-propyl, tert-butyl, n-octyl, n-decyl, n-hexadecyl, 2-methylbutyl, 2-ethylcyclohexyl, cyclopentyl, and cyclohexyl), an alkenyl group (preferably having 2 to 30 carbon atoms, more preferably having 2 to 20 carbon atoms, and particularly preferably having 2 to 10 carbon atoms, examples thereof include vinyl, allyl, 2-butenyl, and 3-pentenyl), an alkynyl group (preferably having 2 to 30 carbon atoms, more preferably having 2 to 20 carbon atoms, and particularly preferably having 2 to 10 carbon atoms, and examples thereof include propargyl, and 3-pentynyl), an aryl group (preferably having 6 to 30 carbon atoms, more preferably having 6 to 20 carbon atoms, and particularly preferably having 6 to 12 carbon atoms, and examples thereof include phenyl, p-methylphenyl, biphenyl, naphthyl, anthranil, and phenanthryl), an amino group (preferably having 0 to 30 carbon atoms, more preferably having 0 to 20 carbon atoms, and particularly preferably having 0 to 10 carbon atoms, and including an alkylamino group, an arylamino group, and a heterocyclic amino group, and examples thereof include amino, methylamino, dimethylamino, diethylamino, dibenzylamino, diphenylamino, and ditolylamino), an alkoxy group (preferably having 1 to 30 carbon atoms, more preferably having 1 to 20 carbon atoms, and particularly preferably having 1 to 10 carbon atoms, and examples thereof include methoxy, ethoxy, butoxy, and 2-ethylhexyloxy), an aryloxy group (preferably having 6 to 30 carbon atoms, more preferably having 6 to 20 carbon atoms, and particularly preferably having 6 to 12 carbon atoms, and examples thereof include phenyloxy, 1-naphthyloxy, and 2-naphthyloxy), an aromatic heterocyclic oxy group (preferably having 1 to 30 carbon atoms, more preferably having 1 to 20 carbon atoms, and particularly preferably having 1 to 12 carbon atoms, and examples thereof include pyridyloxy, pyrazyloxy, pyrimidyloxy, and quinolyloxy), an acyl group (preferably having 1 to 30 carbon atoms, more preferably having 1 to 20 carbon atoms, particularly preferably having 1 to 12 carbon atoms, and examples thereof include acetyl, benzoyl, formyl, and pivaloyl), an alkoxycarbonyl group (preferably having 2 to 30 carbon atoms, more preferably having 2 to 20 carbon atoms, particularly preferably having 2 to 12 carbon atoms, and examples thereof include methoxycarbonyl and ethoxycarbonyl), an aryloxycarbonyl group (preferably having 7 to 30 carbon atoms, more preferably having 7 to 20 carbon atoms, and particularly preferably having 7 to 12 carbon atoms, and examples thereof include phenyloxycarbonyl), an acyloxy group (preferably having 2 to 30 carbon atoms, more preferably having 2 to 20 carbon atoms, and particularly preferably having 2 to 10 carbon atoms, and examples thereof include acetoxy and benzoyloxy), an acylamino group (preferably having 2 to 30 carbon atoms, more preferably having 2 to 20 carbon atoms, and particularly preferably having 2 to 10 carbon atoms, and examples thereof include acetylamino and benzoylamino), an alkoxycarbonylamino group (preferably having 2 to 30 carbon atoms, more preferably having 2 to 20 carbon atoms, and particularly preferably having 2 to 12 carbon atoms, and examples thereof include methoxycarbonylamino), an aryloxycarbonylamino group (preferably having 7 to 30 carbon atoms, more preferably having 7 to 20 carbon atoms, and particularly preferably having 7 to 12 carbon atoms, and examples thereof include phenyloxycarbonylamino), a sulfonylamino group (preferably having 1 to 30 carbon atoms, more preferably having 1 to 20 carbon atoms, and particularly preferably having 1 to 12 carbon atoms, and examples thereof include methanesulfonylamino, and benzenesulfonylamino), a sulfamoyl group (preferably having 0 to 30 carbon atoms, more preferably having 0 to 20 carbon atoms, particularly preferably having 0 to 12 carbon atoms, and examples thereof include sulfamoyl, methylsulfamoyl, dimethylsulfamoyl, and phenylsulfamoyl), a carbamoyl group (preferably having 1 to 30 carbon atoms, more preferably having 1 to 20 carbon atoms, and particularly preferably having 1 to 12 carbon atoms, and examples thereof include carbamoyl, methylcarbamoyl, diethylcarbamoyl, and phenylcarbamoyl), an alkylthio group (preferably having 1 to 30 carbon atoms, more preferably having 1 to 20 carbon atoms, and particularly preferably having 1 to 12 carbon atoms, and examples thereof include methylthio and ethylthio), an arylthio group (preferably having 6 to 30 carbon atoms, more preferably having 6 to 20 carbon atoms, and particularly preferably having 6 to 12 carbon atoms, and examples thereof include phenylthio), an aromatic heterocyclic thio group (preferably having 1 to 30 carbon atoms, more preferably having 1 to 20 carbon atoms, and particularly preferably having 1 to 12 carbon atoms, and examples thereof include pyridylthio, 2-benzimidazolylthio, 2-benzoxazolylthio, and 2-benzothiazolylthio), a sulfonyl group (preferably having 1 to 30 carbon atoms, more preferably having 1 to 20 carbon atoms, and particularly preferably having 1 to 12 carbon atoms, and examples thereof include mesyl and tosyl), a sulfinyl group (preferably having 1 to 30 carbon atoms, more preferably having 1 to 20 carbon atoms, and particularly preferably having 1 to 12 carbon atoms, and examples thereof include methanesulfinyl and benzenesulfinyl), an ureido group (preferably having 1 to 30 carbon atoms, more preferably having 1 to 20 carbon atoms, and particularly preferably having 1 to 12 carbon atoms, examples thereof include ureido, methylureido, and phenylureido), a phosphoric acid amide group (preferably having 1 to 30 carbon atoms, more preferably having 1 to 20 carbon atoms, and particularly preferably having 1 to 12 carbon atoms, and examples thereof include diethylphosphoric acid amide and phenylphosphoric acid amide), a hydroxy group, a mercapto group, a halogen atom (for example, a fluorine atom, a chlorine atom, a bromine atom, and an iodine atom), a cyano group, a sulfo group, a carboxyl group, a nitro group, a hydroxamic acid group, a sulfino group, a hydrazino group, an imino group, a heterocyclic group (preferably having 1 to 30 carbon atoms, and more preferably having 1 to 12 carbon atoms, and examples of the hetero atom include a nitrogen atom, an oxygen atom, a sulfur atom, and specific examples thereof include imidazolyl, pyridyl, quinolyl, furyl, thienyl, piperidyl, morpholino, benzoxazolyl, benzimidazolyl, benzothiazolyl, a carbazolyl group, and an azepinyl group), a silyl group (preferably having 3 to 40 carbon atoms, more preferably having 3 to 30 carbon atoms, and particularly preferably having 3 to 24 carbon atoms, and examples thereof include trimethylsilyl and triphenylsilyl), and an electron-withdrawing group. Among these, an electron-withdrawing group is preferable.

Examples of the electron-withdrawing group include a σp value (a sigma para value) of Hammett is preferably a positive substituent. Examples thereof include a cyano group, an acyl group, an alkyloxycarbonyl group, an aryloxycarbonyl group, a sulfamoyl group, a sulfinyl group, and a heterocyclic group. These electron-withdrawing groups may be further substituted.

A substituent constant σ value of Hammett is described. The Hammett's rule is an empirical rule advocated by L. P. Hammett in 1935 so as to quantitatively discuss the effect of a substituent on the reaction or equilibrium of a benzene derivative and its propriety is widely admitted at present. The substituent constant determined by the Hammett's rule includes a σp value and a σm value, and these values can be found in a large number of general publications. The Hammett's rule is described in detail, for example, in "Lange's Handbook of Chemistry", 12th edition, edited by J. A. Dean, 1979 (Mc Graw-Hill) and "Kagakuno Ryoiki" (Chemistry Region), special number, No. 122, pages 96 to 103, 1979 (Nankodo), and Chem. Rev., 1991, Vol. 91, pages 165 to 195. According to the invention, a substituent having a substituent constant σp value of Hammett of 0.2 or greater is an electron-withdrawing group. A σp value is preferably 0.25 or greater, more preferably 0.3 or greater, and particularly preferably 0.35 or greater. The upper limit is not particularly limited, but preferably 0.80.

Specific examples thereof include a cyano group (0.66), a carboxyl group (—COOH: 0.45), an alkoxycarbonyl group (—COOMe: 0.45), an aryloxycarbonyl group (—COOPh: 0.44), a carbamoyl group (—CONH$_2$: 0.36), an alkylcarbonyl group (—COMe: 0.50), an arylcarbonyl group (—COPh: 0.43), an alkylsulfonyl group (—SO$_2$Me: 0.72), or an arylsulfonyl group (—SO$_2$Ph: 0.68). Particularly preferably, an example is a cyano group.

In this specification, Me represents a methyl group, and Ph represents a phenyl group. Values in parentheses are σp values of typical substituents selected from pages 165 to 195 of Chem. Rev., 1991, Vol. 91.

$X^1$ and $X^2$ each independently represent a hydrogen atom or a substituent.

Examples of the substituent include an alkyl group, an aryl group, a heteroaryl group, a metal atom, and a group represented by Formula (2) below.

The number of carbon atoms of the alkyl group is preferably 1 to 40, more preferably 1 to 30, and particularly preferably 1 to 25. The alkyl group may have any one of a linear shape, a branched shape, or a cyclic shape, but a linear shape or a branched shape is preferable, and a linear shape is particularly preferable.

As the number of carbon atoms of the aryl group, 6 to 20 is preferable, and 6 to 12 is more preferable.

The heteroaryl group may be a monocyclic ring or may be a polycyclic ring, and a monocyclic ring is preferable. The number of hetero atoms forming the heteroaryl group is preferably 1 to 3. The hetero atom that forms a heteroaryl group is preferably a nitrogen atom, an oxygen atom, or a sulfur atom. The number of carbon atoms of the heteroaryl group is preferably 3 to 30, more preferably 3 to 18, further preferably 3 to 12, and particularly preferably 3 to 5. The heteroaryl group is preferably a 5-membered heterocyclic ring or a 6-membered heterocyclic ring. Specific examples of the heteroaryl group include imidazolyl, pyridyl, quinolyl, furyl, thienyl, benzoxazolyl, benzimidazolyl, benzothiazolyl, naphthothiazolyl, m-carbazolyl, and azepinyl.

As the metal atom, magnesium, aluminum, calcium, barium, zinc, tin, vanadium, iron, cobalt, nickel, copper, palladium, iridium, and platinum are preferable, and aluminum, zinc, vanadium, iron, copper, palladium, iridium, and platinum are particularly preferable.

$X^1$ and $X^2$ are preferably a hydrogen atom or a group represented by Formula (2) below.

(2)

In Formula (2), $R^{21}$ and $R^{22}$ each independently represent substituents and $R^{21}$ and $R^{22}$ may be bonded to each other to form a ring, and * represents an atomic bond.

Examples of the substituent represented by $R^{21}$ and $R^{22}$ include substituents represented by $R^9$ and $R^{10}$ described above and a group represented by -$L^{100}$-$X^{100}$ described above.

The substituent is preferably a halogen atom, an alkyl group, an aryl group, a heteroaryl group, and a group represented by -$L^{100}$-$X^{100}$ described above.

As the halogen atom, a fluorine atom, a chlorine atom, a bromine atom, and an iodine atom are preferable, and a fluorine atom is particularly preferable.

The alkyl group, the aryl group, and the heteroaryl group have the same meaning as the alkyl group, the aryl group, and the heteroaryl group described in $X^1$ and $X^2$, and preferable scopes thereof are the same.

$R^{21}$ and $R^{22}$ may be bonded to each other to form a ring. Examples of the ring formed by $R^{21}$ and $R^{22}$ bonded to each other include structures described below.

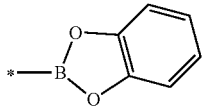

The compound represented by Formula (1) above is preferably a compound represented by Formula (3) below.

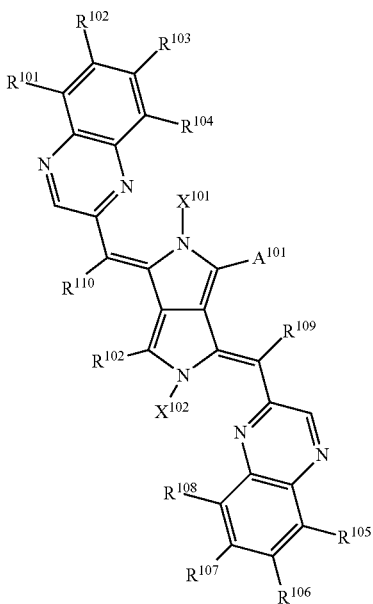

(3)

In Formula (3), $X^{101}$ and $X^{102}$ represent a hydrogen atom and a group represented by Formula (4), a group represented by Expression or (5) below, $R^{101}$ to $R^{108}$ each independently represent a hydrogen atom, a halogen atom, an alkyl group having 1 to 40 carbon atoms, an alkoxy group having 1 to 40 carbon atoms, an aryl group having 6 to 20 carbon atoms, a cyano group, and a group represented by $-L^{100}-X^{100}$ described above, at least one of $R^{101}$, $R^{102}$, $R^{103}$, $R^{104}$, $R^{105}$, $R^{106}$, $R^{107}$, or $R^{108}$ represents a halogen atom, an alkyl group having 1 to 40 carbon atoms, an alkoxy group having 1 to 40 carbon atoms, an aryl group having 6 to 20 carbon atoms, a cyano group or a group represented by $-L^{100}-X^{100}$ described above, $R^{109}$ and $R^{110}$ represent a cyano group, $A^{101}$ and $A^{102}$ each independently represent an aryl group having 6 to 20 carbon atoms, and a heteroaryl group having 3 to 18 carbon atoms.

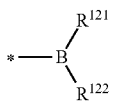

(4)

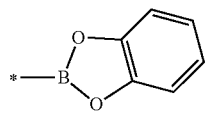

(5)

In Formula (4), $R^{121}$ and $R^{122}$ each independently represent a halogen atom, an alkyl group having 1 to 10 carbon atoms, an aryl group having 6 to 20 carbon atoms, a 5-membered heterocyclic ring, a 6-membered heterocyclic ring, or a group represented by $-L^{100}-X^{100}$ described above, and * represents an atomic bond.

In Formula (3), $X^{101}$ and $X^{102}$ represents a hydrogen atom, a group represented by Formula (4) described above, or a group represented by Formula (5) described above.

The halogen atom represented by $R^{121}$ and $R^{122}$ of Formula (4) described above is preferably a fluorine atom.

The number of carbon atoms of the alkyl group represented by $R^{121}$ and $R^{122}$ of Formula (4) described above is 1 to 10 and preferably 1 to 8.

The number of carbon atoms of the aryl group represented by $R^{121}$ and $R^{122}$ of Formula (4) above is 6 to 20 and preferably 6 to 12.

The hetero atom that forms a 5-membered heterocyclic ring or a 6-membered heterocyclic ring represented by $R^{121}$ and $R^{122}$ of Formula (4) described above is preferably a nitrogen atom, an oxygen atom, or a sulfur atom. The number of the hetero atoms is preferably 1 to 3.

In Formula (3), $R^{101}$ to $R^{108}$ each independently represent a hydrogen atom, a halogen atom, an alkyl group having 1 to 40 carbon atoms, an alkoxy group having 1 to 40 carbon atoms, an aryl group having 6 to 20 carbon atoms, a cyano group, and a group represented by $-L^{100}-X^{100}$ described above, at least one of $R^{101}$, $R^{102}$, $R^{103}$, $R^{104}$, $R^{105}$, $R^{106}$, $R^{107}$, or $R^{108}$ represents a halogen atom, an alkyl group having 1 to 40 carbon atoms, an alkoxy group having 1 to 40 carbon atoms, an aryl group having 6 to 20 carbon atoms, a cyano group, or a group represented by $-L^{100}-X^{100}$ described above.

As the halogen atom, a fluorine atom, a chlorine atom, a bromine atom, and an iodine atom are preferable, and a chlorine atom is particularly preferable.

The number of carbon atoms of the alkyl group is preferably 1 to 40, more preferably 1 to 30, and particularly preferably 1 to 25. The alkyl group may have any one of a linear shape, a branched shape, and a cyclic shape, but a linear shape or a branched shape is preferable, and a linear shape is particularly preferable.

The number of carbon atoms of the alkoxy group is preferably 1 to 40, more preferably 1 to 30, and particularly preferably 1 to 25. The alkoxy group may have any one of a linear shape, a branched shape, and a cyclic shape, but a linear shape or a branched shape is preferable, and a linear shape is particularly preferable.

The number of carbon atoms of the aryl group is preferably 6 to 20 and more preferably 6 to 12.

The substituent represented by $R^{101}$ to $R^{108}$ is preferably a halogen atom and a group represented by $-L^{100}-X^{100}$ described above, more preferably a halogen atom, and particularly preferably a chlorine atom.

It is preferable that at least one of $R^{101}$, $R^{102}$, $R^{103}$, or $R^{104}$ is a halogen atom or a group represented by $-L^{100}-X^{100}$, at least one of $R^{105}$, $R^{106}$, $R^{107}$, or $R^{108}$ is a halogen atom or a group represented by $-L^{100}-X^{100}$.

In Formula (3), $A^{101}$ and $A^{102}$ each independently represent an aryl group having 6 to 20 carbon atoms and a heteroaryl group having 3 to 18 carbon atoms.

The aryl group is preferably an aryl group having 6 to 12 carbon atoms and more preferably a phenyl group or a naphthyl group.

The heteroaryl group may have a monocyclic shape or a polycyclic shape. The number of hetero atoms that form the heteroaryl group is preferably 1 to 3. The hetero atoms that form the heteroaryl group are preferably nitrogen atoms, oxygen atoms, or sulfur atoms. The number of carbon atoms of the heteroaryl group is preferably 3 to 12.

The aryl group and the heteroaryl group described above may have substituents and may be unsubstituted. For the reason that solubility to a solvent can be improved, an aryl group and a heteroaryl group preferably have substituents. The substituent include an alkyl group, an alkoxy group, a group represented by -L-$R^{x1}$ described above, and a group represented by -$L^{100}$-$X^{100}$ described above.

The number of carbon atoms of the alkyl group is preferably 1 to 40, more preferably 1 to 30, and particularly preferably 1 to 25. The alkyl group may have any one of a linear shape, a branched shape, a cyclic shape, but a linear shape or a branched shape is preferable, and a branched shape is particularly preferable.

The number of carbon atoms of the alkoxy group is preferably 1 to 40, more preferably 1 to 30, and particularly preferably 1 to 25. The alkoxy group may be any one of a linear shape, a branched shape, and a cyclic shape, but a linear shape or a branched shape is preferable, and a branched shape is particularly preferable.

As the compound represented by Formula (1), for example, compounds or the like described below can be exemplified. In formulae below, "—$C_{19}H_{39}$" and "—$OC_8H_{17}$" are respectively branched. "—$OC_4H_9$", "—$C_{18}H_{37}$", and "—$OC_{18}H_{37}$" are linear alkyl or linear alkoxy.

In compounds 37 to 39, one of $R^1$ and $R^2$ represents a hydrogen atom, and the other represents a substituent R, and one of $R^3$ and $R^4$ represents a hydrogen atom and the other represents a substituent R.

1

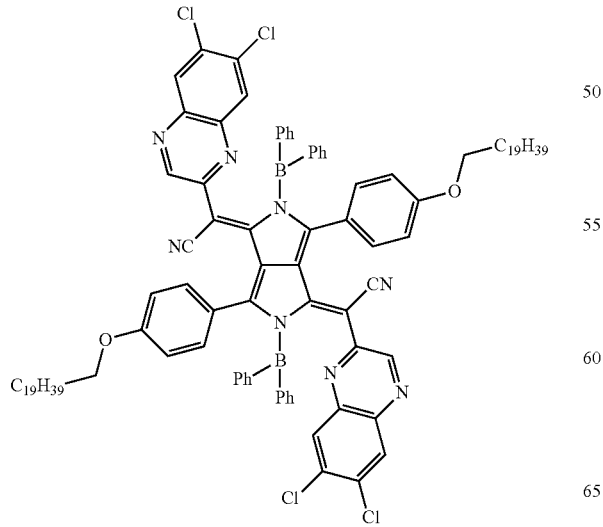

2

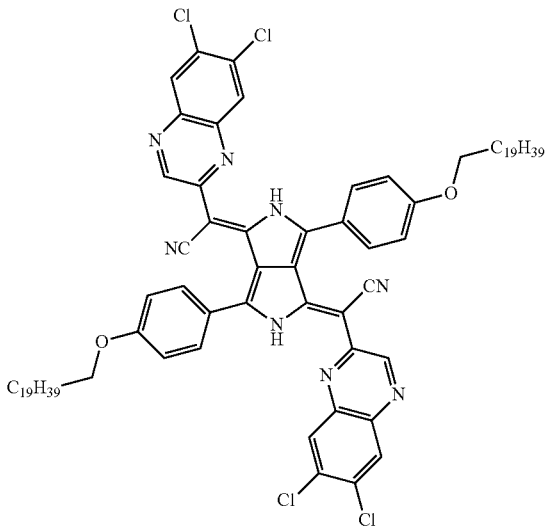

3

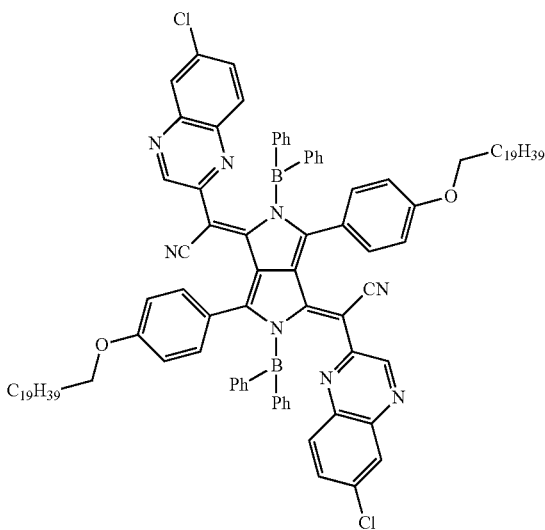

4

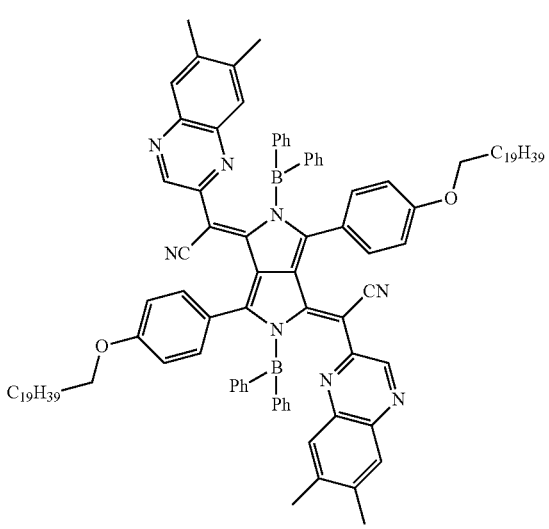

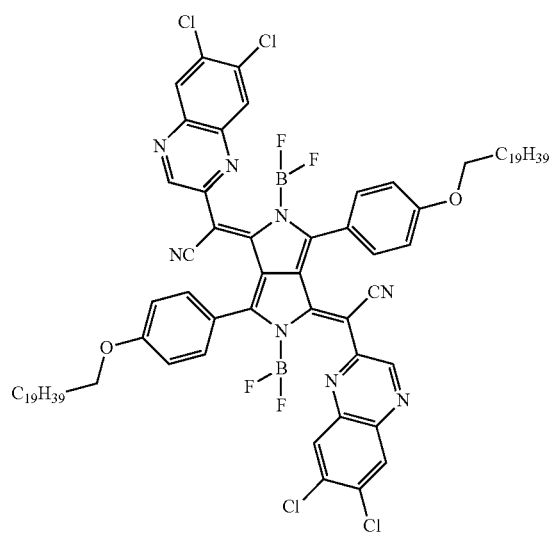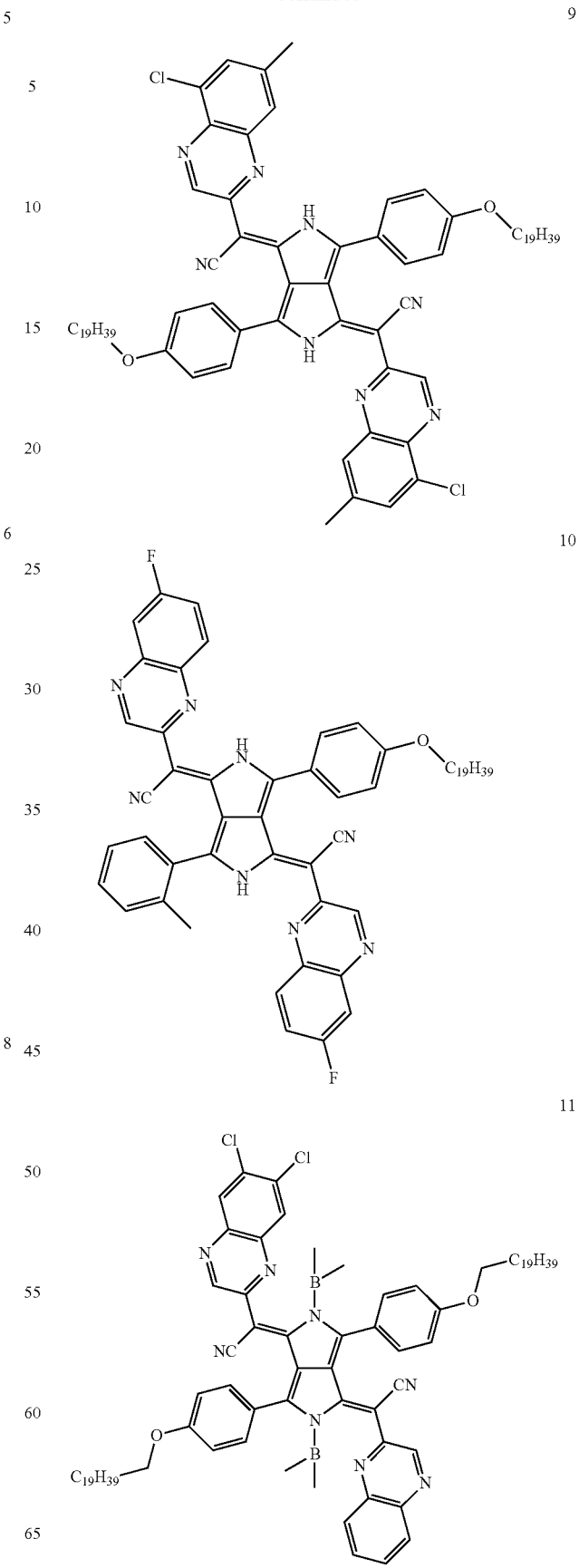

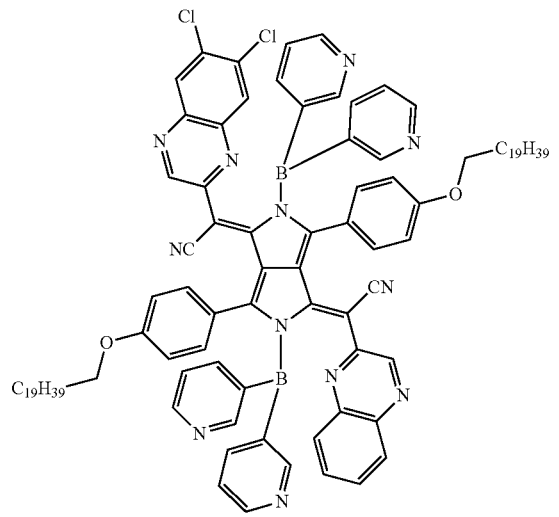
13
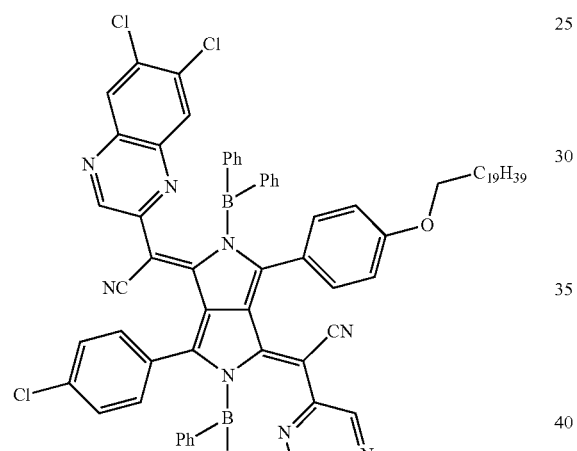
14
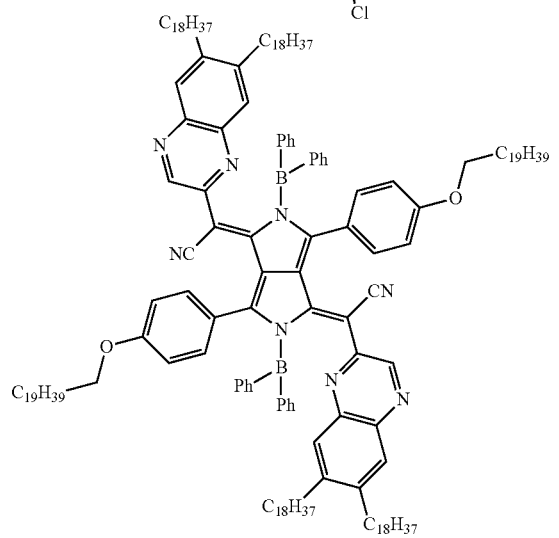
15
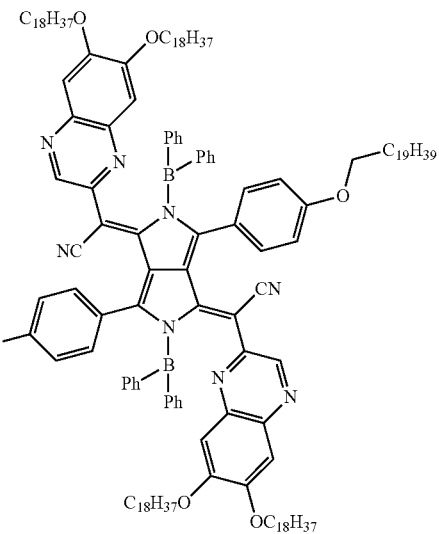
16
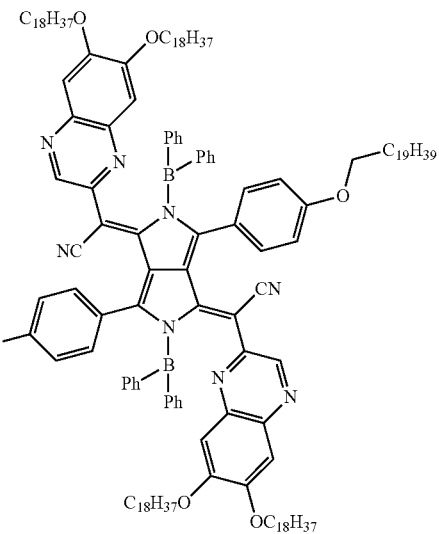
17

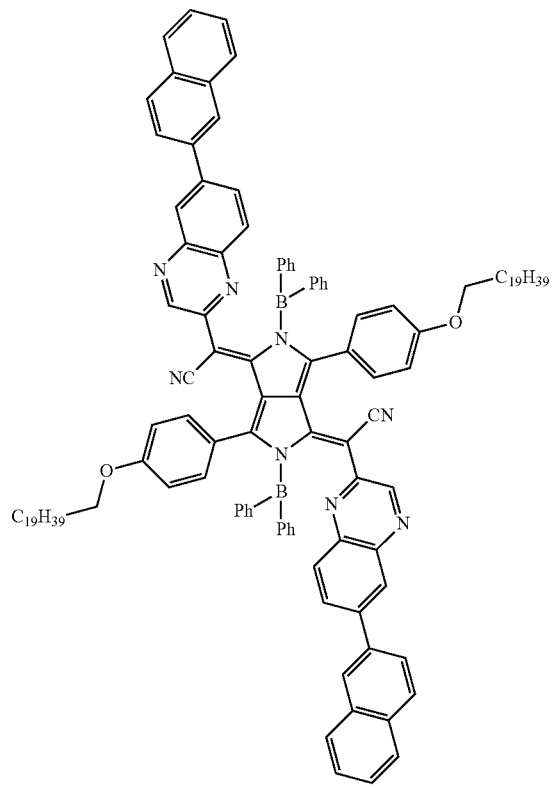
18
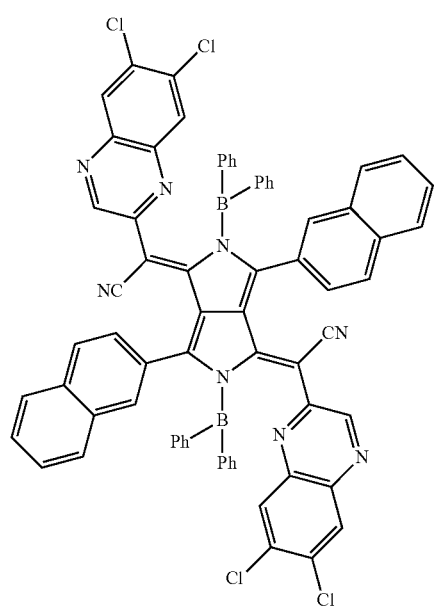
19
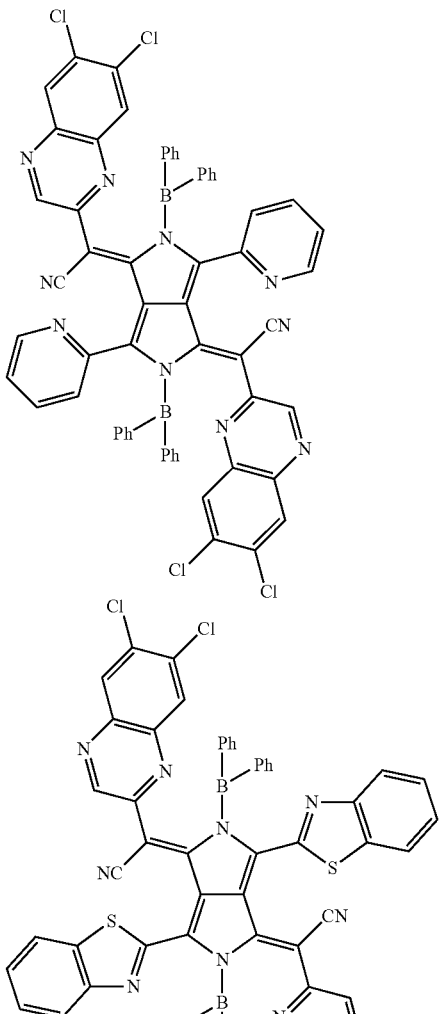
20
21
22

23
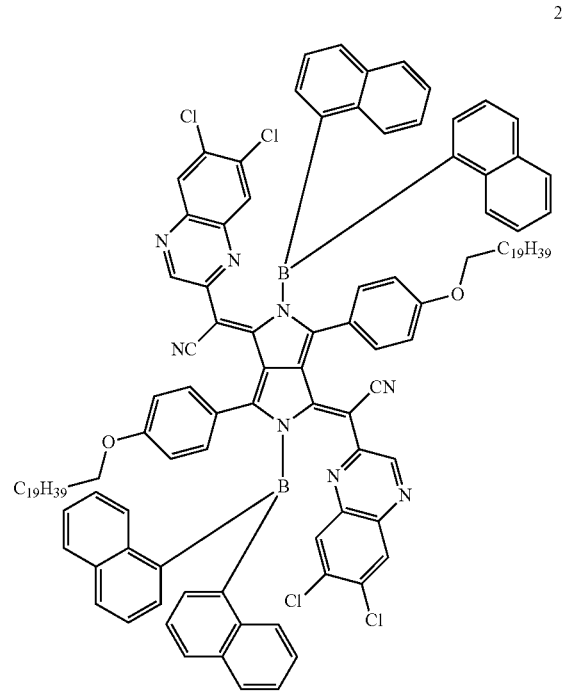
24
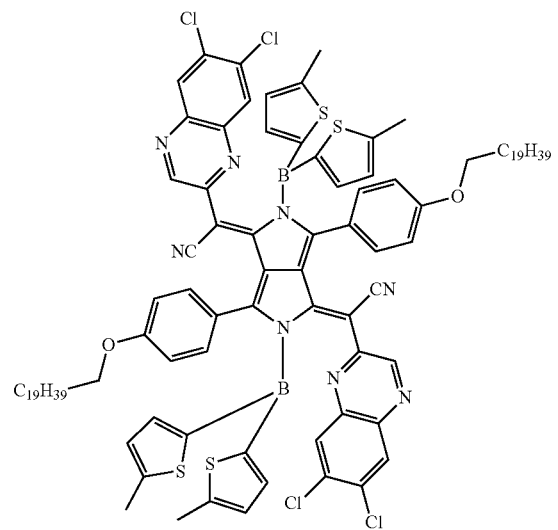
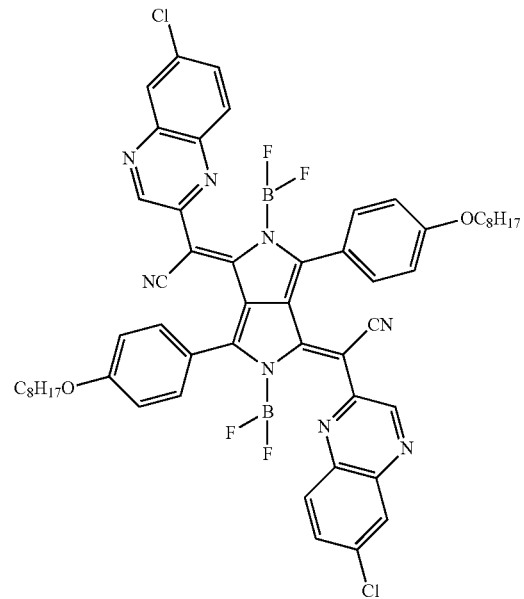
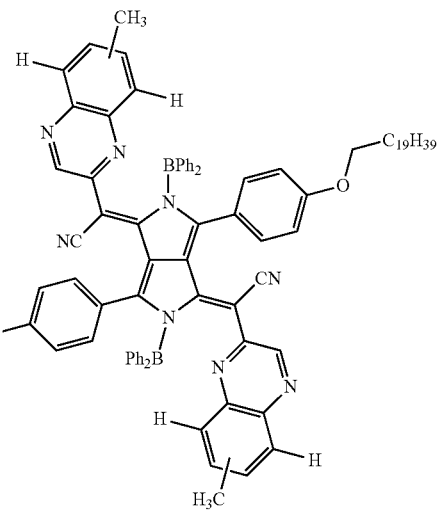
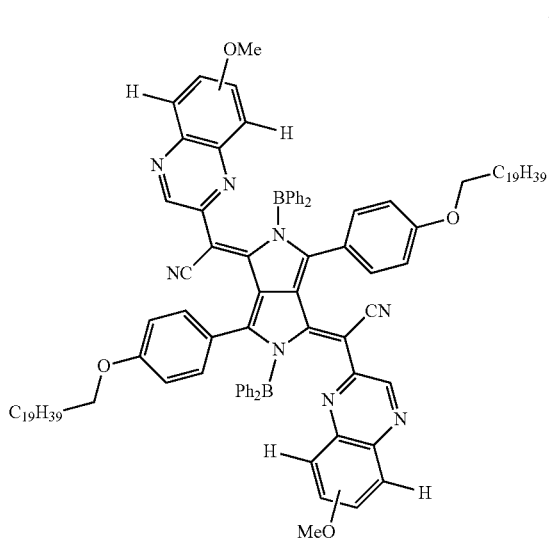

-continued
27
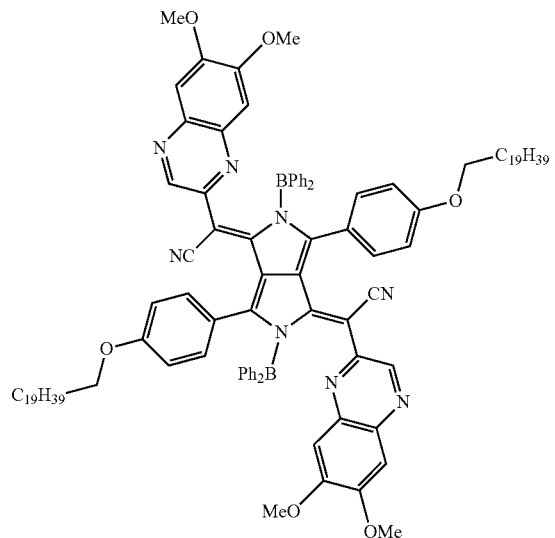
28
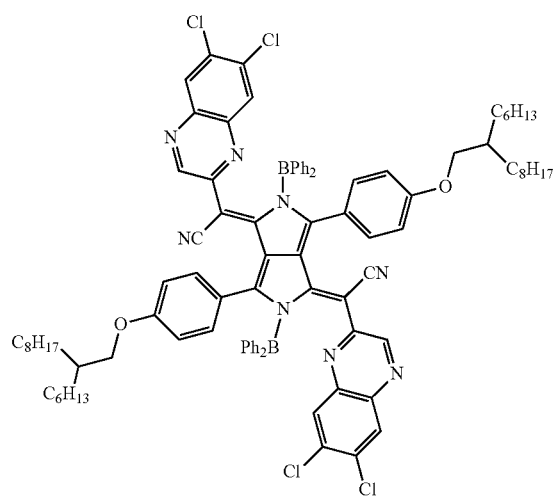
29
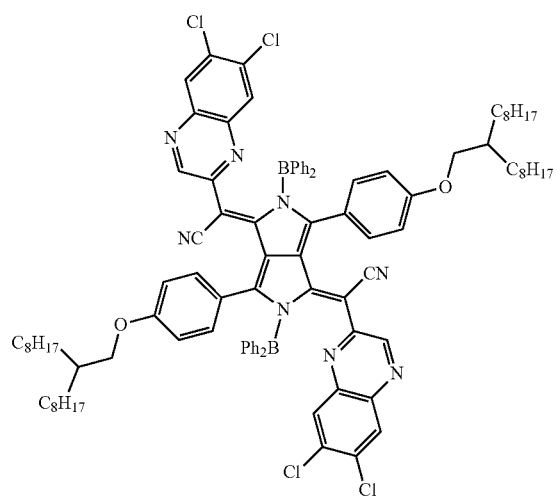
-continued
30
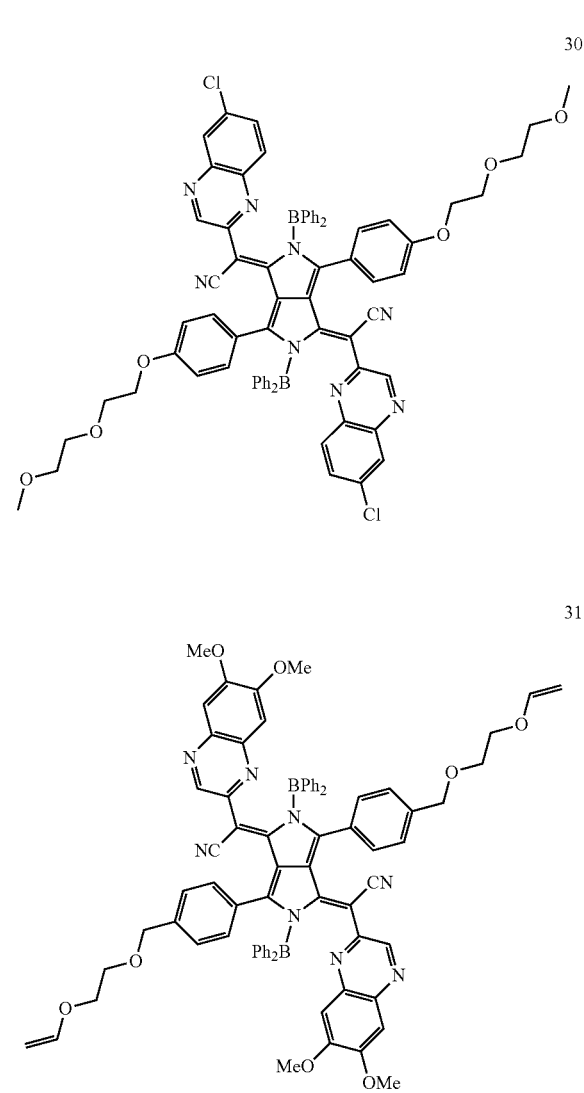
32
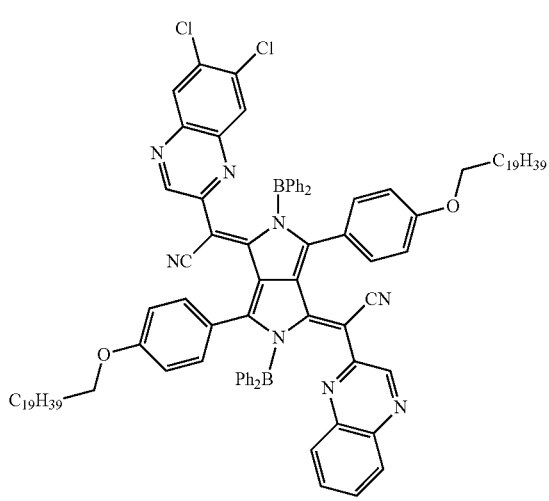

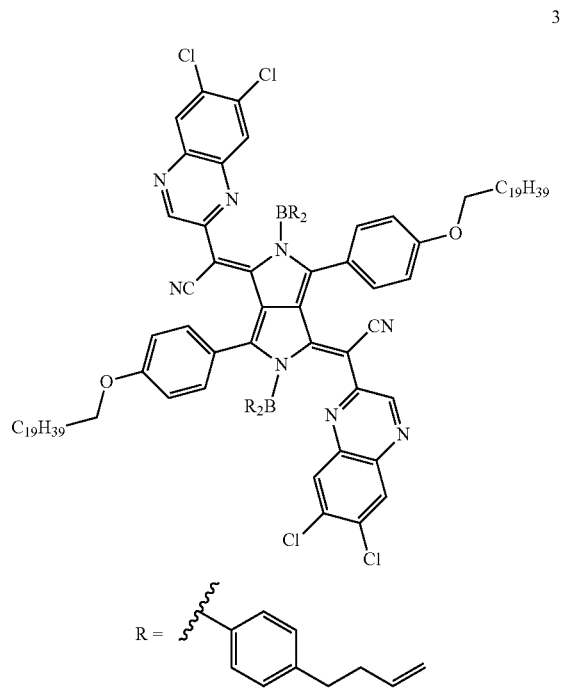
33
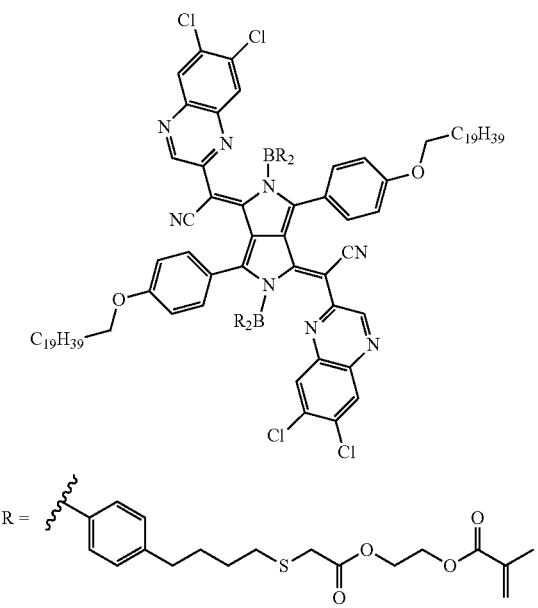
35
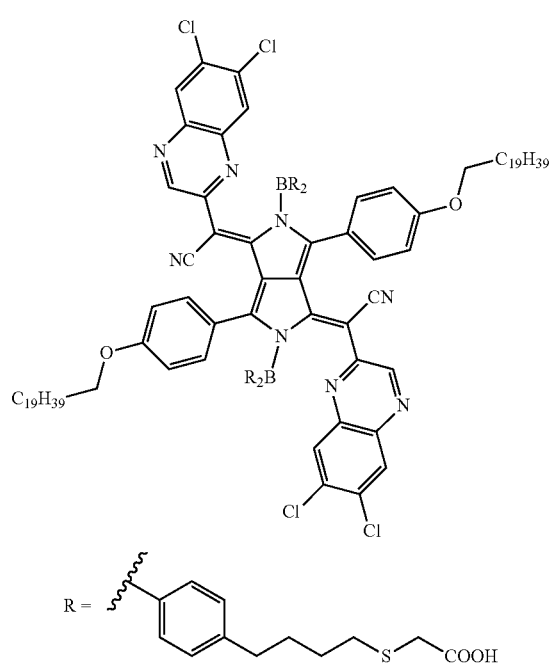
34
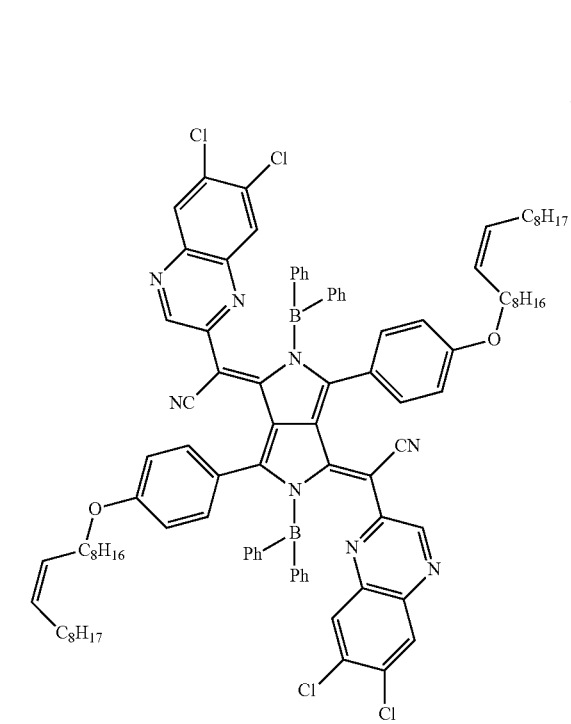
36

-continued
37
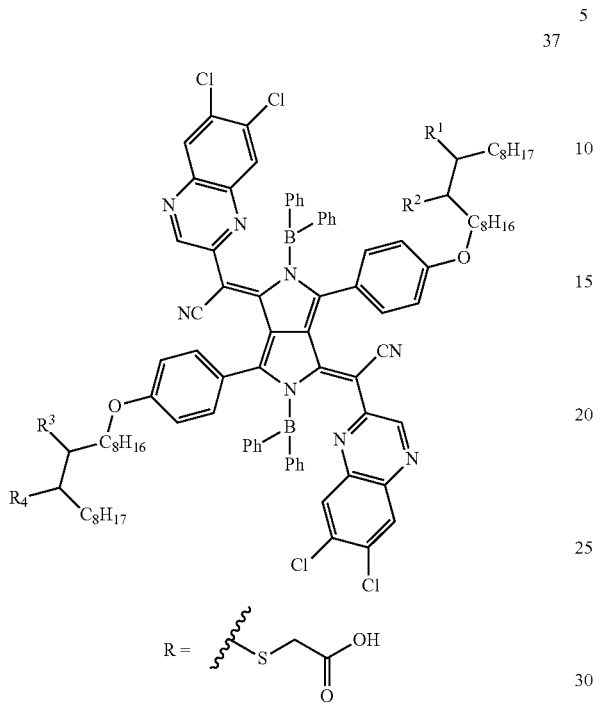
38
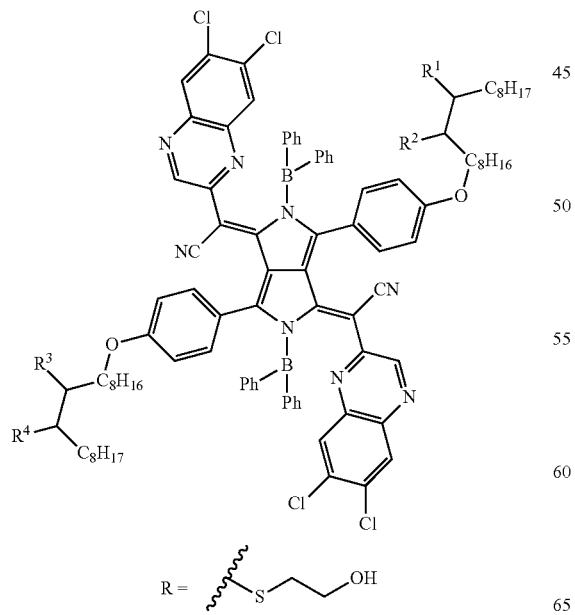
-continued
39
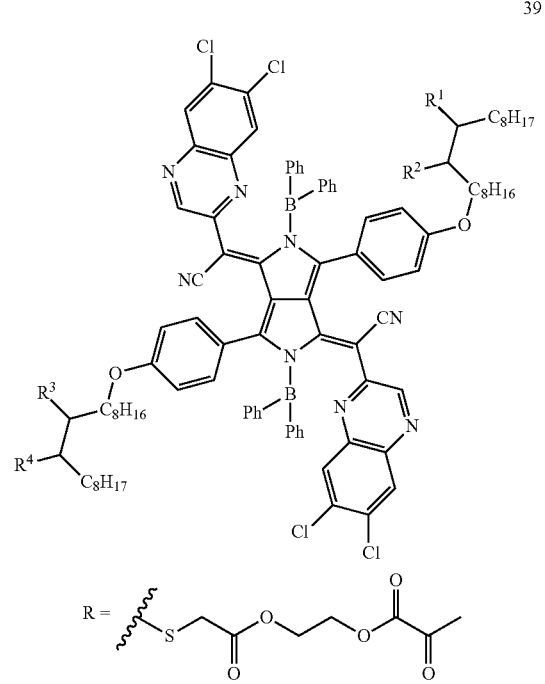
40
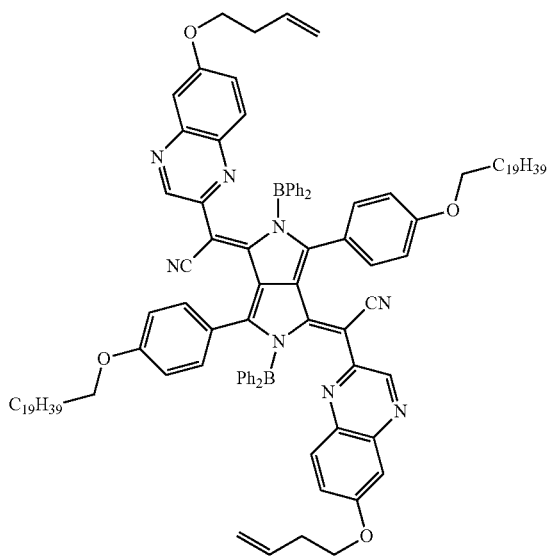

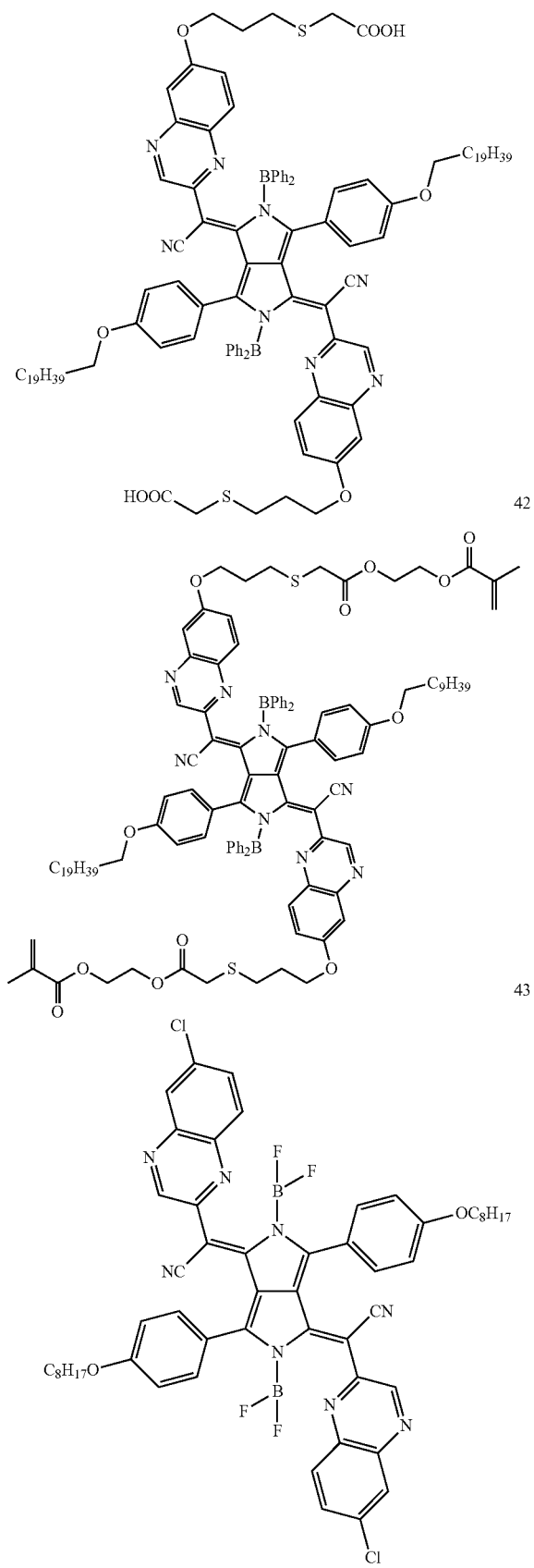

In the near-infrared ray absorption composition according to the invention, the content of the compound represented by Formula (1) can be adjusted, if necessary. For example, the content is preferably 0.01 to 50 mass % in the total solid content of the composition. The lower limit is preferably 0.1 mass % or greater and more preferably 0.5 mass % or greater. The upper limit is preferably 30 mass % or less and more preferably 15 mass % or less. If the content is in this range, satisfactory near infrared ray absorption properties can be applied. In a case where the near-infrared ray absorption composition according to the invention includes two or more types of compounds represented by Formula (1), the total amount thereof is preferably in the range described above.

The near-infrared ray absorption composition according to the invention can be used, for example, as (i) the use of a near-infrared ray absorption filter that can absorb light in a specific near infrared ray range, (ii) a near-infrared ray absorption filter that can absorb light in a near infrared ray range in a wavelength range wider than a wavelength range that is cut only by the compound represented by Formula (1), and the like.

In a case where the near-infrared ray absorption composition is used as the use of the near-infrared ray absorption filter of (i) above, it is preferable that the near-infrared ray absorption composition according to the invention contains the compound represented by Formula (1) and does substantially not contain an infrared ray absorption substance having a maximum absorption wavelength in a near infrared ray range different from a maximum absorption wavelength of a compound represented by Formula (1). Here, the expression "substantially not containing" means that a content of the compound represented by Formula (1) is 1 mass % or less. A curable compound, a hardening agent, a surfactant, a solvent, and the like may be contained.

In a case where the near-infrared ray absorption composition is used as the use of the near-infrared ray absorption filter of (ii) above, the near-infrared ray absorption composition according to the invention preferably contains an infrared ray absorption substance having a maximum absorption wavelength in a near infrared ray range different from a maximum absorption wavelength included in the compound represented by Formula (1), in addition to the compound represented by Formula (1). The near-infrared ray absorption composition may contain a curable compound, a hardening agent, a surfactant, a solvent, and the like.

Hereinafter, other components that may be contained in the near-infrared ray absorption composition according to the invention are described.

<<Curable Compound>>

The near-infrared ray absorption composition according to the invention may contain a curable compound. As the curable compound, a compound having a polymerizable group (hereinafter, referred to as a "polymerizable compound") is preferable. Examples thereof include a compound including an ethylenically unsaturated bond, cyclic ether (epoxy and oxetane), and the like. This compound group is widely known and particularly these can be used without limitation. For example, these may be any one of chemical forms such as a monomer, an oligomer, a prepolymer, and a polymer.

The polymerizable compound may be monofunctional or may be polyfunctional, but the polymerizable compound is preferably polyfunctional. If a polyfunctional compound is included, a near infrared ray shielding properties and heat resistance can be further improved. The number of functional groups is not particularly limited, but the polymerizable compound is preferably difuntional to octafunctional and further preferably trifunctional to hexafunctional.

In a case where a curable compound is contained in the near-infrared ray absorption composition according to the invention, together with the compound represented by Formula (1) above, preferable embodiments of the curable compound include compounds below. The invention is not limited to embodiments below.

<<<Compound Including Ethylenically Unsaturated Bond>>>

As examples of the compound including an ethylenically unsaturated bond, paragraphs 0033 and 0034 of JP2013-253224A can be referred to, and the contents thereof are incorporated to this specification.

As a compound including an ethylenically unsaturated bond, ethyleneoxy-modified pentaerythritol tetraacrylate (as a commercially available product, NK ESTER ATM-35E; manufactured by Shin-Nakamura Chemical Co., Ltd.), dipentaerythritol triacrylate (as a commercially available product, KAYARAD D-330; manufactured by manufactured by Nippon Kayaku Co., Ltd.), dipentaerythritol tetraacrylate (as a commercially available product, KAYARAD D-320; manufactured by Nippon Kayaku Co., Ltd.), dipentaerythritol penta(meth)acrylate (as a commercially available product, KAYARAD D-310; manufactured by Nippon Kayaku Co., Ltd.), dipentaerythritol hexa(meth)acrylate (as commercially available products, KAYARAD DPHA; manufactured by Nippon Kayaku Co., Ltd., A-DPH-12E; manufactured by Shin-Nakamura Chemical Co., Ltd.), and a structure in which ethylene glycol, propylene glycol residues are interposed between these (meth)acryloyl groups are preferable. An oligomer type of these can be used.

Polymerizable compounds of paragraphs 0034 to 0038 disclosed in JP2013-253224A can be referred to, and the contents thereof are incorporated to this specification.

Examples thereof include polymerizable monomers disclosed in paragraphs 0477 of JP2012-208494A ("0585" of corresponding US2012/0235099A), and the contents thereof are incorporated to this specification.

Diglycerine ethyleneoxide (EO)-modified (meth)acrylate (as a commercially available product, M-460; manufactured by Toagosei Co., Ltd.) is preferable. Pentaerythritol tetraacrylate (manufactured by Shin-Nakamura Chemical Co., Ltd., A-TMMT), 1,6-hexanediol diacrylate (manufactured by Nippon Kayaku Co., Ltd., KAYARAD HDDA) is also preferable. An oligomer type of these can be used. Examples thereof include RP-1040 (manufactured by Nippon Kayaku Co., Ltd.).

A compound including an ethylenically unsaturated bond is a polyfunctional monomer, and may have an acid group such as a carboxyl group, a sulfonic acid group, and a phosphoric acid group. In a case where a compound including an ethylenically unsaturated bond has an unreacted carboxyl group, an acid group may be introduced by being reacted with a non-aromatic carboxylic acid anhydride, if necessary. Specific examples of the non-aromatic carboxylic acid anhydride include tetrahydrophthalic acid anhydride, alkylated tetrahydrophthalic acid anhydride, hexahydrophthalic acid anhydride, alkylated hexahydrophthalic acid anhydride, succinic acid anhydride, and maleic acid anhydride.

Examples of a compound including an ethylenically unsaturated bond having an acid group include ester between an aliphatic polyhydroxy compound and an unsaturated carboxylic acid. A polyfunctional monomer caused to have an acid group by being reacted with a non-aromatic carboxylic acid anhydride is preferable in an unreacted hydroxyl group of an aliphatic polyhydroxy compound. Particularly preferably, an aliphatic polyhydroxy compound is pentaerythritol and/or dipentaerythritol. Examples of a commercially available product include M-305, M-510, and M-520 of ARONIX series, as a polybasic acid-modified acrylic oligomer manufactured by Toagosei Co., Ltd.

A polyfunctional monomer acid value having an acid group is preferably 0.1 to 40 mgKOH/g. The lower limit is preferably 5 mgKOH/g or greater. The upper limit is preferably 30 mgKOH/g or less. In a case where two or more types of different polyfunctional monomers of the acid group are used together, or in a case where a polyfunctional monomer without an acid group are used together, preparation is performed such that an acid value as the entire polyfunctional monomer is in the range described above.

The compound including an ethylenically unsaturated bond may be a polymer having a repeating unit having an ethylenically unsaturated bond. Specific examples thereof include a polymer (copolymer) having repeating units below.

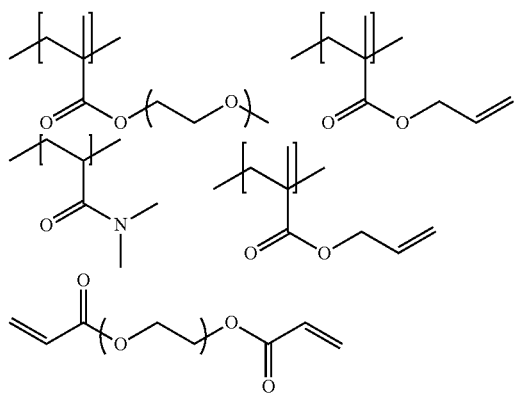

<<<Compound Having Epoxy Group or Oxetanyl Group>>>

A second preferable embodiment according to the invention is an embodiment of including a compound having an epoxy group or an oxetanyl group as a polymerizable compound. Specific examples of the compound having an epoxy group or an oxetanyl group include a polymer having an epoxy group on a side chain, a polymerizable monomer or a polymerizable oligomer that has two or more epoxy groups in a molecule. Specific examples thereof include a Bisphenol A-type epoxy resin, a Bisphenol F-type epoxy resin, a phenol novolac-type epoxy resin, a cresol novolac-type epoxy resin, and an aliphatic epoxy resin. Examples thereof include a monofunctional or polyfunctional glycidyl ether compound, and a polyfunctional aliphatic glycidyl ether compound is preferable.

As these compounds, commercially available products may be used, or these compounds can be obtained by introducing an epoxy group or an oxetanyl group to a side chain of a polymer.

As a commercially available product, for example, disclosure of paragraph 0191 of JP2012-155288A can be referred to, and the contents thereof are incorporated to this specification.

Examples of a commercially available product include a polyfunctional aliphatic glycidyl ether compound such as DENACOL EX-212L, EX-214L, EX-216L, EX-321L, and EX-850L (above, manufactured by Nagase ChemteX Corporation). These are low chlorine products, but EX-212, EX-214, EX-216, EX-321, EX-850, and the like which are not low chlorine products can be used in the same manner.

Examples thereof also include ADEKA RESIN EP-4000S, ADEKA RESIN EP-4003S, ADEKA RESIN EP-4010S, and ADEKA RESIN EP-4011S (above, manufactured by ADEKA Corporation), NC-2000, NC-3000, NC-7300, XD-1000, EPPN-501, and EPPN-502 (above, manufactured by ADEKA Corporation), JER1031 S, CELLOXIDE 2021P, CELLOXIDE 2081, CELLOXIDE 2083, CELLOXIDE 2085, EHPE3150, EPOLEAD PB 3600, EPOLEAD PB 4700 (above, manufactured by Daicel Corporation), CYCLOMER P ACA 200M, CYCLOMER P ACA 230AA, CYCLOMER P ACA Z250, CYCLOMER P ACA Z251, CYCLOMER P ACA Z300, and CYCLOMER P ACA Z320 (above, manufactured by Daicel Corporation).

As specific examples of a polymer having an oxetanyl group on a side chain and a polymerizable monomer or a polymerizable oligomer that have two or more oxetanyl groups in a molecule, ARON OXETANE OXT-121, OXT-221, OX-SQ, and PNOX (above, manufactured by Toagosei Co., Ltd.) can be used.

A molecular weight is preferably in the range of 500 to 5,000,000 and further 1,000 to 500,000 by a weight average.

As a compound having an epoxy group or an oxetanyl group, a compound having a glycidyl group as a epoxy group such as glycidyl (meth)acrylate or allyl glycidyl ether can be used, but a preferable compound is an unsaturated compound having an alicyclic epoxy group. As an example of this compound, disclosure of paragraph 0045 or the like of JP2009-265518A can be referred to, and the contents thereof are incorporated to this specification.

The compound including an epoxy group or an oxetanyl group may be a polymer having an epoxy group or an oxetanyl group as a repeating unit. Specific examples thereof include a polymer (copolymer) having repeating units below.

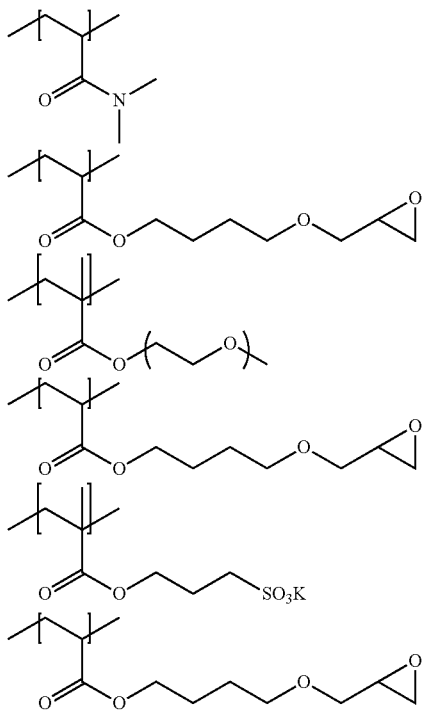

<<<Polyfunctional Monomer Having a Caprolactone-Modified Structure>>>

The near-infrared ray absorption composition may contain a polyfunctional monomer having a caprolactone-modified structure as a curable compound.

As a polyfunctional monomer having a caprolactone-modified structure, disclosure of paragraphs 0042 to 0045 of JP2013-253224A can be referred to, and the contents thereof are incorporated to this specification.

Examples of a commercially available product include SR-494 which is tetrafunctional acrylate having four ethyleneoxy chains manufactured by Sartomer, DPCA-60 which is hexafunctional acrylate having six pentyleneoxy chains manufactured by Nippon Kayaku Co., Ltd., and TPA-330 which is trifunctional acrylate having three isobutyleneoxy chains.

In a case where the near-infrared ray absorption composition according to the invention contains a curable compound, the content of the curable compound is preferably 1 to 90 mass % with respect to the total solid content except for a solvent. The lower limit is preferably 15 mass % or greater and more preferably 40 mass % or greater. The upper limit is preferably 80 mass % or less and more preferably 75 mass % or less.

In a case where a polymer including a repeating unit having a polymerizable group is used as a curable compound, a content of the polymer is preferably 10 to 75 mass % with respect to a total solid content of the near-infrared ray absorption composition according to the invention except for a solvent. The lower limit is preferably 20 mass % or greater and more preferably 25 mass % or greater. The upper limit is preferably 65 mass % or less and more preferably 60 mass % or less.

The curable compound may be used singly or two or more types may be used in combination. In a case where two or more types are used, it is preferable that a total amount is in the range described above.

<<Photopolymerization Initiator>>

The near-infrared ray absorption composition according to the invention may contain a photopolymerization initiator.

The content of the photopolymerization initiator is preferably 0.01 to 30 mass %. The lower limit is preferably 0.1 mass % or greater and more preferably 0.5 mass % or greater. The upper limit is preferably 20 mass % or less and more preferably 15 mass % or less.

The photopolymerization initiator may be used singly or two or more types may be used in combination. In a case where two or more types are used, it is preferable that a total amount is in the range described above.

The photopolymerization initiator is not particularly limited, as long as the photopolymerization initiator has capability of initiating polymerization of the curable compound by light. The photopolymerization initiator can be appropriately selected depending on purposes. In a case where polymerization is initiated by light, it is preferable to have photosensitivity on visible light from an ultraviolet ray range.

The photopolymerization initiator is preferably a compound having at least an aromatic group, and examples thereof include an acylphosphine compound, an acetophenone compound, an α-aminoketone compound, a benzophenone-based compound, a benzoin ether-based compound, a ketal derivative compound, a thioxanthone compound, an oxime compound, a hexaarylbiimidazole compound, a trihalomethyl compound, an azo compound, an organic peroxide, an onium salt compound such as a diazonium compound, an iodonium compound, a sulfonium compound, an azinium compound, a benzoin ether-based compound, a ketal derivative compound, and a metallocene compound, an organic boron salt compound, a disulfone compound, and a thiol compound.

As the photopolymerization initiator, disclosure of paragraphs 0217 to 0228 of JP2013-253224A can be referred to, and the contents thereof are incorporated to this specification.

As the oxime compound, IRGACURE-OXE01 (manufactured by BASF SE Corp.), IRGACURE-OXE02 (manufactured by BASF SE Corp.), TR-PBG-304 (manufactured by Changzhou Tronly New Electronic Materials Co., Ltd.), ADEKA ARKLS NCI-831 (manufactured by ADEKA Corporation), ADEKA ARKLS NCI-930 (manufactured by ADEKA Corporation), or the like which are commercially available products can be used.

As an acetophenone-based compound, IRGACURE-907, IRGACURE-369, and IRGACURE-379 (Product name: all are manufactured by BASF Japan Ltd.) which are commercially available products can be used. As an acylphosphine compound, IRGACURE-819 or DAROCUR-TPO (Product name: all are manufactured by BASF Japan Ltd.) which are commercially available products can be used.

The invention can use an oxime compound having a fluorine atom as the photopolymerization initiator. Specific examples of the oxime compound having a fluorine atom include compounds disclosed in JP2010-262028A, compounds 24, and 36 to 40 disclosed in JP2014-500852A, a compound (C-3) disclosed in JP2013-164471A. The contents thereof are incorporated to this specification.

<<Solvent>>

The near-infrared ray absorption composition according to the invention may contain a solvent. The solvent is not particularly limited, and can be appropriately selected depending on purposes, as long as respective components of the near-infrared ray absorption composition according to the invention can be evenly dissolved or dispersed in the solvent. For example, water or an organic solvent can be used.

Examples of the solvent suitably include alcohols (for example, methanol), ketones, esters, aromatic hydrocarbons, halogenated hydrocarbons, and dimethylformamide, dimethylacetamide, dimethylsulfoxide, and sulfolane. These may be used singly or two or more types thereof may be used in combination. In a case where two or more types of solvents are used together, a mixed solution formed with two or more types selected from methyl 3-ethoxypropionate, ethyl 3-ethoxypropionate, ethyl cellosolve acetate, ethyl lactate, diethylene glycol dimethyl ether, butyl acetate, methyl 3-methoxypropionate, 2-heptanone, cyclohexanone, ethyl carbitol acetate, butyl carbitol acetate, ethylene glycol monobutyl ether acetate, propylene glycol monomethyl ether, and propylene glycol monomethyl ether acetate are preferable.

Specific examples of alcohols, aromatic hydrocarbons, and halogenated hydrocarbons include those disclosed in paragraph 0136 of JP2012-194534A, and the contents thereof are incorporated to this specification. Specific examples of esters, ketones, and ethers include those disclosed in paragraph 0497 of JP2012-208494A ("0609" of corresponding US2012/0235099A), and examples thereof further include n-amyl acetate, ethyl propionate, dimethyl phthalate, ethyl benzoate, methyl sulfate, acetone, methyl isobutyl ketone, diethyl ether, and ethylene glycol monobutyl ether acetate.

The amount of the solvent in the near-infrared ray absorption composition according to the invention is preferably an amount in which a solid content of the compound represented by Formula (1) becomes 10 to 90 mass %. The lower limit is preferably 20 mass % or greater. The upper limit is preferably 80 mass % or less.

The solvent is preferably 10 to 90 mass % with respect to the compound represented by Formula (1). The lower limit is preferably 20 mass % or greater. The upper limit is preferably 80 mass % or less.

The solvent may be used singly, and two or more types thereof may be used in combination. In a case where two or more types are used, a total amount thereof is in the range described above.

<<Alkali Soluble Resin>>

The near-infrared ray absorption composition according to the invention may contain an alkali soluble resin.

The alkali soluble resin can be appropriately selected from alkali soluble resins which are linear organic high molecular polymers and have at least one group that promotes alkali solubility in a molecule (preferably, a molecule using an acrylic copolymer or a styrene-based copolymer as a main chain). In view of heat resistance, a polyhydroxystyrene-based resin, a polysiloxane-based resin, an acrylic resin, an acrylamide-based resin, and acryl/acrylamide copolymer resins are preferable. In view of developability control, an acrylic resin, an acrylamide-based resin, and an acryl/acrylamide copolymer resins are preferable.

Examples of a group promoting alkali solubility (hereinafter, also referred to as an acid group) include a carboxyl group, a phosphoric acid group, a sulfonic acid group, and a phenolic hydroxyl group. However, groups that are soluble to an organic solvent and can be developed by a weak alkali aqueous solution are preferable, and (meth)acrylic acid is particularly preferable. These acid groups may be used singly or two or more types thereof may be used in combination. As the alkali soluble resin, disclosure of paragraphs 0558 to 0571 ("0685" to "0700" of corresponding US2012/0235099A) or following paragraphs of JP2012-208494A is referred to, and the contents thereof are incorporated to this specification.

The acid value of the alkali soluble resin is preferably 30 to 200 mgKOH/g. The lower limit is preferably 50 mgKOH/g or greater and more preferably 70 mgKOH/g or greater. The upper limit is preferably 150 mgKOH/g or less and more preferably 120 mgKOH/g or less.

The weight-average molecular weight (Mw) of the alkali soluble resin is preferably 2,000 to 50,000. The lower limit is preferably 5,000 or greater and more preferably 7,000 or greater. The upper limit is preferably 30,000 or less and more preferably 20,000 or less.

In a case where the near-infrared ray absorption composition according to the invention contains an alkali soluble resin, the content of the alkali soluble resin is preferably 1 to 80 mass % with respect to the total solid content of the near-infrared ray absorption composition. The lower limit is preferably 5 mass % or greater and more preferably 7 mass % or greater. The upper limit is preferably 50 mass % or less and more preferably 30 mass % or less.

The near-infrared ray absorption composition according to the invention may include only one type of alkali soluble resin and may include two or more types thereof. In a case where the near-infrared ray absorption composition includes two or more types thereof, it is preferable that a total amount is in the range described above.

<<Surfactant>>

The near-infrared ray absorption composition according to the invention may contain a surfactant. Only one type of surfactant may be used or two or more types thereof may be used in combination. The content of the surfactant is preferably 0.0001 to 2 mass % with respect to the solid content of the near-infrared ray absorption composition according to the invention. The lower limit is preferably 0.005 mass % or greater and more preferably 0.01 mass % or greater. The upper limit is preferably 1.0 mass % or less and more preferably 0.1 mass % or less.

As the surfactant, various surfactants such as a fluorine-based surfactant, a nonionic surfactant, a cation-based surfactant, an anion-based surfactant, and a silicone-based surfactant can be used. Particularly, if the near-infrared ray absorption composition according to the invention contains at least one of a fluorine-based surfactant or a silicone-based surfactant, liquid characteristics (particularly, fluidity) when the near-infrared ray absorption composition is prepared as a coating liquid are further improved. Accordingly, uniformity of coating thickness and liquid saving properties are further improved.

That is, in a case where a film is formed by using a coating liquid to which a near-infrared ray absorption composition containing at least one of the fluorine-based surfactant or the silicone-based surfactant, interfacial tension between a coated surface and a coating liquid is reduced, so as to improve wettability to a coated surface and improve coating properties to the coated surface. Therefore, even in a case where a thin film in about several μm is formed with a small amount of liquid amount, it is effective that a film that has small thickness unevenness and has a homogeneous thickness can be more suitably formed.

A fluorine content of the fluorine-based surfactant is suitably 3 to 40 mass %, more preferably 5 to 30 mass %, and particularly preferably 7 to 25 mass %. A fluorine-based surfactant having a fluorine content in the range described above is effective in view of uniformity of thickness or liquid saving properties of a coated film, and solubility in the near-infrared ray absorption composition is satisfactory.

Specific examples of the fluorine-based surfactant include surfactants disclosed in paragraph 0552 of JP2012-208494A ("0678" of corresponding US2012/0235099A), and the contents thereof are incorporated to this specification. Examples of the commercially available product of the fluorine-based surfactant include MEGAFACE F-171, MEGAFACE F-172, MEGAFACE F-173, MEGAFACE F-176, MEGAFACE F-177, MEGAFACE F-141, MEGAFACE F-142, MEGAFACE F-143, MEGAFACE F-144, MEGAFACE R30, MEGAFACE F-437, MEGAFACE F-475, MEGAFACE F-479, MEGAFACE F-482, MEGAFACE F-554, MEGAFACE F-780, MEGAFACE F-781F (above, manufactured by DIC Corporation), FLUORAD FC430, FLUORAD FC431, FLUORAD FC171 (above, manufactured by Sumimoto 3M Limited), SURFLON S-382, SURFLON SC-101, SURFLON SC-103, SURFLON SC-104, SURFLON SC-105, SURFLON SC-1068, SURFLON SC-381, SURFLON SC-383, SURFLON S-393, and SURFLON KH-40 (above, Asahi Glass Co., Ltd.).

Examples of the nonionic surfactant include polyoxyethylene alkyl ether, polyoxyethylene alkyl allyl ether, polyoxyethylene fatty acid ester, sorbitan fatty acid ester, polyoxyethylene sorbitan fatty acid ester, polyoxyethylene alkylamine, glycerin fatty acid ester, an oxyethylene oxypropylene block copolymer, an acetylene glycol-based surfactant, and acetylene-based polyoxyethylene oxide. These may be used singly or two or more types can be used.

Specific product names thereof include SUFYNOL 61, 82, 104, 104E, 104H, 104A, 104BC, 104DPM, 104PA, 104PG-50, 104S, 420, 440, 465, 485, 504, CT-111, CT-121, CT-131, CT-136, CT-141, CT-151, CT-171, CT-324, DF-37, DF-58, DF-75, DF-110D, DF-210, GA, OP-340, PSA-204, PSA-216, PSA-336, SE, SE-F, TG, and GA, DYNOL 604 (above, manufactured by Nissin Chemical Co., Ltd. and Air Products and Chemicals, Inc.), OLFINE A, B, AK-02, CT-151W, E1004, E1010, P, SPC, STG, Y, 32W, PD-001, PD-002W, PD-003, PD-004, EXP.4001, EXP.4036, EXP.4051, AF-103, AF-104, SK-14, and AE-3 (above, manufactured by Nissin Chemical Co., Ltd.), and ACETYLENOL E00, E13T, E40, E60, E81, E100, and E200 (all above are product names, manufactured by Kawaken Fine Chemicals Co., Ltd.). Among these, OLFINE E1010 is suitable.

Specific examples of the nonionic surfactant further include nonionic surfactants disclosed in paragraph 0553 of JP2012-208494A ("0679" of corresponding US2012/0235099A), and the contents thereof are incorporated to this specification.

Specific examples of the cation-based surfactant include cation-based surfactants disclosed in paragraph 0554 of JP2012-208494A ("0680" of corresponding US2012/0235099A), and the contents thereof are incorporated to this specification.

Specific examples of the anion-based surfactant include W004, W005, and W017 (manufactured by Yusho Co., Ltd.).

Examples of the silicone-based surfactant include silicone-based surfactants disclosed in paragraph 0556 of JP2012-208494A ("0682" of corresponding US2012/0235099A), and the contents thereof are incorporated to this specification. "TORAY SILICONE SF8410", "TORAY SILICONE SF8427", "TORAY SILICONE SH8400", "ST80PA", "ST83PA", and "ST86PA" manufactured by Dow Corning Corporation, "TSF-400", "TSF-401", "TSF-410", and "TSF-4446" manufactured by Momentive Performance Materials Inc., and "KP321", "KP323", "KP324", and "KP340" manufactured by Shin-Etsu Chemical Co., Ltd.

<<Polymerization Inhibitor>>

In the manufacturing or preservation, the near-infrared ray absorption composition according to the invention may contain a small amount of polymerization inhibitor, in order to preventing unnecessary reaction of the curable compound.

Examples of the polymerization inhibitor include hydroquinone, p-methoxyphenol, di-t-butyl-p-cresol, pyrogallol, t-butylcatechol, benzoquinone, 4,4'-thiobis(3-methyl-6-t-butylphenol), 2,2'-methylenebis(4-methyl-6-t-butylphenol), and N-nitrosophenylhydroxyamine cerous salt, and p-methoxyphenol is preferable.

In a case where the near-infrared ray absorption composition according to the invention contains a polymerization inhibitor, the content of the polymerization inhibitor is preferably 0.01 to 5 mass % with respect to the total solid content of the near-infrared ray absorption composition.

<<Ultraviolet Absorbing Agent>>

The near-infrared ray absorption composition according to the invention may contain an ultraviolet absorbing agent.

The ultraviolet absorbing agent can use well-known compounds. Examples of a commercially available product include UV503 (Daito Chemical Co., Ltd.).

The near-infrared ray absorption composition according to the invention may include or may not include an ultraviolet absorbing agent. However, in a case where near-infrared ray absorption composition according to the invention include an ultraviolet absorbing agent, the content of the ultraviolet absorbing agent is preferably 0.01 to 10 mass % and more preferably 0.01 to 5 mass % with respect to a total solid content of the near-infrared ray absorption composition.

According to the invention, one type of the ultraviolet absorbing agent may be used, and two or more types thereof may be used in combination.

<<Infrared Ray Absorption Substance>>

The near-infrared ray absorption composition according to the invention may further include an infrared ray absorption substance having a maximum absorption wavelength in a near infrared ray range different from a maximum absorption wavelength of the compound represented by Formula (1). According to the embodiment, it is possible to obtain the near-infrared ray absorption filter that can absorb light in a near infrared ray range with a wider wavelength range than light that can be cut only by the compound represented by Formula (1).

Examples of the infrared ray absorption substance include a pyrrolopyrrole coloring agent compound, a copper compound, a cyanine-based coloring agent compound, a phthalocyanine-based compound, an iminium-based compound, a thiol complex-based compound, a transition metal oxide-based compound, a squarylium-based coloring agent compound, a naphthalocyanine-based coloring agent compound, a quaterrylene-based coloring agent compound, a dithiol-metal complex-based coloring agent compound, and a croconium compound.

The pyrrolopyrrole coloring agent compound may be a pigment or may be a dye. However, for the reason that a coloring composition that allows to easily form a film having excellent heat resistance, a pigment is preferable.

Examples of the pyrrolopyrrole coloring agent compound include pyrrolopyrrole compounds disclosed in paragraphs 0016 to 0058 of JP2009-263614A.

As a phthalocyanine-based compound, a naphthalocyanine compound, an iminium-based compound, a cyanine-based coloring agent, a squarylium-based coloring agent, and a croconium compound, compounds disclosed in paragraphs 0010 to 0081 of JP2010-111750A may be used, and the contents thereof are incorporated to this specification. As the cyanine-based coloring agent, for example, "Functional coloring agent, written by Okawara Shin, Matsuoka Ken, Kitao Teijirou, and Hirashima Kousuke, published by Kodansha Scientific Ltd." can be referred to, and the contents thereof are incorporated to this specification.

As a copper compound, copper compounds of paragraphs 0013 to 0056 of JP2014-41318A and paragraphs 0012 to 0030 of JP2014-32380A may be used, and the contents thereof are incorporated to this specification.

Compounds disclosed in paragraphs 0004 to 0016 of JP1995-164729A (JP-H07-164729A), compounds disclosed in paragraphs 0027 to 0062 of JP2002-146254A, and near-infrared ray absorption particles that are disclosed in paragraphs 0034 to 0067 of JP2011-164583A, that consist of crystallites of oxide including Cu and/or P, and that have a number-average aggregate particle diameter of 5 to 200 nm may be used, and the contents thereof are incorporated to this specification.

As a commercially available product, "IRA842" manufactured by Exciton, "FD-25" manufactured by Yamada Kagaku Co., Ltd., and the like can be used.

<<Other Components>>

Examples of other components that can be used together in the near-infrared ray absorption composition according to the invention include a dispersing agent, a sensitizing agent, a crosslinking agent, a hardening accelerator, a filler, a thermal hardening accelerator, a thermal polymerization inhibitor, and a plasticizers, and an adhesion promoter to a substrate surface and other auxiliary agents (for example, a conductive particle, a filler, an antifoaming agent, a flame retardant, a leveling agent, a peeling promoter, an antioxidant, a fragrance material, a surface tension adjuster, and a chain transfer agent) may be used together.

If these components are appropriately contained, it is possible to adjust desired characteristics such as stability of the near-infrared ray absorption filter and film properties.

As these components, for example, disclosure in paragraphs 0183 to 0228 of JP2012-003225A ("0237" to "0309" of corresponding US2013/0034812A), paragraphs 0101 and 0102, paragraphs 0103 and 0104, and paragraphs 0107 to 0109 of JP2008-250074A, and paragraphs 0159 to 0184 of JP2013-195480A can be referred to, and the contents thereof are incorporated to this specification.

<Preparation and Use of Near-Infrared Ray Absorption Composition>

The near-infrared ray absorption composition according to the invention can be prepared by mixing the respective components described above.

In a case where the near-infrared ray absorption filter is formed by coating, the viscosity of the near-infrared ray absorption composition according to the invention is preferably in the range of 1 to 3,000 mPa·s. The lower limit is preferably 10 mPa·s or greater and more preferably 100 mPa·s or greater. The upper limit is preferably 2,000 mPa·s or less, and more preferably 1,500 mPa·s or less.

The use of the near-infrared ray absorption composition according to the invention is not particularly limited, and the near-infrared ray absorption composition can be used in a near-infrared ray absorption filter or the like. For example, it is possible to form a near-infrared ray absorption filter of an infrared sensor that detects an object by detecting light in wavelengths of 900 nm to 1,000 nm. The near-infrared ray absorption composition can be used in a near-infrared ray absorption filter (for example, a near-infrared ray absorption filter for a wafer level lens) on a light receiving side of a solid-state imaging device, a near-infrared ray absorption filter on a back surface side (an opposite side of a light receiving side) of a solid-state imaging device, and the like.

The near-infrared ray absorption composition according to the invention may be used by directly coating an image sensor with the near-infrared ray absorption composition so as to form a coated film.

Since the near-infrared ray absorption composition according to the invention can be supplied in a coatable state, a near-infrared ray absorption filter can be easily formed on a desired member or a desired position of a solid-state imaging device.

<Near-Infrared Ray Absorption Filter>

Subsequently, the near-infrared ray absorption filter according to the invention is described.

The near-infrared ray absorption filter according to the invention may be formed by hardening the near-infrared ray absorption composition according to the invention.

With respect to the near-infrared ray absorption filter according to the invention, light transmittance preferably satisfies at least one of condition (1), condition (2), condition (3), condition (4), condition (5), condition (6), or (7) below and further preferably satisfies all the conditions (1) to (7).

(1) The light transmittance in a wavelength of 400 nm is preferably 80% or greater, more preferably 85% or greater, and particularly preferably 90% or greater.

(2) The light transmittance in a wavelength of 500 nm is preferably 80% or greater, more preferably 85% or greater, and particularly preferably 90% or greater.

(3) The light transmittance in a wavelength of 600 nm is preferably 80% or greater, more preferably 85% or greater, and particularly preferably 90% or greater.

(4) The light transmittance in a wavelength of 700 nm is preferably 80% or greater, more preferably 85% or greater, and particularly preferably 90% or greater.

(5) The light transmittance in a wavelength of 750 nm is preferably 80% or greater, more preferably 85% or greater, and particularly preferably 90% or greater.

(6) The light transmittance in a wavelength of 800 nm is preferably 65% or greater, more preferably 75% or greater, and particularly preferably 80% or greater.

(7) The light transmittance in a wavelength of 900 nm is preferably 70% or less, more preferably 65% or less, and particularly preferably 60% or less.

A film thickness of a near-infrared ray absorption filter can be appropriately selected depending on purposes, preferably 20 μm or less, more preferably 10 μm or less, and further preferably 5 μm or less. For example, the lower limit of the film thickness is preferably 0.1 μm or greater, more preferably 0.2 μm or greater, and further preferably 0.3 μm or greater. According to the invention, the near-infrared ray absorption filter has high near infrared ray shielding properties, and thus the film thickness of the near-infrared ray absorption filter can be caused to be thin.

With respect to the near-infrared ray absorption filter, visible light transmittance in a total wavelength range of 400 to 700 nm is preferably 85% or greater and more preferably 90% or greater, in a film thickness of 20 μm or less. It is preferable that light transmittance at least one point in a wavelength range of 900 nm to 1,000 nm is 20% or less. According to the invention, it is possible to widely secure a visible light area with high transmittance and to provide a near-infrared ray absorption filter having high near infrared ray shielding properties.

<Method for Manufacturing Near-Infrared Ray Absorption Filter>

The near-infrared ray absorption filter can be manufactured by a step of forming a film by applying (preferably, a dropwise addition method, coating, or printing) the near-infrared ray absorption composition according to the invention to a support and a step of drying a film. A film thickness and a laminate structure can be appropriately selected depending on purposes. A step of forming a pattern may be performed.

A step of forming a film can be performed, by using the near-infrared ray absorption composition according to the invention on a support by a dropwise addition method (drop cast), a spin coater, a slit spin coater, a slit coater, screen printing, applicator coating, and the like. In a case of a dropwise addition method (drop cast), it is preferable to form a dropwise addition area of a composition having a photoresist as a partition wall on a support such that an even film in a predetermined film thickness can be obtained. The film thickness can be adjusted by a dropwise addition amount of a composition, a concentration of a solid content, and a size of the dropwise addition area.

The support to which the near-infrared ray absorption composition according to the invention is applied may be a transparent substrate consisting of glass or the like. The support may be a solid-state imaging device, may be another substrate provided on a light receiving side of the solid-state imaging device, and may be a layer such as a planarizing layer or the like provided on a light receiving side of the solid-state imaging device. For example, the planarizing layer may be a transparent planarizing layer made of an acrylic resin or the like.

In a step of drying a film, though the dry condition is different depending on respective components, types of solvents, use ratio, and the like, the dry condition is in a temperature of 60° C. to 150° C. for about 30 seconds to 15 minutes.

Examples of the step of forming a pattern include methods including a step of forming a film-shaped composition layer obtained by applying the near-infrared ray absorption composition according to the invention on the support, a step of exposing the composition layer in a pattern shape, and a step of forming a pattern by developing and removing unexposed parts, and the like. As a step of forming a pattern, photolithography or a dry etching method may be used for forming a pattern.

In the method for manufacturing a near infrared ray filter, other steps may be included. The other steps are not particularly limited, and can be appropriately selected depending on purposes. Examples thereof include a step of treating a surface of a substrate, a preheating step (prebaking step), a hardening treatment step, and a post heating step (post baking step).

<<Preheating Step and Post Heating Step>>

The heating temperature in the preheating step and post heating step is generally 80° C. to 200° C. and preferably 90° C. to 150° C. The heating time in the preheating step and the post heating step is generally 30 seconds to 240 seconds and preferably 60 seconds to 180 seconds.

<<Hardening Treatment Step>>

A hardening treatment step is a step of performing a hardening treatment on a formed film, if necessary. If this treatment is performed, mechanical strength of the near-infrared ray absorption filter is improved.

The hardening treatment step is not particularly limited, and can be appropriately selected depending on purposes. Examples thereof suitably include an entire surface exposure treatment and an entire surface heating treatment. Here, the expression "exposure" according to the invention is used as a meaning of including not only light in various wavelengths but also radioactive ray irradiation such as electron rays or X rays.

The exposure is preferably performed by irradiation of radioactive rays. As the radioactive that can be used at the time of exposure, particularly, electron rays, KrF, ArF, ultraviolet rays such as g rays, h rays, and i rays, or visible light are preferably used.

Examples of an exposure technique include stepper exposure or exposure by a high pressure mercury vapor lamp. An exposure amount is preferably 5 to 3,000 mJ/cm$^2$, more preferably 10 to 2,000 mJ/cm$^2$, and particularly preferably 50 to 1,000 mJ/cm$^2$.

Examples of the entire surface exposure treatment include a method for exposing an entire surface of the formed film. In a case where the composition according to the invention contains a polymerizable compound, hardening of the polymerizable compounds in the film is promoted by the entire surface exposure, such that hardening of the film further proceeds, and mechanical strength and durability further improve.

A device for performing the entire surface exposure is not particularly limited, and can be appropriately selected depending on purposes, and examples thereof suitably include a UV exposure machine such as a high pressure mercury vapor lamp.

Examples of the entire surface heating treatment method include a method for heating the entire surface of the formed film. With the heating of the entire surface, the film hardness of the pattern can be increased.

The heating temperature of the heating of the entire surface is preferably 120° C. to 250° C. and more preferably 160° C. to 220° C. If the heating temperature is 120° C. or greater, the film hardness improves by a heating treatment. If the heating temperature is 250° C. or less, the decomposition of the film component is suppressed.

The heating time for the heating of the entire surface is preferably 3 minutes to 180 minutes and more preferably 5 minutes to 120 minutes.

A device for heating the entire surface is not particularly limited, and can be appropriately selected among well-known devices, depending on purposes. Examples thereof include a dry oven, a hot plate, and an IR heater.

<Use of Near-Infrared Ray Absorption Filter>

The near-infrared ray absorption filter according to the invention is used for lenses having a function of absorbing or cutting near infrared rays (camera lens such as a digital camera, a cellular phone, or a vehicle camera, optical lenses such as f-θ lenses or pickup lenses), an optical filter for a semiconductor light-receiving element, a near-infrared absorbing film and or a near-infrared absorbing plate that cut off heat rays for energy saving, an agricultural coating agent for the purpose of selective use of sunlight, a recording medium that uses near-infrared absorption heat, a near-infrared filter for electronic devices or photos, protection glasses, sunglasses, a heat ray cut-off film, an optical character reading record, a use for confidential document copy preventing media, an electrophotographic photoreceptor, and laser welding. The near-infrared ray absorption filter is also useful for a noise cut filter for a CCD camera and a filter for a CMOS image sensor.

The near-infrared ray absorption filter according to the invention can use in combination with a bandpass filter. The spectral characteristics of a bandpass filter can be appropriately selected depending on a wavelength of a light source, spectral characteristics of the near-infrared ray absorption filter, and the like. If the near-infrared ray absorption filter is used in combination of a bandpass filter, it is possible to shield near infrared rays of the area with a wide width can be protected.

If the near-infrared ray absorption filter according to the invention and an infrared ray transmission filter described below are combined to be used, the combination can be preferably used for the use of an infrared sensor that detects near infrared rays in a specific wavelength described below. A bandpass filter may be further combined thereto. For example, light in wavelengths of 900 nm to 1,000 nm can be accurately detected, for example, by using a light source that has a light emitting wavelength of 950 nm, using an infrared ray transmission filter that shields visible light (light in wavelengths of 400 to 700 nm) and transmits light having wavelengths of 900 nm or longer, and using a near-infrared ray absorption filter that shields visible light (light in wavelengths of 400 to 700 nm) and transmits light in wavelengths of 900 nm or longer. Light in wavelengths of 900 nm to 1,000 nm can be accurately detected by further combining a bandpass filter of transmitting visible light (light in wavelengths of 400 to 700 nm) and shielding light in wavelengths of 970 nm or longer (preferably light in wavelengths of 1,000 nm or longer).

Examples of the bandpass filter include a laminate that has a first area (hereinafter, also referred to as a "high refractive area") and a second area (hereinafter, also referred to as a "low refractive area") and has the high refractive area and the low refractive area alternately laminated.

Figure 4:
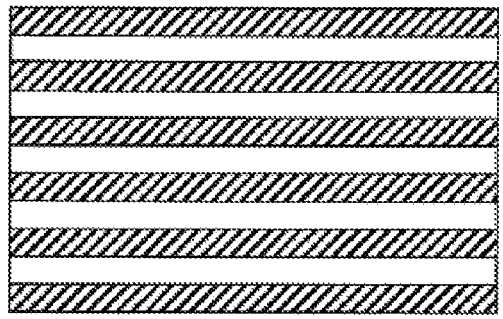
FIG. 4 is a cross-sectional view schematically illustrating an example of a configuration of a bandpass filter.

FIG. 4 is a diagram schematically illustrating an example of a configuration of the bandpass filter and high refractive areas (layers shown by diagonal lines) and low refractive areas (layers shown by a white color) alternately laminated. Optical paths of light are adjusted by adjusting thicknesses of the high refractive area and the low refractive area, such that transmittance depending on a desired wavelength is controlled. In FIG. 4, thicknesses of the high refractive area and the low refractive area are caused to be substantially the same but may be different from each other. The high refractive areas and the low refractive area may be each independently represent one high refractive layer or one low refractive layer or may be formed with two or more high refractive layers or two or more low refractive layers.

Figure 5:
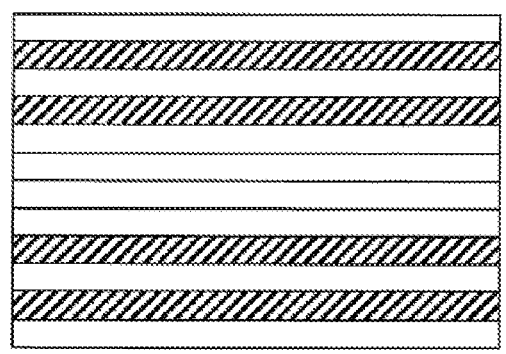
FIG. 5 is a cross-sectional view schematically illustrating another example of a configuration of the bandpass filter.

FIG. 5 is a cross-sectional view schematically another example of a configuration of the bandpass filter and shows a configuration in which thicknesses of respective high refractive areas (layers shown by a white color) are different from each other. In this manner, it becomes possible to transmit only light in a specific wavelength by providing areas having different thicknesses in plural high refractive areas. In a case where the high refractive area consists of two or more high refractive layers, the upper limit of the number of high refractive layers that form one high refractive area is, for example, 8 layers or less and further 6 layers or less. The thickness of the high refractive area can be adjusted by adjusting the thickness of the coated film. FIG. 5 illustrates a configuration in which thicknesses of the respective high refractive areas are different, but it is obvious that FIG. 5 may illustrate a configuration in which the thicknesses of the respective low refractive areas are different from each other. In this case, details of the low refractive area may be the same as the details of the high refractive area. Both of the high refractive area and the low refractive area may have different configuration s from each other.

The alternate lamination according to the invention refers to a configuration in which low refractive areas and high refractive areas are laminated on the film by turns, but the lamination does not have to be a laminate only with the low refractive areas and the high refractive areas. For example, a third area having a refractive index different from the first area and the second area such as a medium refractive area may be provided between the low refractive areas and the high refractive areas.

The low refractive area and the high refractive area of the bandpass filter may be provided on the substrate.

The substrate may be a transparent substrate such as a glass, may be a solid-state imaging device substrate, may be another substrate (for example, a glass substrate and a plastic substrate) provided on a light receiving side of the solid-state imaging device substrate, or may be a planarizing layer provided on a light receiving side of the solid-state imaging device substrate.

A difference between refractive indexes of the high refractive area and the low refractive area is preferably 0.5 or greater, is more preferably 0.55 or greater, can be 0.6 or greater, and can be 0.65 or greater. Examples of the upper limit of the difference between the refractive indexes of the high refractive area and the low refractive area can be, for example, 0.8 or less and can be 0.75 or less.

The high refractive area and the low refractive area of the bandpass filter can be formed by vapor deposition but are preferably formed by a coating method. If the high refractive area and the low refractive area are formed by the coating method, a bandpass filter can be manufactured simply and with a low cost. In a case where the high refractive area and/or the low refractive area is formed by the coating method, examples thereof include a method for forming the high refractive area and/or the low refractive area by using the composition including the resin. Hereinafter, a bandpass filter is described.

<<First Area (High Refractive Area)>>

A refractive index of the first area of the bandpass filter according to the invention is preferably higher than that of a second area described below, by 0.5 or greater. The refractive index of the high refractive area is preferably 1.5 to 3.0 and more preferably 1.7 to 2.3.

The first area is preferably a layer including a resin. The layer including a resin may be a layer including a so-called high refractive resin and may be formed by applying the composition (hereinafter, also referred to as a "high refractive composition") including a resin, particles, and a solvent. The resin used for forming the first area is preferably a polymer chain consisting of a repeating unit derived from a polymerizable monomer or a compound having a polymer chain consisting of a repeating unit derived from a polymerizable monomer as a partial structure. Preferably, the resin is a layer obtained by applying a high refractive composition.

Hereinafter, details of the high refractive composition are described.

<<<High Refractive Composition>>>
<<<Resin>>>

Examples of a resin included in the high refractive composition include a resin in which particles described below can be dispersed. Specifically, embodiments below are exemplified.

A first embodiment is a resin including a group selected from an acid group, a group having a basic nitrogen atom, a urea group, a urethane group, a group having a coordinating oxygen atom, an alkyloxycarbonyl group, an alkylaminocarbonyl group, a carboxylic acid base, a sulfonamide group, an alkoxysilyl group, an epoxy group, an isocyanate group, and a hydroxyl group.

Examples of the acid group include a carboxylic acid group, a sulfonic acid group, a phosphoric acid group, and a phenolic hydroxyl group. One group selected from a carboxylic acid group, a sulfonic acid group, and a phosphoric acid group is preferable, and a carboxylic acid group is particularly preferable.

The acid value is preferably 20 to 300 mgKOH/g, more preferably 50 to 250 mgKOH/g, and further preferably 50 to 210 mgKOH/g.

The resin is more preferably a resin represented by Formula (1).

   Formula (1)

In Formula (1), $R^1$ represents a (m+n)-valent linking group, and $R^2$ represents a single bond or a divalent linking group. $A^1$ represents a monovalent substituent having at least one group selected from an acid group, a urea group, a urethane group, a group having a coordinating oxygen atom, a group having a basic nitrogen atom, a phenol group, an alkyl group, an aryl group, a group having an alkyleneoxy chain, an imido group, a heterocyclic group, an alkyloxycarbonyl group, an alkylaminocarbonyl group, a carboxylic acid base, a sulfonamide group, an alkoxysilyl group, an epoxy group, an isocyanate group, and a hydroxyl group. n items of $A^1$ and $R^2$ may respectively identical to or different from each other. m represents a positive number of 8 or less, n represents 1 to 9, and m+n satisfies 3 to 10. $P^1$ represents a polymer chain. m items of $P^1$ may be identical to or different from each other.

With respect to details of the resins represented by Formula (1), disclosure in paragraphs 0022 to 0076 of JP2014- 177613A and paragraphs 0020 to 0074 of JP2014-62221A can be referred to, and the contents thereof are incorporated to this specification.

A second embodiment is a resin including a graft copolymer.

The number of atoms of the graft copolymer except for hydrogen atoms for one graft chain is preferably 40 to 10,000, more preferably 100 to 500, and further preferably 150 to 260.

As a polymer structure of a graft chain is a poly(meth)acryl structure, a polyester structure, a polyurethane structure, a polyurea structure, a polyamide structure, a polyether structure, and the like can be used.

With respect to the resin including the graft copolymer, disclosure in paragraphs 0080 to 0126 disclosed in JP2014-063125A can be referred to, and the contents thereof are incorporated to this specification.

The third embodiment is an oligoimine-based resin including nitrogen atom on at least one side of a main chain or a side chain. As the oligoimine-based resin, a resin that has a repeating unit having a partial structure X having a functional group with pKa 14 or less and a side chain including a side chain Y having atoms of 40 to 10,000 and that has basic nitrogen atoms on at least one of a main chain or a side chain is preferable.

With respect to the oligoimine-based resin, for example, disclosure in paragraphs 0225 to 0267 of JP2014-063125A can be referred to, and the contents thereof are incorporated to this specification.

A fourth embodiment is a siloxane resin obtained by hydrolyzing a silane compound including a silane compound represented by any one of Formulae (2) to (4) and performing condensation reaction on this hydrolysate.

   Formula (2)

In Formula (2), $R^0$ represents a hydrogen, an alkyl group, an alkenyl group, or a phenyl group. $R^1$ represents a monovalent condensed polycyclic aromatic group. $R^9$ represents a hydrogen, a methyl group, an ethyl group, a propyl group, or a butyl group and may be identical or different from each other, n represents 1 or 2. In a case where n is 2, plural $R^1$'s may be identical or different from each other.

   Formula (3)

In Formula (3), $R^2$ represents a monovalent condensed polycyclic aromatic group. $R^{10}$ represents a hydrogen, a methyl group, an ethyl group, a propyl group, or a butyl group, and may be identical to or different from each other.

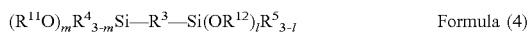   Formula (4)

In Formula (4), $R^3$ represents a divalent condensed polycyclic aromatic group. $R^4$ and $R^5$ represent a hydrogen, an alkyl group, an alkenyl group, and an aryl group, and may be identical to or different from each other. $R^{11}$ and $R^{12}$ represent a hydrogen, a methyl group, an ethyl group, a propyl group, or a butyl group, and may be identical to or different from each other. m and l each independently represent an integer of 1 to 3.

With respect to the siloxane resins, for example, disclosure in paragraphs 0017 to 0044 of JP2010-007057A can be referred to, and the contents thereof are incorporated to this specification.

The high refractive composition preferably includes an epoxy resin. Examples of the epoxy resin include EX211L (manufactured by Nagase ChemteX Corporation) and JER157S65 (manufactured by Mitsubishi Chemical Corporation).

The molecular weight of the resin is preferably 2,000 to 200,000, more preferably 2,000 to 15,000, and further preferably 2,500 to 10,000 by a weight-average molecular weight.

The amount of the resin in the high refractive composition is preferably 0.5 mass % or greater, more preferably 1 mass % or greater, and further preferably 2 mass % or greater. The upper limit is preferably 30 mass % or less, more preferably 20 mass % or less, and further preferably 15 mass % or less.

The concentration of the solid content of the resin in the high refractive composition is preferably 5 mass % or greater, more preferably 8 mass % or greater, and further preferably 10 mass % or greater. The upper limit is preferably 40 mass % or less, more preferably 35 mass % or less, and further preferably 30 mass % or less.

Only one type of the resin may be included, and two or more types thereof may be included. In a case where two or more types thereof are included, it is preferable that a total amount is in the range described above.

<<<Particles>>>

The particles included in the high refractive composition preferably include metal oxide particles.

The metal oxide particles are preferably colorless, white, or transparent inorganic particles having a high refractive index, examples thereof include oxide particles of titanium (Ti), zirconium (Zr), aluminum (Al), silicon (Si), zinc (Zn), or magnesium (Mg), titanium dioxide ($TiO_2$) particles, zirconium dioxide ($ZrO_2$) particles are preferable, and titanium dioxide particles more preferable.

With respect to the metal oxide particles, a lower limit of a primary particle diameter is preferably 1 nm or longer, and an upper limit is preferably 100 nm or less, more preferably 80 nm or less, and further preferably 50 nm or less. As an index of the primary particle diameter, an average particle diameter can be used. The average particle diameter of the metal oxide particles refers to a value obtained by diluting mixture liquid or dispersion liquid including metal oxide particles to 80 times with propylene glycol monomethyl ether acetate and measuring the obtained diluent by a dynamic light scattering method. This measurement is performed as a number-average particle diameter obtained by using MICROTRAC UPA-EX150 manufactured by Nikkiso Co., Ltd.

With respect to the metal oxide particles, disclosure in paragraphs 0023 to 0027 of JP2014-062221A is referred to, and the contents thereof are incorporated to this specification.

The amount of the particles in the high refractive composition is preferably 10 mass % or greater, more preferably 15 mass % or greater, and further preferably 20 mass % or greater. The upper limit is not particularly limited, but preferably 40 mass % or less and more preferably 30 mass % or less.

The concentration of the solid content of the particles in the high refractive composition is preferably 60 mass % or greater and more preferably 70 mass % or greater. The upper limit is not particularly limited, but preferably 99 mass % or less, more preferably 95 mass % or less, and further preferably 90 mass % or less.

Only one type of particles may be included, and two or more types thereof may be included. In a case where two or more types thereof are included, it is preferable that a total amount is in the range described above.

<<<Solvent>>>

Examples of the solvent included in the high refractive composition include the solvents described in the near-infrared ray absorption composition above. Preferable examples thereof include methyl 3-ethoxypropionate, ethyl 3-ethoxypropionate, ethyl cellosolve acetate, ethyl lactate, diethylene glycol dimethyl ether, butyl acetate, methyl 3-methoxypropionate, 2-heptanone, cyclohexanone, ethyl carbitol acetate, butyl carbitol acetate, propylene glycol methyl ether, dipropylene glycol dimethyl ether, propylene glycol mono-n-butyl ether, propylene glycol monotert-butyl ether, and propylene glycol methyl ether acetate.

With respect to other solvents included in the high refractive composition, for example, disclosure in paragraphs 0065 to 0067 of JP2014-063125A can be referred to, and the contents thereof are incorporated to this specification.

The amount of the solvent in the high refractive composition is preferably 50 mass % or greater and more preferably 60 mass % or greater in the total amount of the composition. In the total amount of the composition, the upper limit is preferably 99.9 mass % or less, more preferably 95 mass % or less, and further preferably 90 mass % or less.

Only one type of the solvent may be included, and two or more types thereof may be included. In a case where two or more types thereof are included, the total amount is in the range described above.

<<<Surfactant>>>

In view of improving coating properties, the high refractive composition may contain a surfactant. Examples of the surfactant include surfactants described in the near-infrared ray absorption composition above. Among them, a fluorine-based surfactant is preferable. In a case where a film is formed by using a coating liquid to which a composition containing a fluorine-based surfactant is applied, interfacial tension between the coated surface and the coating liquid is reduced such that wettability to the coated surface is improved, and thus the coating properties to the coated surface is improved. Therefore, a film that has small thickness unevenness and has a homogeneous thickness can be more suitably formed.

Only one type of the surfactant may be used, and two or more types thereof may be used in combination.

The content of the surfactant is preferably 0.001 to 2.0 mass % and more preferably 0.005 to 1.0 mass % with respect to the total mass of the composition.

<<Polymerization Inhibitor>>

The high refractive composition may contain a polymerization inhibitor. Examples of the polymerization inhibitor include a polymerization inhibitor described in the near-infrared ray absorption composition above. The content of the polymerization inhibitor is preferably 0.001 to 5 mass % with respect to the total mass of the composition.

<<<Other Additives>>>

The high refractive composition may include other additives. Specific examples thereof include a hardening agent, a curable compound, a photopolymerization initiator, a resin (for example, an alkali soluble resin and a binder) other than the resins above, a plasticizer, an oil sensitizing agent, and an ultraviolet absorbing agent. With respect to other additives, disclosure in paragraphs 0133 to 0224 of JP2014-063125A can be referred to, and the contents thereof are incorporated to this specification.

As a curable compound, a photopolymerization initiator, and an alkali soluble resin, those described in the near-infrared ray absorption composition above can be used.

<<Specific Examples of High Refractive Composition>>

As the specific examples of the high refractive composition, dispersion compositions disclosed in Claim 1 of JP2014-062221A and siloxane-based resin compositions disclosed in Claim 1 of JP2010-007057A can be exemplified, and the contents thereof are incorporated to this specification. Preferable ranges of these compositions are provided as examples of preferable ranges of the high refractive composition according to the invention.

<<Film Thickness>>

The film thickness of the high refractive area is appropriately determined so as to achieve a desired optical path of light. For example, the film thickness is 80 nm or longer, can be 100 nm or longer, and can be 120 nm or longer. For example, the upper limit is 600 nm or less, can be 500 nm or less, and can be 300 nm or less.

<Second Area (Low Refractive Layer)>

The second area according to the invention is preferably an area having a lower refractive index by 0.5 or greater than the first area. The refractive index of the low refractive area is more preferably 1.0 to 1.5 and even more preferably 1.1 to 1.5.

The second area is preferably a layer including a resin. The layer including a resin may be a layer consisting of a so-called low refractive resin, that is, a resin having a lower refractive index than the high refractive resin above and may be formed by applying a composition (hereinafter, also referred to as a "low refractive composition") including a resin, particles, and a solvent. The resin used for forming the second area is preferably a compound having a polymer chain consisting of a repeating unit derived from a polymerizable monomer or a polymer chain consisting of a repeating unit derived from a polymerizable monomer as a partial structure. Preferably, the second area is a layer obtained by applying a low refractive composition.

Hereinafter, details of the low refractive composition are described.

<<Low Refractive Composition>>

<<<Resin>>>

As the resin used in the low refractive area, a resin including at least one of a siloxane resin or a fluorine-based resin is exemplified.

<<<<Siloxane Resin>>>>

The siloxane resin can be obtained by using an alkoxysilane raw material via hydrolysis reaction and condensation reaction. Specifically, the siloxane resin is a resin in which a portion or all of alkoxy groups in alkyl trialkoxysilane is hydrolyzed and converted to silanol groups, and at least a portion of the generated silanol groups is condensed to form Si—O—Si bonds. The siloxane resin is preferably a resin having a silsesquioxane structure represented by Formula (5) below.

  Formula (5)

In Formula (5), $R^1$ represents an alkyl group having 1 to 3 carbon atoms. n represents an integer of 20 to 1,000.

<<<<Fluorine-Based Resin>>>>

The fluorine-based resin is a resin containing fluorine in a substance molecule, and specific examples thereof include polytetrafluoroethylene, polyhexafluoropropylene, a tetrafluoroethylene/hexafluoropropylene copolymer, a tetrafluoroethylene/perfluoroalkyl vinyl ether copolymer, a tetrafluoroethylene/ethylene copolymer, a hexafluoropropylene/propylene copolymer, polyvinylidene fluoride, and a vinylidene fluoride/ethylene copolymer.

For example, with respect to details of the siloxane resin and fluorine-based resin, for example, disclosure in paragraphs 0014 to 0060 of JP2014-063125A can be referred to, and the contents thereof are incorporated to this specification.

According to the invention, with respect to the resins included in the low refractive composition, hydrolysates by predetermined silicon compounds disclosed in paragraphs 0016 to 0024 of JP2013-253145A and compounds disclosed in paragraphs 0030 to 0043 of JP2012-0214772A are referred to, and the contents thereof are incorporated to this specification.

The content of the resin in the low refractive composition is preferably 0.5 mass % or greater, more preferably 1 mass % or greater, and further preferably 2 mass % or greater. The upper limit is preferably 30 mass % or less, more preferably 20 mass % or less, and further preferably 15 mass % or less.

The concentration of the solid content of the resin in the low refractive composition is preferably 5 mass % or greater, more preferably 8 mass % or greater, and further preferably 10 mass % or greater. The upper limit is preferably 40 mass % or less, more preferably 35 mass % or less, and further preferably 30 mass % or less.

Only one type of the resin may be included, or two or more types thereof may be included. In a case where two or more types thereof are included, it is preferable that a total amount is in the range described above.

<<<Particles>>>

Examples of the particles used in the low refractive area include hollow particles or non-hollow particles. As the hollow particles, particles in a hollow structure or porous fine particles may be used. The hollow particles are particles in a structure of having hollows inside, and refer to particles having surrounded hollows on outer shells, and the porous particles refer to porous particles having a large number of hollows. Hereinafter, the hollow particles or the porous particles are appropriately referred to as "specific particles". The specific particles may be organic particles or may be inorganic particles. The particles are preferably metal oxide particles and more preferably silica particles.

With respect to the particles used in the low refractive area, for example, disclosure in paragraphs 0047 to 0055 of JP2014-063125A is referred to, and the contents thereof are incorporated to this specification.

The content of the particles in the low refractive composition is preferably 10 mass % or greater, more preferably 15 mass % or greater, and further preferably 20 mass % greater. The upper limit is not particularly limited, but preferably 40 mass % or less and more preferably 30 mass % or less.

The concentration of the solid content of the particles in the low refractive composition is preferably 60 mass % greater and more preferably 70 mass % greater. The upper limit is not particularly limited, but preferably 99 mass % or less, more preferably 95 mass % or less, and further preferably 90 mass % or less.

Only one type of the particles may be included, and two or more types thereof may be included. In a case where two or more types thereof are included, it is preferable that a total amount is in the range described above.

<<<Solvent>>>

The solvent included in the low refractive composition is the same as the solvent included in the high refractive composition, and preferable ranges and formulation amounts thereof are also the same.

<<<Other Additives>>>

The low refractive composition used in the invention may include other additives.

Other additives are as described in the high refractive composition above and formulation amounts are also the same.

<<Specific Examples of Low Refractive Composition>>

As specific examples of the low refractive composition, curable compositions for forming a low refractive film disclosed in Claims 11 of JP2014-063125A and compositions disclosed in Claim 1 and paragraphs 0016 to 0028 of JP2013-253145A are exemplified, and the contents thereof are incorporated to this specification.

<<Film Thickness>>

The film thickness of the low refractive area is appropriately determined so as to achieve a desired optical path of light, but for example, the film thickness is 80 nm or longer, can be 100 nm or longer, and can be 120 nm or longer. For example, the upper limit is 600 nm or less, can be 500 nm or less, and can be 300 nm or less.

<Method for Manufacturing Bandpass Filter>

The bandpass filter is manufactured by respectively applying the high refractive composition described above and the low refractive composition described above and forming the high refractive area and the low refractive area.

In a case where a high refractive area consists of one high refractive layer, a step of forming a high refractive area by applying a high refractive composition, the number of times of coating is generally one time, but two or more high refractive layers may be formed by simultaneously or sequentially applying a high refractive layer. The coating method according to the invention is not particularly limited, but a well-known coating method can be appropriately applied. For example, a spraying method, a roll coating method, a rotation coating method (spin coating method), and a bar coating method can be applied. For example, in a case of spin coating, coating time for each high refractive layer can be 30 seconds to 3 minutes, and can be also 30 seconds to 2 minutes.

With respect to a coating amount, coating is preferably performed such that a film thickness after hardening becomes in a desired condition.

If necessary, a heating treatment or the like is preferably performed on the coated film, so as to remove a solvent included in the coated film. Specifically, it is preferable that post baking is performed after coating, so as to a portion or all of the solvent is volatilized. The post baking on the high refractive area is preferably performed at 100° C. to 300° C. for 30 seconds to 8 minutes, and more preferably performed at 150° C. to 250° C. for 1 to 5 minutes.

For the purpose of removing foreign substances or decreasing defects, the high refractive composition is preferably filtrated before coating. Anything that used for a filter in the related art can be used without limitation.

After the high refractive area is formed, a low refractive area is formed on the surface thereof by applying the low refractive composition. The low refractive area is formed in the same manner as the forming of the high refractive area, except for changing the high refractive composition to the low refractive composition, and the preferable range thereof is also the same. However, the post baking of the low refractive area is preferably performed at 80° C. to 240° C. for 30 seconds to 8 minutes and more preferably performed at 80° C. to 120° C. for 1 to 5 minutes.

A laminate (bandpass filter) can be obtained by alternately laminating the high refractive areas and the low refractive areas.

<Infrared Sensor>

The infrared sensor according to the invention has an infrared ray transmission filter and a near-infrared ray absorption filter and detects an object by detecting light in wavelengths of 900 nm to 1,000 nm, and a near-infrared ray absorption filter contains a near-infrared ray absorption substance having a maximum absorption wavelength in wavelengths of 900 nm to 1,000 nm.

In the infrared sensor according to the invention, since the near-infrared ray absorption filter contains the near-infrared ray absorption substance having a maximum absorption wavelength in wavelengths of 900 nm to 1,000 nm, light derived from visible light can be effectively shielded with the near-infrared ray absorption filter. Therefore, it is possible to obtain an infrared sensor having satisfactory sensor sensitivity, excellent detectability, and an excellent image quality.

Hereinafter, one embodiment of the infrared sensor according to the invention is described by using FIG. 1.

In an infrared sensor 100 illustrated in FIG. 1, a reference numeral 110 is a solid-state imaging device.

An image pick-up area provided on the solid-state imaging device 110 has near-infrared ray absorption filters 111 and color filters 112.

Areas 114 are provided between infrared ray transmission filters 113 and the solid-state imaging device 110. Resin layers (for example, transparent resin layers) that light in a wavelength that transmits the infrared ray transmission filters 113 transmits are provided on the areas 114. According to the embodiment illustrated in FIG. 1, resin layers are provided on the areas 114, but the infrared ray transmission filters 113 are formed on the areas 114. That is, the infrared ray transmission filters 113 may be formed on the solid-state imaging device 110.

Microlenses 115 are provided on incidence rays hv side of the color filters 112 and the infrared ray transmission filters 113. A planarizing layer 116 is formed so as to cover the microlenses 115.

According to the embodiment illustrated in FIG. 1, film thicknesses of the color filters 112 and film thicknesses of the infrared ray transmission filters 113 are the same, but film thicknesses of the both may be different from each other.

According to one embodiment illustrated in FIG. 1, the color filters 112 are provided to be closer to the incidence rays hv than the near-infrared ray absorption filters 111, but the near-infrared ray absorption filters 111 may be provided to be closer to the incidence rays hv side than the color filters 112 by changing an order of the near-infrared ray absorption filters 111 and the color filters 112.

According to the embodiment illustrated in FIG. 1, the near-infrared ray absorption filters 111 and the color filters 112 are laminate to be adjacent to each other, but both of the filters do not have to be adjacent to each other and another layer may be interposed therebetween.

According to the embodiment illustrated in FIG. 1, the near-infrared ray absorption filters 111 and the color filters 112 are provided as separate members. However, the color filters 112 may be caused to have near-infrared ray absorption filters by causing the color filters 112 to contain near-infrared ray absorption substances. In this case, the near-infrared ray absorption filters 111 may be omitted.

The infrared sensor according to the invention does not need a near-infrared ray absorption filter as a member of a camera module by including near-infrared ray absorption filters therein, and thus the number of components of the camera module so as to minimize the camera module.

<<Near-Infrared Ray Absorption Filters 111>>

The near-infrared ray absorption filters 111 contain near-infrared ray absorption substances having a maximum absorption wavelength in wavelengths of 900 nm to 1,000 nm. It is preferable that the maximum absorption wavelength of the near-infrared ray absorption substance is substantially the same as a light emitting wavelength of an infrared light emitting diode (LED) used as a light source described below, and the difference of the both are preferably within 20 nm and further preferably within 10 nm. As the near-infrared ray absorption substance, a pyrrolopyrrole compound is preferable, and a quinoxaline-type pyrrolopyrrole compound is more preferable, and the compound represented by Formula (1) above is particularly preferable.

The near-infrared ray absorption filters 111 are preferably filters obtained by hardening the near-infrared ray absorption composition according to the invention. The near-infrared ray absorption filters 111 preferably have optical transmittance which is the same as the near-infrared ray absorption filter described above. The near-infrared ray absorption filters 111 can be manufactured in the same manner as the near-infrared ray absorption filter described above.

<<Color Filters 112>>

The color filters 112 are not particularly limited, and color filters for forming pixels in the related art can be used. For example, disclosure in paragraphs 0214 to 0263 of JP2014-043556A can be referred to, and the contents thereof are incorporated to this specification.

<Infrared Ray Transmission Filters 113>

Characteristics of the infrared ray transmission filters 113 are selected depending on a light emitting wavelength of an infrared LED used as a light source. For example, description below are provided in an assumption that a light emitting wavelength of an infrared LED is 950 nm.

With respect to the infrared ray transmission filters 113, a maximum value of the transmittance of light in the thickness direction of the film in a wavelength range of 400 to 830 nm are preferably 20% or less, further preferably 10% or less, and particularly preferably 5% or less. The transmittance thereof preferably satisfies the condition above in the entire wavelength range of 400 to 830 nm.

The minimum value of the transmittance of light in the thickness direction of the film in a wavelength range of 1,000 to 1,300 nm is preferably 70% or greater, more preferably 80% or greater, and further preferably 90% or greater. The transmittance preferably satisfies the conditions above in a portion of the wavelength range of 1,000 to 1,300 nm, and preferably satisfies the conditions above in a wavelength corresponding to a light emitting wavelength of the infrared LED.

The film thickness is preferably 0.1 to 20 µm. The lower limit is preferably 0.5 µm or greater. The upper limit is preferably 10 µm or less.

The spectral characteristics of the film are values obtained by measuring transmittance in a wavelength range of 300 to 1,300 nm by using a spectrophotometer (ref. glass substrate) of a ultraviolet-visible-near infrared ray spectrophotometer (U-4100 manufactured by Hitachi High-Technologies Corporation).

For example, an infrared ray transmission filter having such spectral characteristics can be formed, for example, by using a coloring composition including a compound having a maximum absorption wavelength in a wavelength range of 800 to 900 nm and a compound having a maximum absorption wavelength in a wavelength range of 400 to 700 nm.

As the compound having a maximum absorption wavelength in a wavelength range of 800 to 900 nm, for example, an infrared ray absorption substance described in the near-infrared ray absorption composition described above can be used. Among these, a pyrrolopyrrole coloring agent compound is preferable. The spectral characteristics of the infrared ray transmission filter can be easily adjusted to the range described above, by using a pyrrolopyrrole coloring agent compound. An infrared ray transmission filter having excellent heat resistance can be also formed.

Examples of the pyrrolopyrrole coloring agent compound include compounds below.

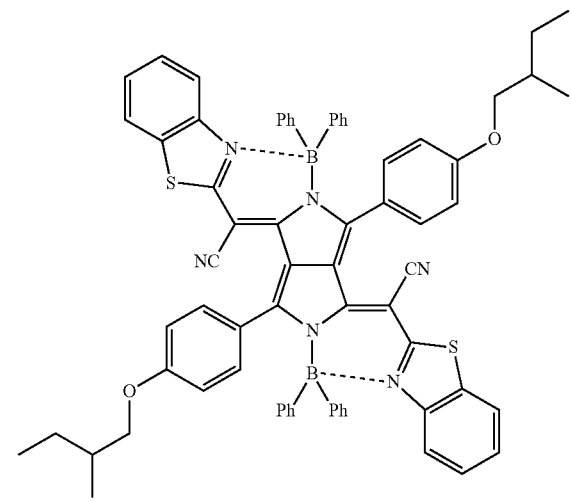

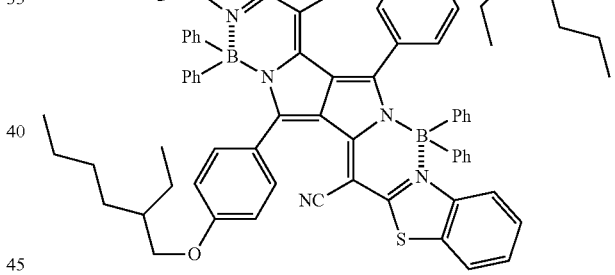

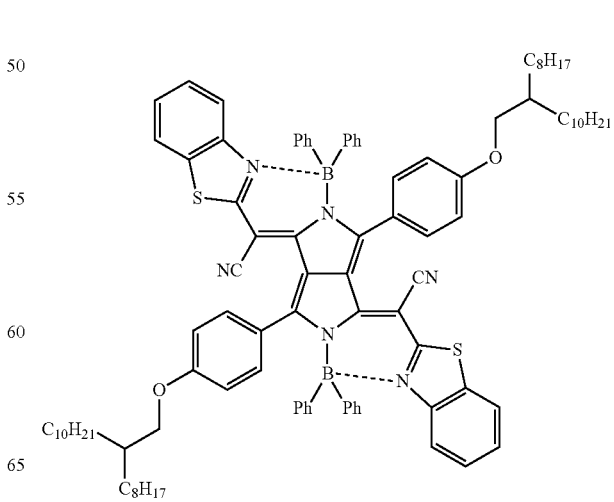

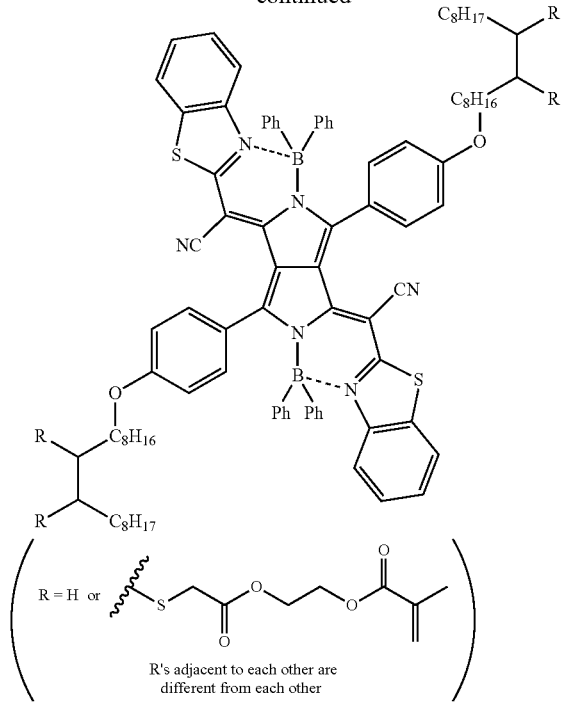

A compound (hereinafter, also referred to as a "coloring agent") having a maximum absorption wavelength in a wavelength range of 400 to 700 nm may be a pigment or may be a dye. For example, coloring agents disclosed in paragraphs 0019 to 0028 of JP2013-064998A can be used, and the contents thereof are incorporated to this specification.

As the preferable embodiment of the coloring agent, two or more coloring agents selected from a red coloring agent, a yellow coloring agent, a blue coloring agent, and a purple coloring agent are preferably contained, and a red coloring agent, a yellow coloring agent, a blue coloring agent, and a purple coloring agent are more preferably contained. As preferable specific examples, color index (C.I.) Pigment Red 254 as a red pigment, C. I. Pigment Yellow 139 as a yellow pigment, C. I. Pigment Blue 15:6 as a blue pigment, C. I. Pigment Violet 23 as a purple pigment are preferably contained. In a case where the coloring agent is obtained by combining a red coloring agent, a yellow coloring agent, a blue coloring agent, and a purple coloring agent, it is preferable that a mass ratio of the red coloring agent is 0.1 to 0.4 with respect to the total amount of the coloring agent, a mass ratio of the yellow coloring agent is 0.1 to 0.4 with respect to the total amount of the coloring agent, a mass ratio of the blue coloring agent is 0.20 to 0.60 with respect to the total amount of the coloring agent, and a mass ratio of the purple coloring agent is 0.01 to 0.30 with respect to the total amount of the coloring agent. It is more preferable that a mass ratio of the red coloring agent is 0.1 to 0.3 with respect to the total amount of the coloring agent, a mass ratio of the yellow coloring agent is 0.3 to 0.5 with respect to the total amount of the coloring agent, a mass ratio of the blue coloring agent is 0.3 to 0.5 with respect to the total amount of the coloring agent, and a mass ratio of the purple coloring agent is 0.05 to 0.25 with respect to the total amount of the coloring agent.

With respect to the coloring agent, a content of a pigment is preferably 95 mass % greater, more preferably 97 mass % greater, and even more preferably 99 mass % greater with respect to a total amount of the coloring agent.

In the coloring composition, the infrared ray absorption substance preferably contains 10 to 200 parts by mass and more preferably contains 50 to 150 parts by mass with respect to 100 parts by mass of the coloring agent. The content of the infrared ray absorption substance is preferably 0 to 60 mass % and more preferably 10 to 40 mass % with respect to the total solid content of the coloring composition. The content of the coloring agent is preferably 10 to 60 mass % and more preferably 30 to 50 mass % with respect to the total solid content of the coloring composition. The total amount of the infrared ray absorption substance and the coloring agent is preferably 1 to 80 mass %, more preferably 20 to 70 mass %, and even more preferably 30 to 70 mass % with respect to the total solid content of the coloring composition.

The expression "having a maximum absorption wavelength in a wavelength range of 800 to 900 nm" means having a wavelength exhibiting maximum absorbance in an absorption spectrum in a wavelength range of 800 to 900 nm. For example, it is preferable to have a wavelength exhibiting maximum absorbance in a wavelength range of 800 to 900 nm in an absorption spectrum in a wavelength range of 350 to 1,300 nm.

The expression "having a maximum absorption wavelength in a wavelength range of 400 to 700 nm" means having a wavelength exhibiting maximum absorbance in an absorption spectrum in a wavelength range of 400 to 700 nm. For example, it is preferable to have a wavelength exhibiting maximum absorbance in a wavelength range of 400 to 700 nm in an absorption spectrum in a wavelength range of 350 to 1,300 nm.

The coloring composition for forming the infrared ray transmission filters 113 may include a curable compound, a solvent, and the like in addition to the infrared ray absorption substance and the coloring agents.

Figure 2:
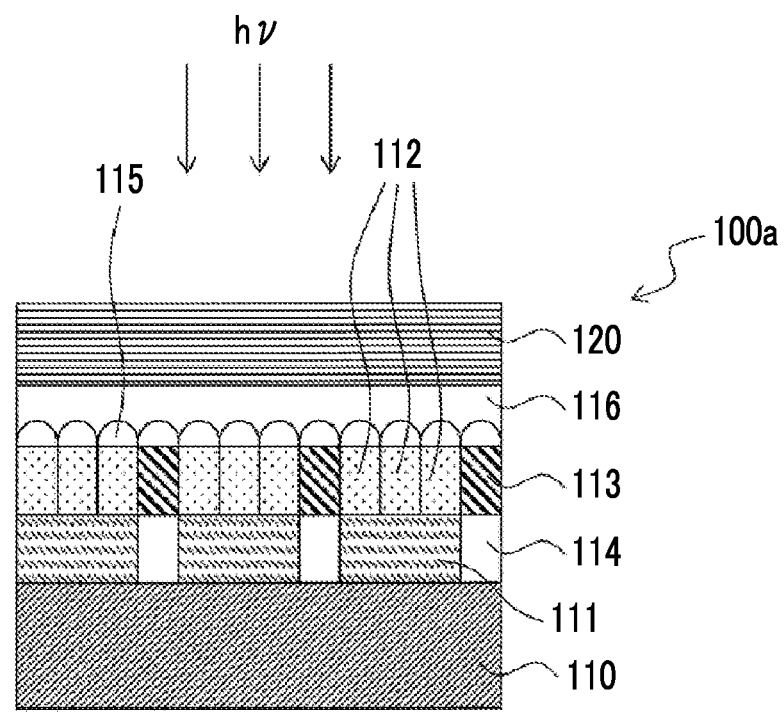
FIG. 2 is a cross-sectional view schematically illustrating a configuration according to another embodiment of the infrared sensor of the invention.

Another embodiment of the infrared sensor according to the invention is described by using FIG. 2. This embodiment is different from the infrared sensor 100 illustrated in FIG. 1, in view of further including a bandpass filter 120.

As the near-infrared ray absorption filters 111, the color filters 112, and the infrared ray transmission filters 113, those illustrated in FIG. 1 can be used.

As the bandpass filter 120, a filter that transmits visible light (light in wavelengths of 400 to 700 nm) and shields light in wavelengths of 970 nm or longer (preferably, light in wavelengths of 1,000 nm or longer) can be preferably used. With an infrared sensor 100a illustrated in FIG. 2, it is possible to more accurately detect light in wavelengths of 900 nm to 1,000 nm.

Subsequently, an image pick-up device is described as an example to which the infrared sensor is applied. Examples of the image pick-up device include a camera module.

Figure 3:
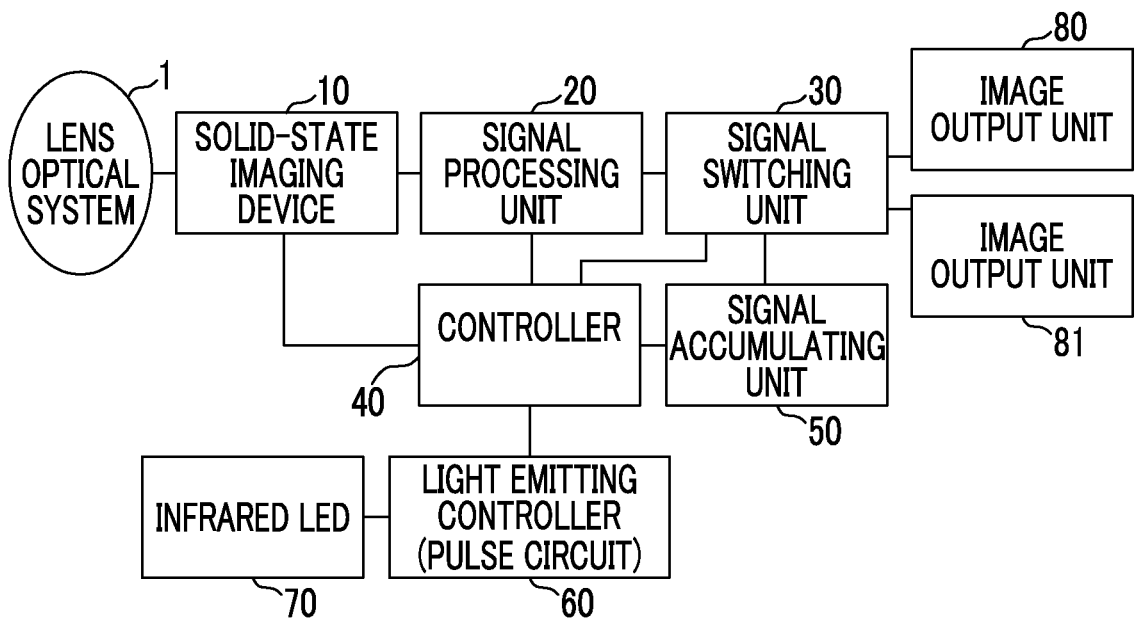
FIG. 3 is a functional block diagram schematically illustrating an image pick-up device to which an infrared sensor of the invention is applied.

FIG. 3 is a functional block diagram of an image pick-up device. The image pick-up device comprises a lens optical system 1, a solid-state imaging device 10, a signal processing unit 20, a signal switching unit 30, a controller 40, a signal accumulating unit 50, a light emitting controller 60, an infrared LED 70 of a light emitting element that emitting infrared light, and image output units 80 and 81. As the solid-state imaging device 10, the infrared sensor 100 described above can be used. All or a portion of the configurations except for those of the solid-state imaging device 10 and the lens optical system 1 may be formed on the same semiconductor substrate. With respect to the respect configurations of the image pick-up device, disclosure in paragraphs 0032 to 0036 of JP2011-233983A are referred to, and the contents thereof are incorporated to this specification.

As the infrared sensor, a motion sensor, a proximity sensor, a gesture sensor, and the like exist.

<Compound>

Subsequently, the compound according to the invention is described.

The compound according to the invention is a compound represented by Formula (1) described in the near-infrared ray absorption composition according to the invention.

The compound preferably has a maximum absorption wavelength in wavelengths of 900 nm to 1,000 nm, further preferably has a maximum absorption wavelength in wavelengths of 905 nm to 995 nm, and particularly preferably has a maximum absorption wavelength in wavelengths of 910 nm to 990 nm.

Various methods in the related art can be used, but the maximum absorption wavelength of the compound is preferably measured by using a chloroform solvent, for example, with a spectrophotometer UV-1800PC [manufactured by Shimadzu Corporation].

The compound according to the invention has a maximum absorption wavelength on a long wavelength side, and has excellent light fastness and excellent heat resistance.

The compound according to the invention can be preferably used in the formation of the near-infrared ray absorption filter that shields light in wavelengths of 900 nm to 1,000 nm. The compound can be used for ink, heat shielding, security, a solar cell, a device, or the like.

<Photosensitive Resin Composition>

Subsequently, the photosensitive resin composition according to the invention is described.

The photosensitive resin composition according to the invention contains the compound represented by Formula (1) above. The compound represented by Formula (1) is the same as the compound represented by Formula (1) above, and preferable ranges thereof are also the same.

The photosensitive resin composition according to the invention may have other components in addition to the compound represented by Formula (1), that is described in the near-infrared ray absorptive composition above.

EXAMPLES

Hereinafter, the invention is described in detail with reference to examples. Materials, use amounts, ratios, process details, process orders, and the like provided in the examples below can be appropriately changed without departing from the gist of the invention. Accordingly, ranges of the invention are not limited to the specific examples described below. Unless described otherwise, "%" and "parts" are based on a mass.

Hereinafter, propylene glycol monomethyl ether acetate is referred to as PGMEA.

In chemical formulae below, Me represents a methyl group, and Ph represents a phenyl group.

Synthesization Example 1

Synthesization of Compounds 1 and 2

Compounds 1 and 2 were synthesized by a synthesization scheme below with reference to Chem. Eur. J. 2009, 15, 4857.

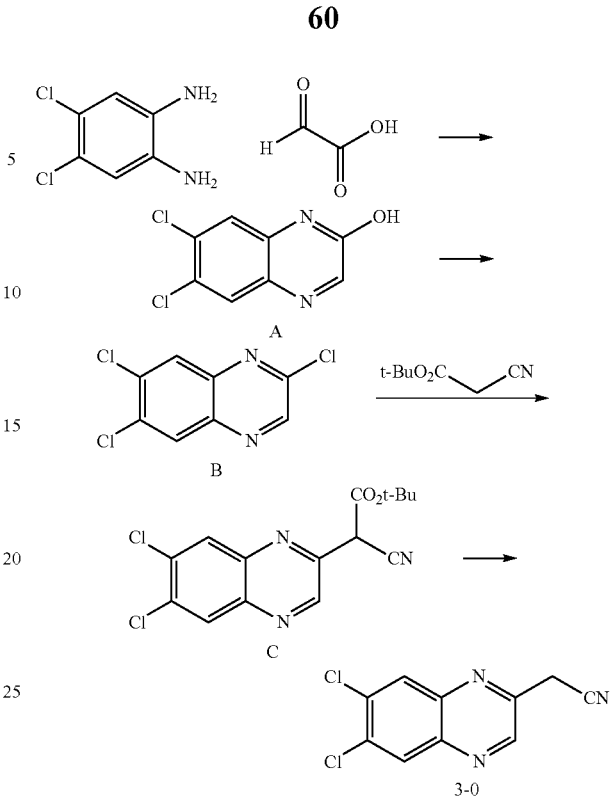

5.0 g of 4,5-dichloro-1,2-phenylenediamine (28 millimolar equivalent), 2.9 g of glyoxylic acid monohydrate (31 millimolar equivalent), and ethanol (120 ml) were put into a flask and stirring was performed for 12 hours in a heating reflux condition. After reaction, deposits were filtrated. Blast drying was performed on this crystal at 50° C., so as to obtain 5.5 g of an intermediate A.

5.0 g of the intermediate A (23 millimolar equivalent) and 30 ml of phosphorus oxychloride were put into a flask and were stirred for two hours in a heating reflux condition. After reaction, the reaction solution was poured into 300 ml of water, so as to filtrate a deposit. Blast drying was performed on this crystal, so as to obtain 5.0 g of an intermediate B.

1.3 g of a sodium hydride 60% solution (30 millimolar equivalent) and 10 mL of tetrahydrofuran were put into a flask, and tert-butyl 4.0 g of tert-butyl cyanoacetate (30 millimolar equivalent) was added dropwise in an ice bath. After stirring was performed for one hour at room temperature, 5.0 g of the intermediate B (22 millimolar equivalent) was added and stirred for 12 hours. The reaction solution was poured into 75 ml of water, 3 ml of acetic acid was added, and deposits were filtrated. Blast drying was performed on this crystal at 50° C., so as to obtain 4.6 g of an intermediate C.

4.0 g of the intermediate C (12 millimolar equivalent), 12 ml of trifluoro acetate, and 24 ml of dichloromethane were put into a flask and stirred at 60° C. for one hour. After reaction, a sodium carbonate aqueous solution was added, and an organic layer was extracted with chloroform. A solvent was removed under reduced pressure, and the obtained crystal was purified by recrystallization with ethyl acetate. Blast drying was performed on this crystal at 50° C., so as to obtain 2.0 g of an intermediate 3-0.

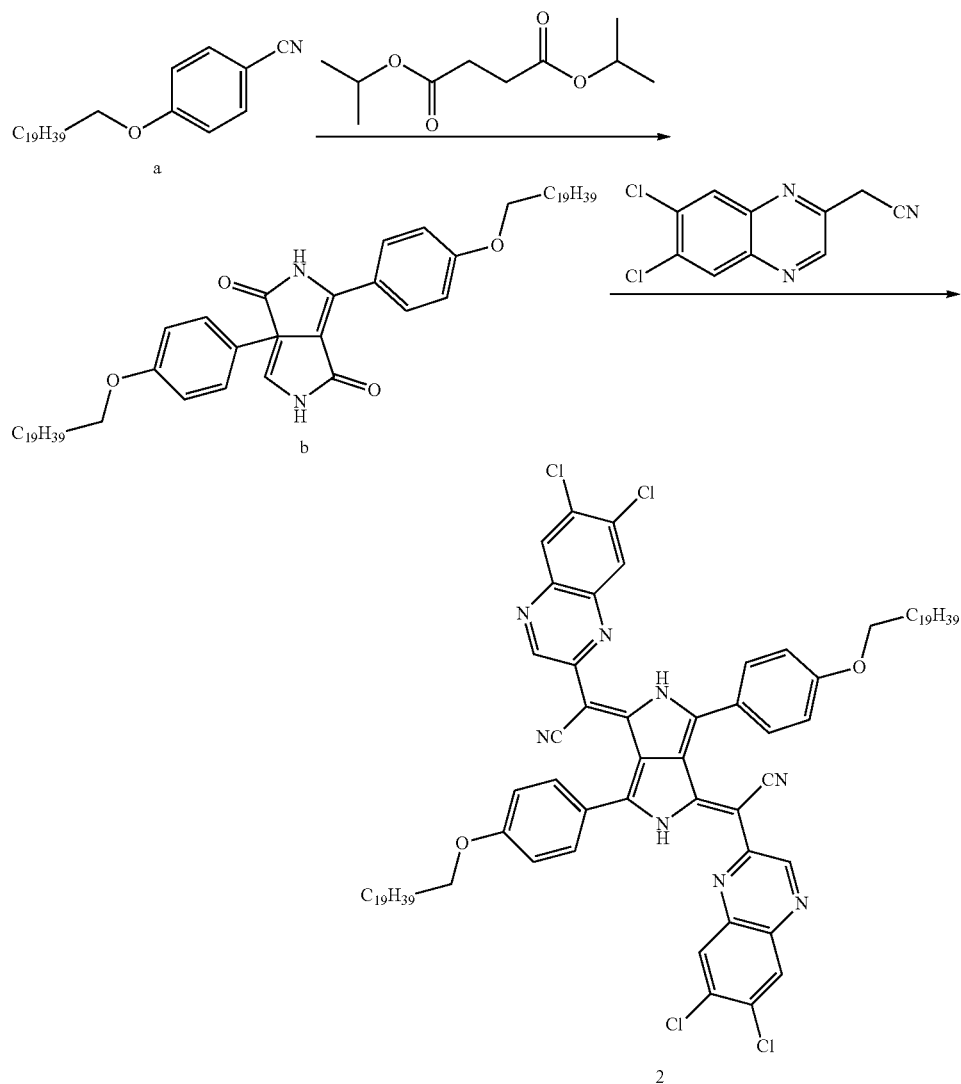

47 g of a compound a (120 millimolar equivalent), 14 g of diisopropyl succinate (67 millimolar equivalent), 65 ml of t-amyl alcohol, and 25 g of potassium t-butoxide (220 millimolar equivalent) were put into a flask and stirred at 120° C. for three hours. After reaction, 100 ml of methanol was added, and a deposit was filtrated. Blast drying was performed on this crystal at 50° C., so as to obtain 5.5 g of a compound b.

160 mg of the compound b (0.18 millimolar equivalent), 110 mg of 2-(6,7-dichloroquinoxalin-2-yl) acetonitrile (0.43 mole equivalent) were stirred in 7 mL of toluene, and subsequently 170 mg of phosphorus oxychloride (8 mole equivalent) was added and stirred at 100° C. for two hours. Cooling was performed to room temperature, 30 ml of methanol was added, and stirring was performed for 30 minutes. A precipitated crystal was filtrated, so as to 150 mg of the compound 2.

Mass: 1319.7 ([M+1], 100%)

λmax: 758 nm (CHCl$_3$)

$^1$H-NMR (CDCl$_3$): δ0.9-1.6 (m, 78H), 4.0 (d, 4H), 7.3 (d, 4H), 7.7 (d, 4H), 7.9 (s, 2H), 8.1 (s, 2H), 9.1 (s, 2H), 13.7 (s, 2H)

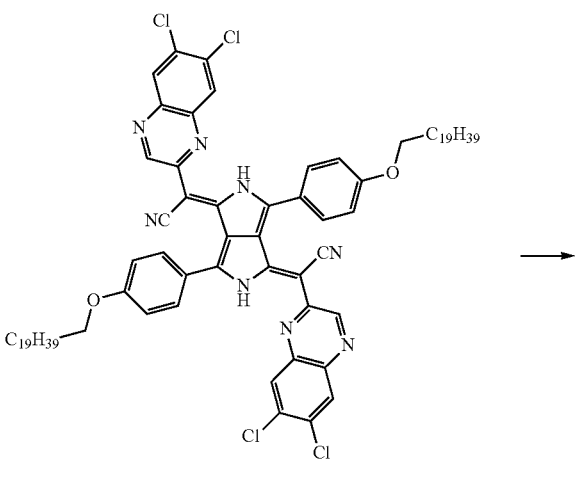

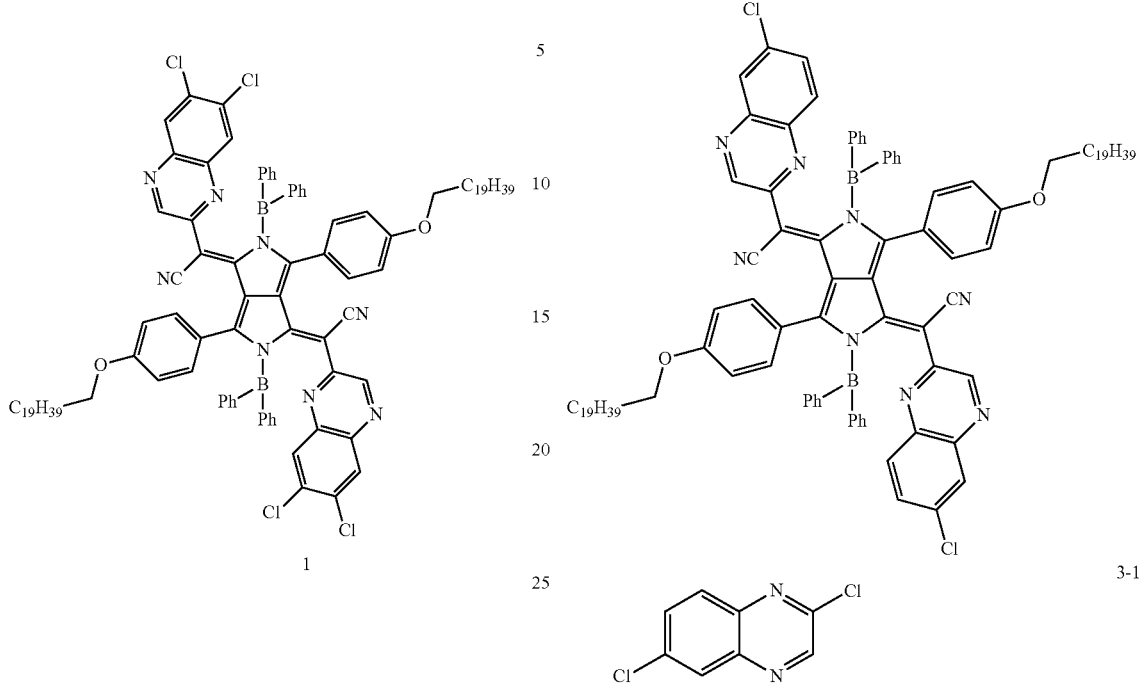

530 mg of titanium chloride (2.8 millimolar equivalent) was added in 6 ml of toluene containing 530 mg of diphenylborinic acid 2-aminomethyl ester (1.7 millimolar equivalent) and stirred at 35° C. for 30 minutes. Subsequently, a toluene mixture liquid (0.1 mM) containing 150 mg of the compound 2 was added, and was stirred in a heating reflux condition for two hours. Cooling was performed to room temperature, 30 ml of methanol was added, and stirring was performed for 30 minutes. The precipitated crystal was filtrated and purified in silica column chromatography (hexane/ethyl acetate solvent), so as to obtain 110 mg of the compound 1 in an yield of 38% (2 step).

Mass: 1650.8 ([M+1], 100%)

$\lambda$max: 885 nm (CHCl$_3$)

$\varepsilon$: 2.6×10$^5$ dm$^3$/mol·cm $^1$H-NMR (CDCl$_3$): $\delta$0.9-1.6 (m, 78H), 3.9 (d, 4H), 6.2 (d, 4H), 6.6 (d, 4H), 7.2 (m, 5H), 7.3 (m, 5H), 7.8 (s, 2H), 8.2 (s, 2H), 9.0 (s, 2H)

Synthesization Example 2

Synthesization of Compound 3

In Synthesization Example 1, a compound 3 was synthesized in the same method as Synthesization Example 1 except for using an intermediate 3-1 below instead of an intermediate 3-0.

Synthesization Example 3

Synthesization of Compound 4

In Synthesization Example 1, a compound 4 was synthesized in the same manner as in Synthesization Example 1 except for using an intermediate 4-1 disclosed in Tetrahedron, 2005, vol. 61, #46, pages 11010 to 11019 instead of the intermediate 3-0.

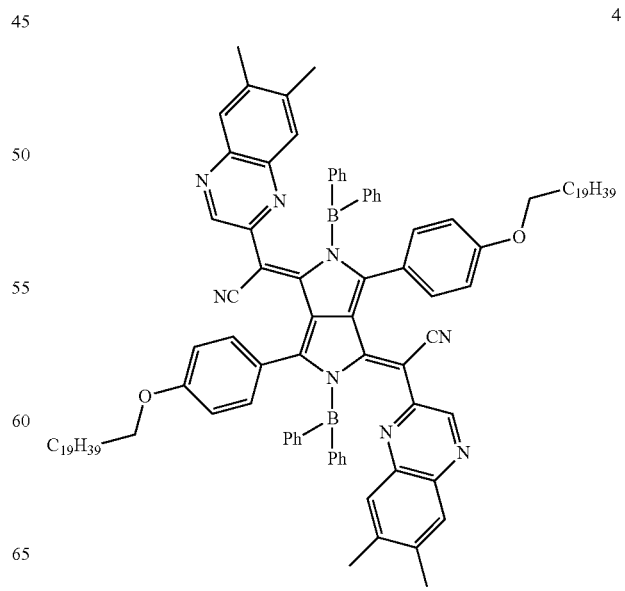

4-1

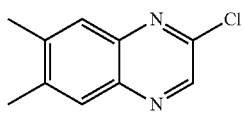

Synthesization Example 4

Synthesization of Compound 15

In Synthesization Example 1, a compound 15 was synthesized in the same manner as in Synthesization Example 1 except for changing 4,5-dichloro-1,2-diamine to 4,5-dioctadecylbenzene-1,2-diamine (compound disclosed in Journal of Organic Chemistry, 2001, vol. 66, #2, pages 481 to 487).

15

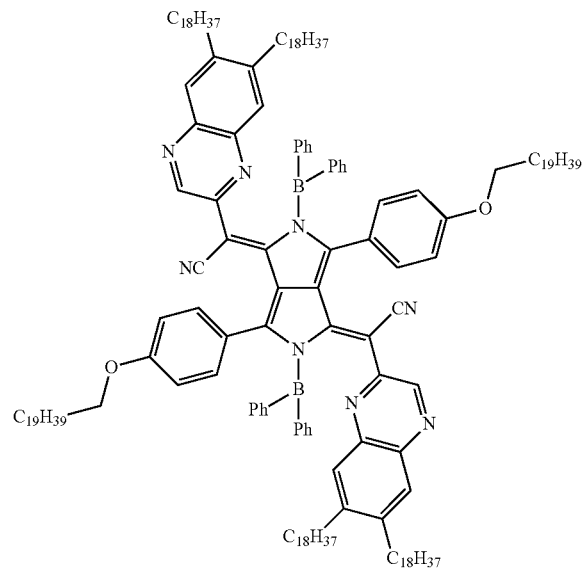

Synthesization Example 5

Synthesization of Compound 16

In Synthesization Example 1, a compound 16 was synthesized in the same manner as in Synthesization Example 1, except for changing 4,5-dichloro-1,2-diamine to 4,5-bis(octadecyloxy)benzene-1,2-diamine (compound disclosed in Journal of Organic Chemistry, 2008, vol. 73, #7, pages 2548 to 2553).

16

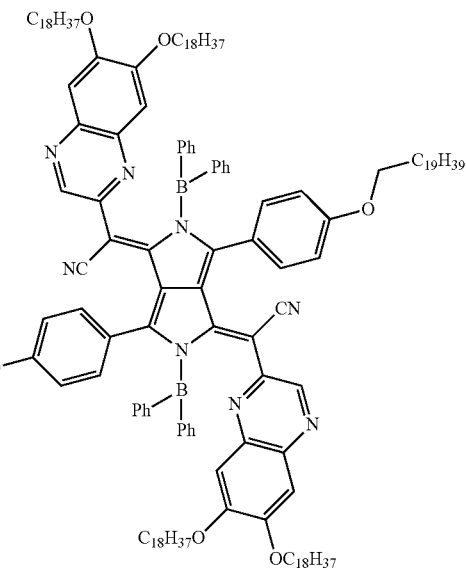

Synthesization Example 6

Synthesization of Compound 17

In Synthesization Example 1, a compound 17 was synthesized in the same manner as in Synthesization Example 1, except for changing 4,5-dichloro-1,2-diamine to 4-phenylbenzene-1,2-diamine (compound disclosed in Journal of Organic Chemistry, 1995, vol. 38, #18, pages 3638 to 3644).

17

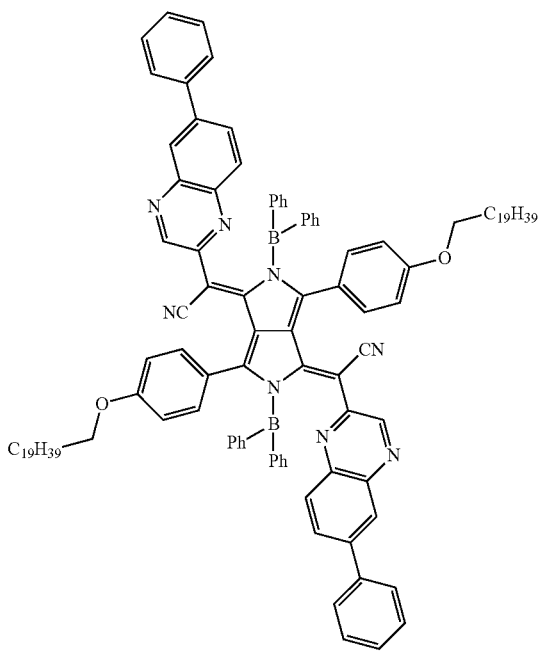

Synthesization Example 7

Synthesization of Compound 18

In Synthesization Example 1, a compound 18 was synthesized in the same manner as in Synthesization Example 1, except for changing 4,5-dichloro-1,2-diamine to 4-(naphthalen-2-yl)benzene-1,2-diamine (compound disclosed in Journal of Organic Chemistry, 1997, vol. 40, #18, pages 2818 to 2824).

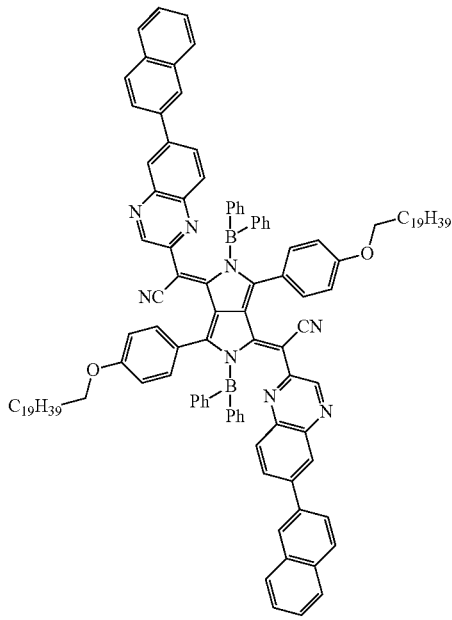

Synthesization Example 8

Synthesization of Compound 19

In Synthesization Example 1, a compound 19 was synthesized in the same manner as in Synthesization Example 1 except for changing the compound a to 2-naphthonitrile.

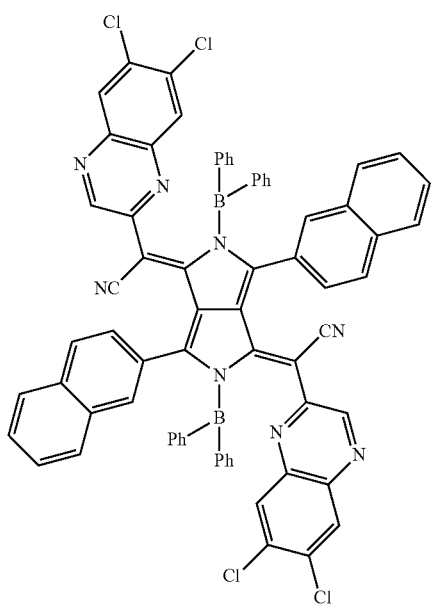

Synthesization Example 9

Synthesization of Compound 20

In Synthesization Example 1, a compound 20 was synthesized in the same manner as in Synthesization Example 1, except for changing the compound a to 2-cyanopyridine.

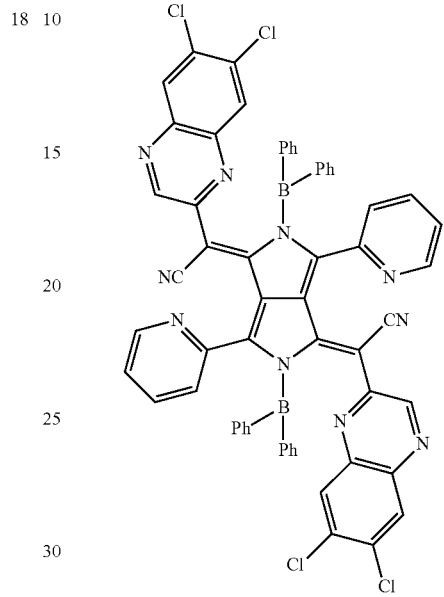

Synthesization Example 10

Synthesization of Compound 21

In Synthesization Example 1, a compound 21 was synthesized in the same manner as in Synthesization Example 1, except for changing the compound a into 2-benzothiazole carbonitrile.

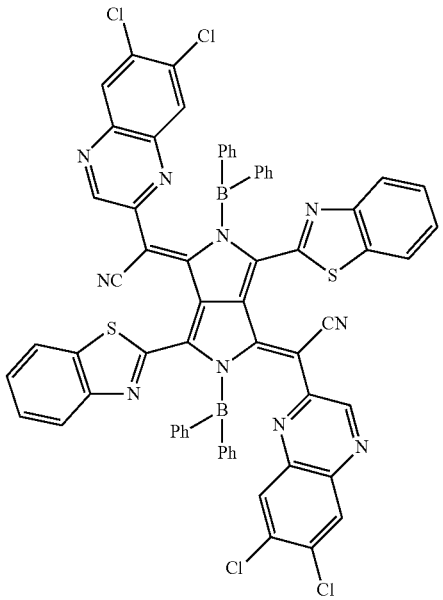

Synthesization Example 11

Synthesization of Compound 22

In Synthesization Example 1, a compound 22 was synthesized in the same manner as in Synthesization Example 1, except for changing diphenylborinic acid 2-aminomethyl ester and titanium chloride to chlorodioctyloborane (compound disclosed in Tetrahedron Letters, 1970, pages 1687 to 1688).

22

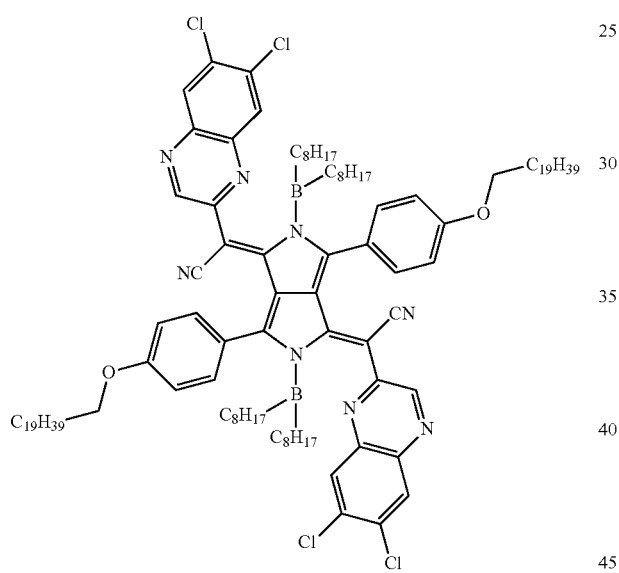

Synthesization Example 12

Synthesization of Compound 23

In Synthesization Example 1, a compound 23 was synthesized in the same manner as in Synthesization Example 1, except for changing diphenylborinic acid 2-aminomethyl ester and titanium chloride to chlorodi(naphthalen-1-yl)borane (compound disclosed in Bull. Acad. Sci. USSR Div. Chem. Sci., 1956, page 359).

23

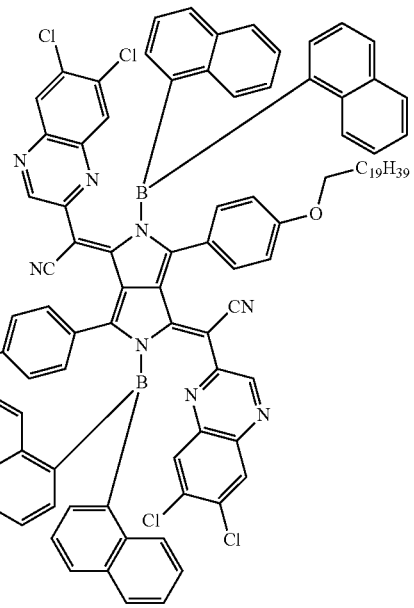

Synthesization Example 13

Synthesization of Compound 24

In Synthesization Example 1, a compound 24 was synthesized in the same manner as in Synthesization Example 1, except for changing diphenylborinic acid 2-aminomethyl ester and titanium chloride to chlorobis(5-methylthiophen-2-yl)borane (compound disclosed in WO2012/25760A1).

24

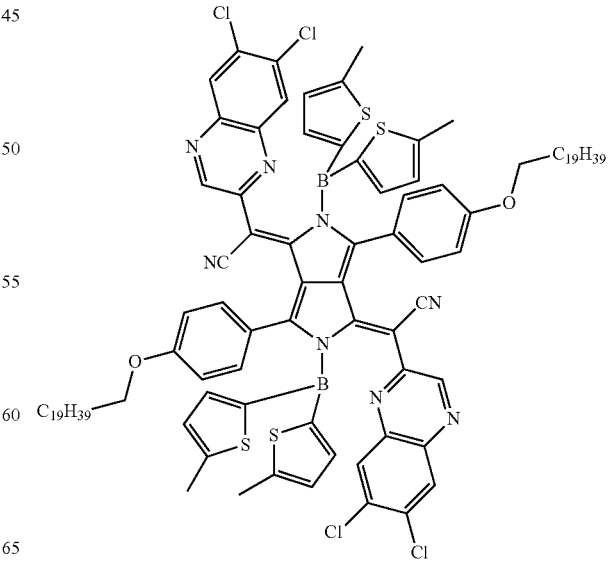

Synthesization Example 14

Synthesization of Compound 5

In Synthesization Example 1, a compound 5 was obtained in the same manner as in Synthesization Example 1, except for changing diphenylborinic acid 2-aminomethyl ester and titanium chloride to 0.42 mL of boron trifluoride diethyl ether complex (3.4 millimolar equivalent), and 130 mg of diisopropylmethylamine (1.1 millimolar equivalent).

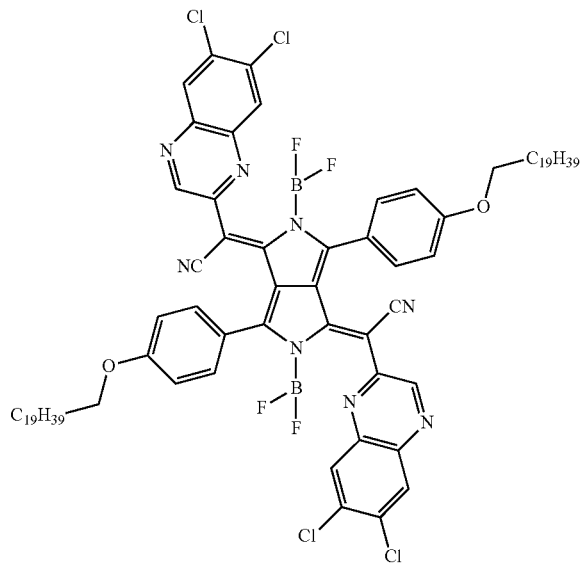

5

Synthesization Example 15

Synthesization of Compound 36

In Synthesization Example 1, a compound 36 was synthesized in the same manner as in Synthesization Example 1, except for changing the compound a to an intermediate 36-1.

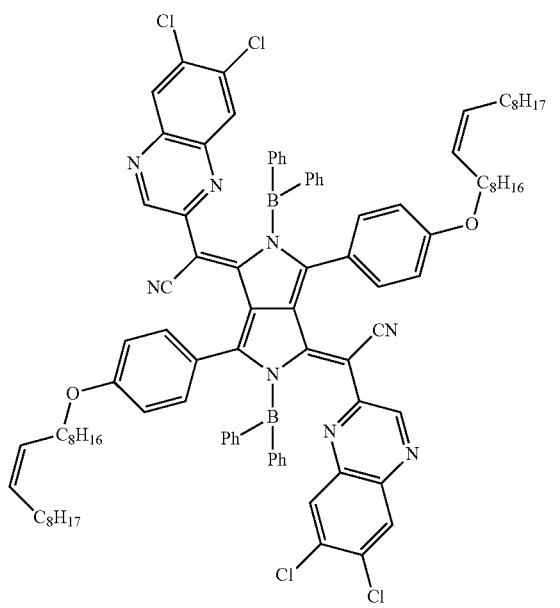

36

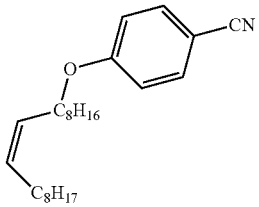

36-1

Synthesization Example 16

Synthesization of Compound 37

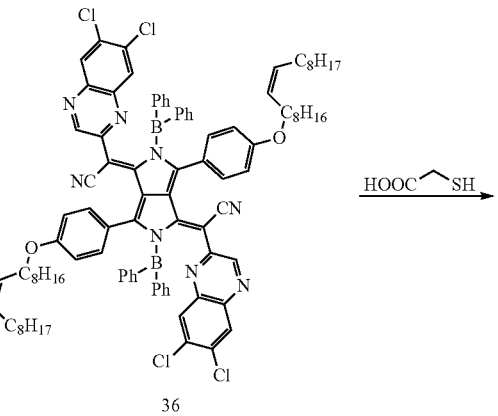

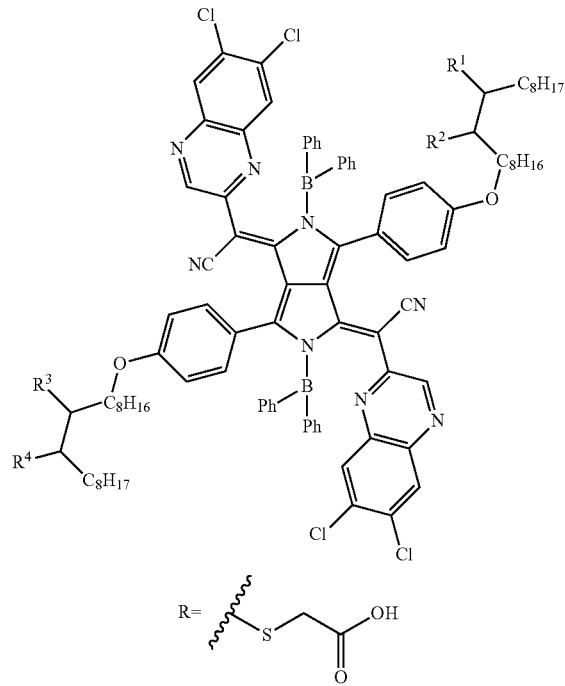

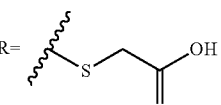

37

Temperature was increased to 82° C. under a nitrogen atmosphere by adding 2 parts by mass of the compound 36, 1.8 parts by mass of thioglycolic acid, and 20 parts by mass of toluene. Subsequently, 0.5 parts by mass of dimethyl 2,2'-isobis(2-methylpropionate) was added to the reaction solution and heating and stirring was performed for one hour and a half. Dimethyl 2,2'-isobis(2-methylpropionate) was added to the reaction solution by 0.5 parts by mass twice for every one hour and a half, and heating and stirring were performed. After reaction was completed, the temperature was returned to room temperature, methanol was added, and the precipitated solid was filtrated, so as to obtain 1.8 parts by mass of a compound 37.

In compound 37, one of $R^1$ and $R^2$ represents a hydrogen atom, and the other represented the substituent R, and one of $R^3$ and $R^4$ represented a hydrogen atom, and the other represents the substituent R.

Synthesization Example 17

Synthesization of Compound 39

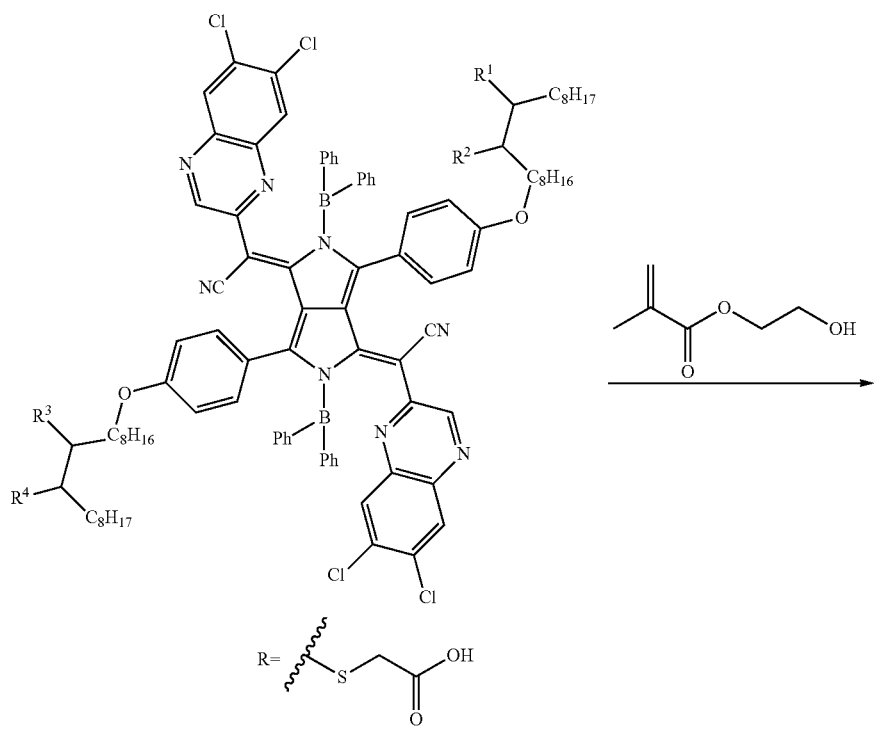

-continued

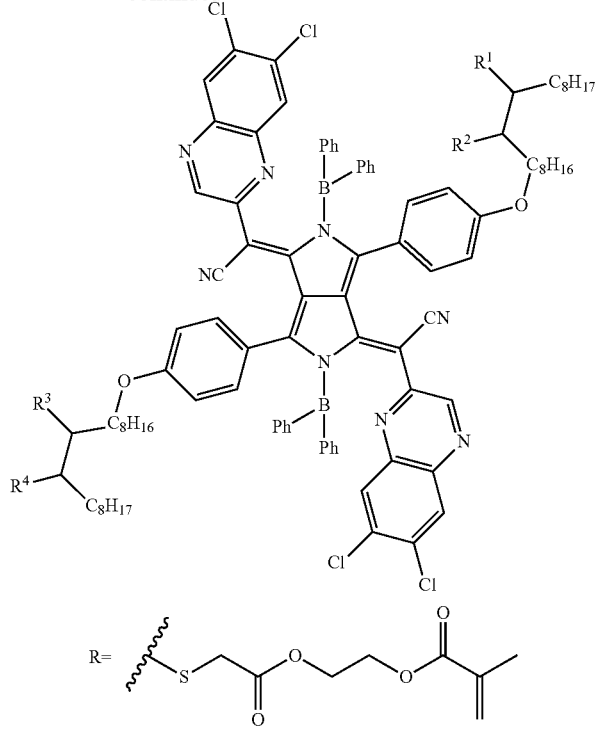

39

1 part by mass of the compound 37, 0.3 parts by mass of dimethylaminopyridine, 0.35 parts by mass of 1-ethyl-3-(3-dimethylaminopropyl)carbodiimide hydrochloride, and 20 parts by mass of methylene chloride are added and stirred at room temperature. 0.5 parts by mass of 2-hydroxyethyl methacrylate were added to this mixture liquid, and stirring was performed at room temperature for three hours. After the reaction was completed, liquid separation purification was performed with 1 mol/l of hydrochloric acid, methanol was added to an organic layer, and the precipitated solid was filtrated, so as to obtain 0.55 parts by mass of a compound 39.

In compound 39, one of $R^1$ and $R^2$ represents a hydrogen atom and the other represents the substituent R, and one of $R^3$ and $R^4$ represents a hydrogen atom and the other represents the substituent R.

Example 1

After 1.98 parts by mass of a binder A described below as an alkali soluble resin, 1.69 parts by mass of the compound 1, 0.19 parts by mass of A-DPH-12E (manufactured by Shin-Nakamura Chemical Co., Ltd.) as a polymerizable compound, 0.09 parts by mass of IRGACURE-OXE 01 (1,2-octanedione, 1-[4-(phenylthio)-,2-(O-benzoyloxime)], manufactured by BASF SE Corp.) as a photopolymerization initiator, 0.01 parts by mass of p-methoxyphenol as a polymerization inhibitor, 0.76 parts by mass of a 1.0 mass % PGMEA solution of MEGAFACE F-781 (manufactured by DIC Corporation, fluorine-containing polymer-type surfactant) as a fluorine-based surfactant, and 4.53 parts by mass of PGMEA as a solvent were mixed and stirred, and filtration was performed with a filter (manufactured by Nihon Pall Ltd.) made of nylon having a hole diameter of 0.5 μm, so as to prepare a photosensitive resin composition.

Binder A: Compound below (Mw: 14,000, acid value: 30 mgKOH/g)

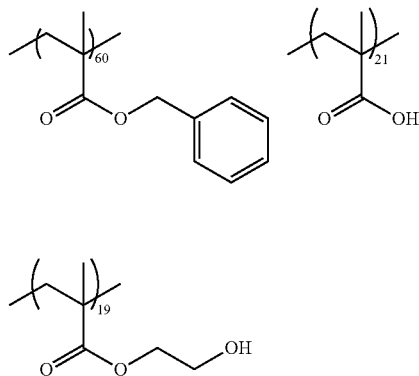

Examples 2 and 3

Instead of the compound 1, the photosensitive resin composition was prepared in the same manner as in Example 1, except for using the compounds 3 and 4.

Comparative Example 1

A photosensitive resin composition was prepared in the same manner as in Example 1, except for using a compound A below (compound D-158 disclosed in JP2010-222557A) instead of the compound 1.

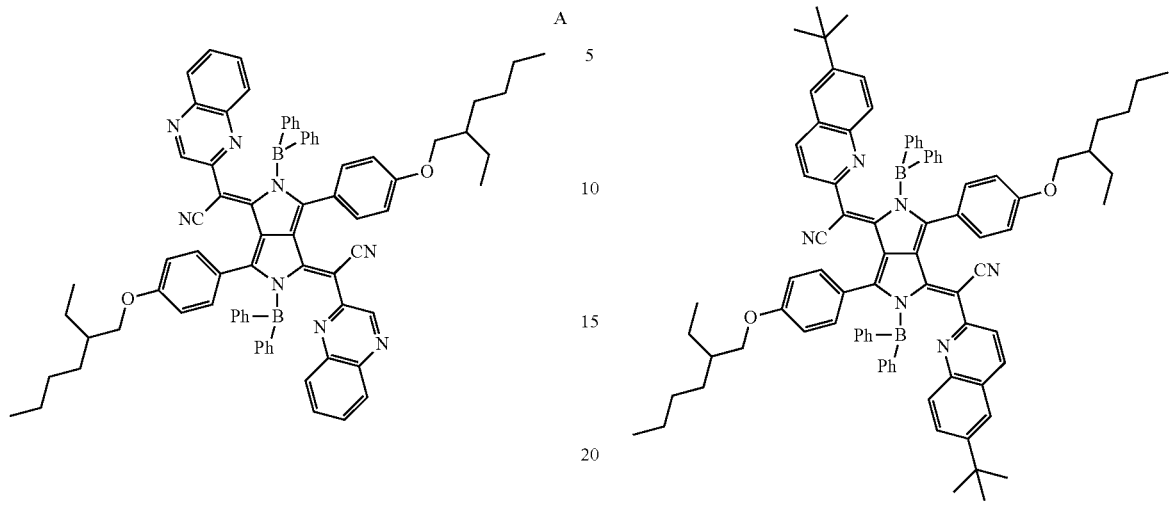

Comparative Example 2

A photosensitive resin composition was prepared in the same manner as in Example 1, except for using a compound B below instead of the compound 1.

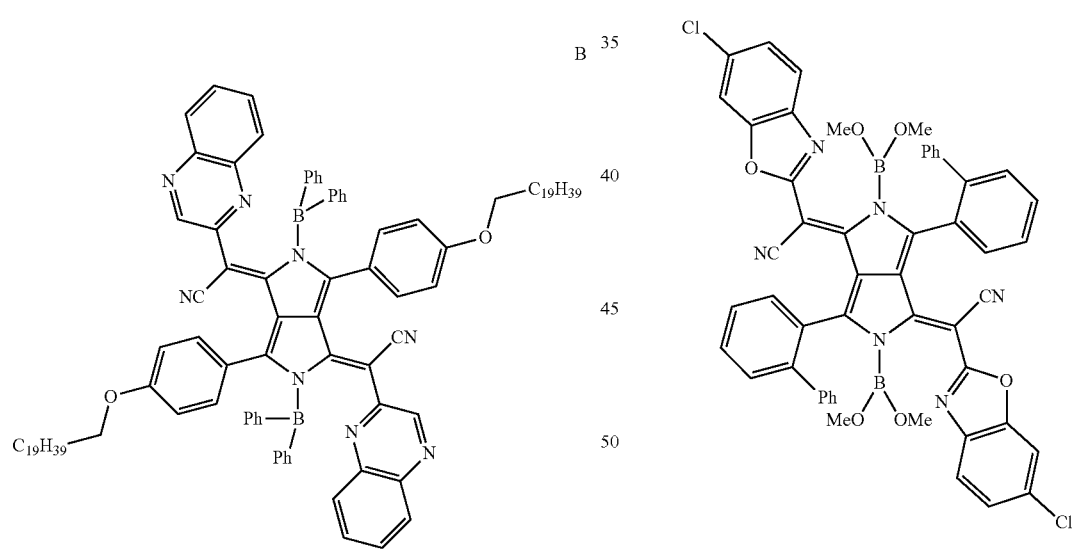

Comparative Example 3

A photosensitive resin composition was prepared in the same manner as in Example 1, except for using a compound C below (a compound D-141 disclosed in JP2010-222557A) instead of the compound 1.

Comparative Example 4

A photosensitive resin composition was prepared in the same manner as in Example 1, except for using a compound D below (compound D-5 disclosed in JP2010-222557A) instead of the compound 1.

A glass substrate was coated with the photosensitive resin composition prepared above by using a spin coater (manufactured by Mikasa Co., Ltd.), so as to form a coated film. The thickness of the coated film is adjusted such that a thickness of a coloration film (average thickness) became 0.8 µm. Subsequently, a heating treatment was performed on the coated film for 120 seconds by using a hot plate of 100° C.

Subsequently, light in a wavelength of 365 nm was applied by 1,000 mJ/cm$^2$, so as to prepare a near-infrared ray absorption filter by using an i-ray stepper exposure device FPA-3000i5+(manufactured by Canon Inc.).

<Light Fastness>
After the obtained near-infrared ray absorption filter was irradiated with a xenon lamp was applied by 50,000 lux for 20 hours (corresponding to 1,000,000 lux·h), an ΔEab value of a color difference before and after a light-fast test was measured. A smaller ΔEab value indicates more satisfactory light fastness.

The ΔEab value is a value obtained from a color difference formula below according to a CIE 1976 (L*, a*, b*) space color system (Handbook of Color Science, New Edition, edited by the Color Science Association of Japan, (1985), p. 266).

$$\Delta Eab\{(\Delta L^*)^2+(\Delta a^*)^2+(\Delta b^*)^2\}^{1/2}$$

<<Determination Criteria>>
5: ΔEab value<3
4: 3≤ΔEab value<5
3: 5≤ΔEab value<10
2: 10≤ΔEab value<20
1: 20≤ΔEab value <Heat Resistance>
After the near-infrared ray absorption filter was heated to 260° C. for 30 minutes by a hot plate, the ΔEab value of a color difference before and after heat resistance test was measured using a color meter MCPD-1000 (manufactured by Otsuka Electronics Co., Ltd.), so as to evaluate a criterion below. A smaller ΔEab value indicates more satisfactory heat resistance.

<<Determination Criteria>>
5: ΔEab value<3
4: 3≤ΔEab value<5
3: 5≤ΔEab value<10
2: 10≤ΔEab value<20
1: 20≤ΔEab value <Measurement of Maximum Absorption Wavelength>
A maximum absorption wavelength of the obtained near-infrared ray absorption filter (film) was measured by using a spectrophotometer UV-1800PC [manufactured by Shimadzu Corporation].

TABLE 1

|  | Compound | Light fastness | Heat resistance | Maximum absorption wavelength (film) |
|---|---|---|---|---|
| Example 1 | Compound 1 | 5 | 5 | 980 nm |
| Example 2 | Compound 3 | 5 | 5 | 950 nm |
| Example 3 | Compound 4 | 5 | 5 | 930 nm |
| Comparative Example 1 | Compound A | 3 | 3 | 920 nm |
| Comparative Example 2 | Compound B | 3 | 3 | 920 nm |
| Comparative Example 3 | Compound C | 3 | 3 | 880 nm |
| Comparative Example 4 | Compound D | 2 | 2 | 790 nm |

As clearly understood from the results above, the near-infrared ray absorption filters of Examples 1 to 3 using the photosensitive resin compositions including the compound represented by Formula (1) had excellent light fastness and excellent heat resistance. The near-infrared ray absorption filters of Examples 1 to 3 had maximum absorption wavelengths in wavelengths of 900 to 1,000 nm.

Meanwhile, the near-infrared ray absorption filters of Comparative Examples 1 to 4 using compounds different from the compound represented by Formula (1) had deteriorated light fastness and deteriorated heat resistance, compared with those of Examples 1 to 3. The maximum absorption wavelengths had on the shorter wavelength side than those of Examples 1 to 3.

In the examples above, even if the surfactant was changed to the fluorine-based surfactant disclosed in paragraph 0053, the same performance was able to be obtained.

Example 4

In Example 1, the polymerizable compound was changed to LIGHT ACRYLATE DCP-A, KAYARAD D-330, KAYARAD D-320, KAYARAD D-310, or KAYARAD DPHA in the same mass, the others were set to be the same as those in Example 1, and tests were performed. Preferable results which were the same as that of Example 1 were able to be obtained.

Example 5

In Example 1, the photopolymerization initiator was changed to IRGACURE-OXE02 (manufactured by BASF SE Corp.), the others were set to be the same as those in Example 1, and tests were performed. Preferable results which were the same as that of Example 1 were able to be obtained.

Examples B1 to B9 and Comparative Examples B1 to B4

Preparation of Photosensitive Resin Composition

Compositions below were mixed and stirred, and filtration was performed by using DFA4201NXEY (0.45 μm nylon filter) manufactured by Nihon Pall Ltd., so as to prepare a photosensitive resin composition B. The solid content of the photosensitive resin composition was 31 mass %, and a content of a near-infrared ray absorption substance with respect to a total solid content of the photosensitive resin composition was 7.5 mass %.

<Composition>
Near-infrared ray absorption substance (Compound shown in Table 2): 2.3 parts Resin 1 (structure below): 12.9 parts Polymerizable compound: Dipentaerythritol hexaacrylate (manufactured by Nippon Kayaku Co., Ltd., Product name: KAYARAD DPHA): 12.9 parts Photopolymerization initiator: IRGACURE-OXE01 (manufactured by BASF SE Corp.): 2.5 parts Ultraviolet absorbing agent: UV503 (Daito Chemical Co., Ltd.): 0.5 parts Surfactant: MEGAFACE F-781F (manufactured by DIC Corporation, fluorine-containing polymer-type surfactant): 0.04 parts Polymerization inhibitor: p-methoxyphenol: 0.006 parts Cyclohexanone: 49.6 parts Propylene glycol monomethyl ether acetate: 19.3 parts Resin 1: Structure below (A ratio in a repeating unit is a molar ratio), Mw=11,500

Synthesization was performed by a method disclosed in paragraphs 0247 to 0249 of JP2012-198408A.

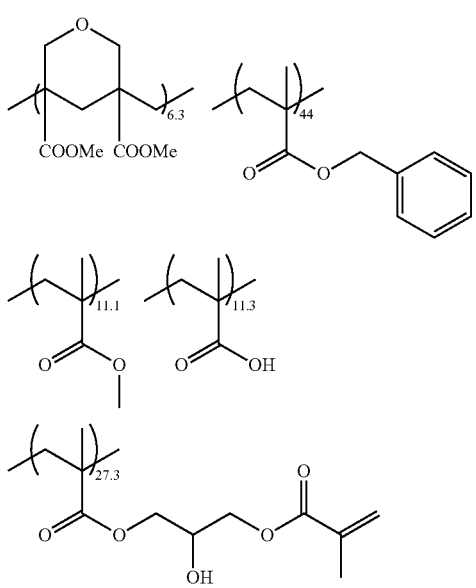

<Manufacturing of Near-Infrared Ray Absorption Filter>

Glass substrates (1737 manufactured by Corning Incorporated) were coated with respective photosensitive resin compositions by using a spin coater such that film thicknesses after drying become 1.0 μm, and a heating treatment (prebaking) was performed for 120 seconds by using a hot plate of 100° C.

Subsequently, beta exposure was performed by 500 mJ/cm$^2$ by using an i-ray stepper exposure device FPA-3000i5+(manufactured by Canon Inc.). Subsequently, puddle development was performed at 23° C. for 60 seconds by using CD-2060 (manufactured by FUJIFILM Electronic Materials), a rinse treatment was performed with pure water on a glass substrate on which a beta coloration layer was formed, and spray drying was performed. The heating treatment (post baking) was performed for 300 seconds by using a hot plate of 200° C., so as to obtain a near-infrared ray absorption filter. With respect to the near-infrared ray absorption filter, light fastness, heat resistance, and a maximum absorption wavelength were evaluated in the same manner as in Example 1.

TABLE 2

| | Compound | Light fastness | Heat resistance | Maximum absorption wavelength (film) |
|---|---|---|---|---|
| Example B1 | Compound 1 | 5 | 5 | 980 nm |
| Example B2 | Compound 3 | 5 | 5 | 950 nm |
| Example B3 | Compound 4 | 5 | 5 | 930 nm |
| Example B4 | Compound 25 | 5 | 5 | 930 nm |
| Example B5 | Compound 26 | 5 | 5 | 950 nm |
| Example B6 | Compound 27 | 5 | 5 | 990 nm |
| Example B7 | Compound 28 | 5 | 5 | 980 nm |
| Example B8 | Compound 29 | 5 | 5 | 980 nm |
| Example B9 | Compound 30 | 5 | 5 | 970 nm |
| Comparative Example B1 | Compound A | 3 | 3 | 920 nm |
| Comparative Example B2 | Compound B | 3 | 3 | 920 nm |
| Comparative Example B3 | Compound C | 3 | 3 | 880 nm |
| Comparative Example B4 | Compound D | 2 | 2 | 790 nm |

As clearly understood from the results above, the near-infrared ray absorption filters of Examples B1 to B9 using the photosensitive resin compositions including the compound represented by Formula (1) had excellent light fastness and heat resistance. The near-infrared ray absorption filters had maximum absorption wavelengths in wavelengths of 900 to 1,000 nm.

Meanwhile, the near-infrared ray absorption filters of Comparative Examples B1 to B4 using the compounds different from the compound represented by Formula (1) had deteriorated light fastness and deteriorated heat resistance compared with Examples B1 to B9. The maximum absorption wavelengths were on the shorter wavelength side than those of Examples B1 to B9.

In the examples, even if the surfactant was changed to the fluorine-based surfactant disclosed in paragraph 0053, the same performances were able to be obtained.

Example 100

Manufacturing of Infrared Sensor

The infrared sensor illustrated in FIG. 1 was manufactured by using the near infrared ray filters of Examples 1 to 3. It was possible to detect an object by using this infrared sensor. The color filter 112 was manufactured in the same manner as an example in JP2014-043556A. The infrared ray transmission filter 113 was manufactured by the method below.

<Manufacturing of Infrared Ray Transmission Filter>

[Preparation of Pigment Dispersion Liquids 1-1 to 1-5]

The mixture liquid of the composition below was mixed and dispersed with a beads mill (a high pressure dispersing machine with pressure reducing mechanism NANO-3000-10 (manufactured by Beryu corp.)) by using zirconia beads in a diameter of 0.3 mm, until an infrared ray absorption substance had an average particle diameter shown in the table, so as to prepare a pigment dispersion liquid. In the table, usage amounts of the corresponding components (Unit: parts by mass) are shown.

The average particle diameter of the pigment in the pigment dispersion liquid was measured by using MICROTRACUPA 150 manufactured by Nikkiso Co., Ltd. in a volume basis. The measurement results are shown in the table.

[Preparation of Pigment Dispersion Liquids 2-1 to 2-6]

The mixture liquid of the composition below was mixed and dispersed for three hours with a beads mill (a high pressure dispersing machine with pressure reducing mechanism NANO-3000-10 (manufactured by Beryu corp.)) by using zirconia beads in a diameter of 0.3 mm, so as to prepare a pigment dispersion liquid. In the table, usage amounts of the corresponding components (Unit: parts by mass) are shown.

TABLE 3

| | Infrared ray absorption substance | | | | |
|---|---|---|---|---|---|
| | Type | Average particle diameter (nm) | Coloring agent | Resin | Organic solvent |
| Pigment dispersion liquid 1-1 | Pyrrolopyrrole pigment 1 (13.5) | 75 | | Dispersion resin 1 (4.0) | PGMEA (82.5) |
| Pigment dispersion liquid 1-2 | Pyrrolopyrrole pigment 1 (13.5) | 150 | | Dispersion resin 1 (4.0) | PGMEA (82.5) |
| Pigment dispersion liquid 1-3 | Pyrrolopyrrole pigment 2 (13.5) | 200 | | Dispersion resin 1 (4.0) | PGMEA (82.5) |
| Pigment dispersion liquid 1-4 | IR coloring agent 1 (13.5) | — | | Dispersion resin 1 (4.0) | PGMEA (82.5) |
| Pigment dispersion liquid 1-5 | IR coloring agent 2 (13.5) | — | | Dispersion resin 1 (4.0) | PGMEA (82.5) |
| Pigment dispersion liquid 2-1 | | — | PR254 (13.5) | Dispersion resin 2 (2.0) Alkali soluble resin 1 (2.0) | PGMEA (82.5) |
| Pigment dispersion liquid 2-2 | | — | PB15:6 (13.5) | Dispersion resin 3 (4.0) | PGMEA (82.5) |
| Pigment dispersion liquid 2-3 | | — | PY139 (14.8) | Dispersion resin 1 (3.0) Alkali soluble resin 1 (2.2) | PGMEA (80.0) |
| Pigment dispersion liquid 2-4 | | — | PV23 (14.8) | Dispersion resin 1 (3.0) Alkali soluble resin 1 (2.2) | PGMEA (80.0) |
| Pigment dispersion liquid 2-5 | | — | Black material (14.8) | Dispersion resin 1 (5.2) | PGMEA (80.0) |
| Pigment dispersion liquid 2-6 | | — | PG36 (14.8) | Dispersion resin 4 (5.2) | PGMEA (80.0) |

Abbreviations of respective components in the table are as below.

[Infrared ray absorption substance] (Compound having a maximum absorption wavelength in a wavelength range of 800 to 900 nm)

Pyrrolopyrrole pigment 1: Structure below (synthesized in a method disclosed in JP2009-263614A)

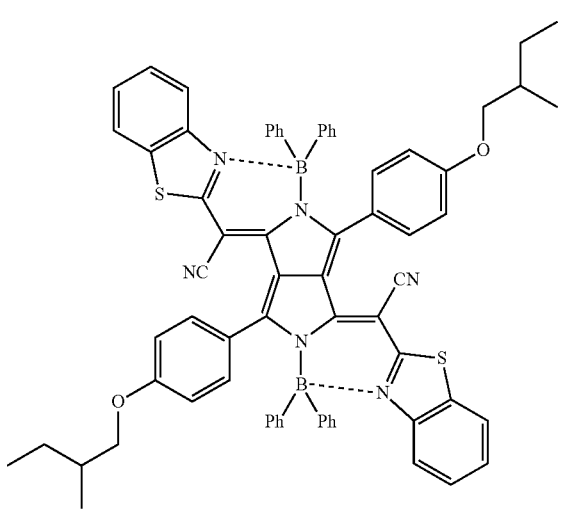

Pyrrolopyrrole pigment 2: Structure below (Synthesized by method disclosed in JP2009-263614A)

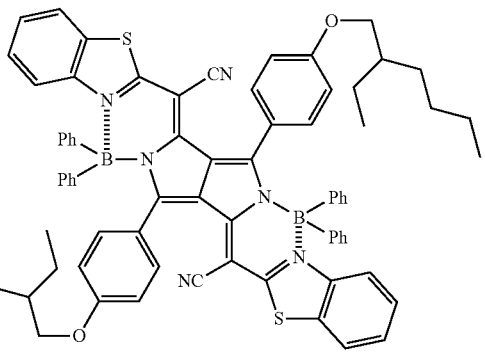

IR coloring agent 1: Product name; IRA842 (Exciton)

IR coloring agent 2: Product name; FD-25 (Yamada Kagaku Co., Ltd.)

[Coloring agent] (Compound having a maximum absorption wavelength in a wavelength range of 400 to 700 nm)

PR254: Pigment Red 254

PB15:6: Pigment Blue 15:6

PY139: Pigment Yellow 139

PV23: Pigment Violet 23

PG36: Pigment Green 36

Black material: (Irgaphoa BK (BASF))

[Resin]

Dispersion resin 1: Product name; BYK-111 (manufactured by BYK Additives & Instruments)

Dispersion resin 2: Structure below

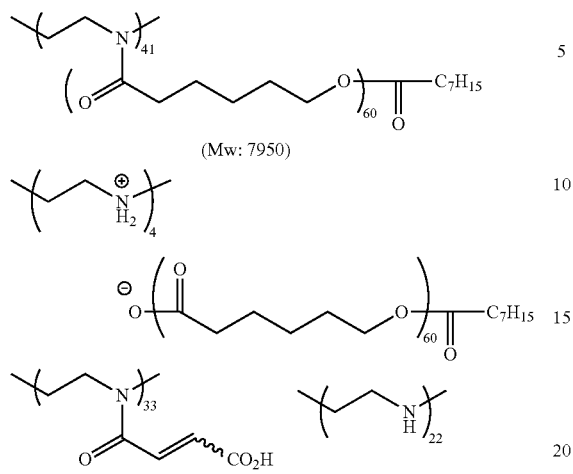

(Mw: 7950)

Dispersion resin 3: Structure below

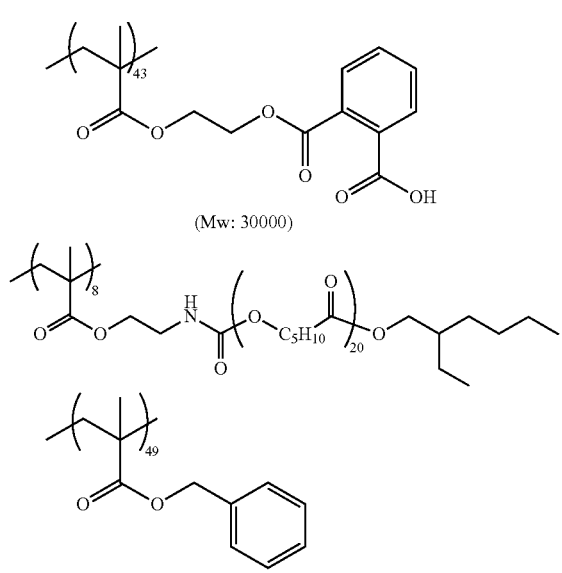

(Mw: 30000)

Dispersion resin 4: Structure below (Mw: 24,000)

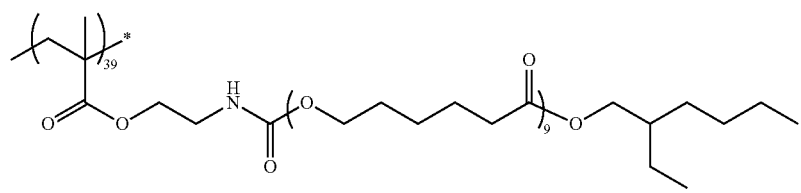

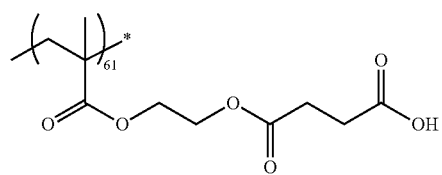

Alkali soluble resin 1: Structure below (Mw: 12,000)

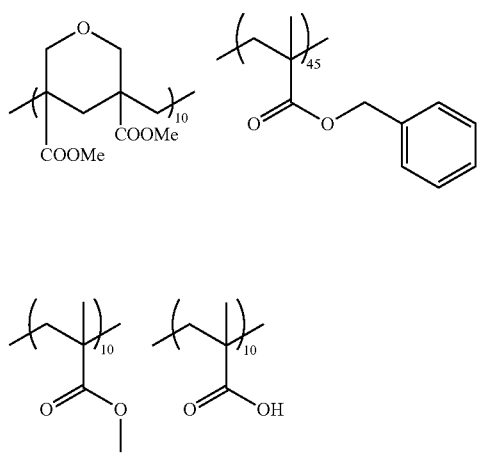

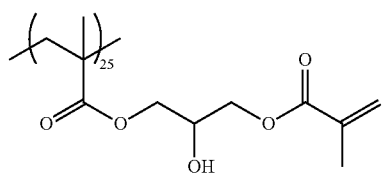

[Organic Solvent]

PGMEA: Propylene glycol methyl ether acetate

[Preparation of Coloring Composition]

Components in the table below were mixed in ratios shown in the table below, so as to prepare coloring compositions. In the table, usage amounts (Unit: parts by mass) of the corresponding components are shown.

TABLE 4

| | Manufacturing Example 1 | Manufacturing Example 2 | Manufacturing Example 3 | Manufacturing Example 4 | Manufacturing Example 5 | Manufacturing Example 6 | Manufacturing Example 7 | Manufacturing Example 8 | Manufacturing Example 9 | Manufacturing Example 10 | Manufacturing Example 11 | Manufacturing Example 12 | Manufacturing Example 13 |
|---|---|---|---|---|---|---|---|---|---|---|---|---|---|
| Pigment dispersion liquid 1-1 | 22.67 | | | | | | | | 22.67 | 22.67 | 22.67 | 22.67 | 22.67 |
| Pigment dispersion liquid 1-2 | | 22.67 | | 28.96 | | | | | | | | | |
| Pigment dispersion liquid 1-3 | | | 22.67 | | | | | | | | | | |
| Pigment dispersion liquid 1-4 | | | | | | | 22.67 | | | | | | |
| Pigment dispersion liquid 1-5 | | | | | | | | 22.67 | | | | | |
| Pyrrolopyrrole dye 1 | | | | | 3.91 | | | | | | | | |
| Pyrrolopyrrole dye 2 | | | | | | 3.91 | | | | | | | |
| Pigment dispersion liquid 2-1 | 11.33 | 11.33 | 11.33 | | 13.22 | 13.22 | 11.33 | 11.33 | | 22.67 | | 11.33 | 11.33 |
| Pigment dispersion liquid 2-2 | 22.67 | 22.67 | 22.67 | 19.14 | 19.14 | 19.14 | 22.67 | 22.67 | 22.67 | 22.67 | 11.33 | 22.67 | 22.67 |
| Pigment dispersion liquid 2-3 | 10.34 | 10.34 | 10.34 | | 5.17 | 5.17 | 10.34 | 10.34 | 17.23 | 6.89 | 10.34 | 10.34 | 10.34 |
| Pigment dispersion liquid 2-4 | 6.89 | 6.89 | 6.89 | | 4.36 | 4.36 | 6.89 | 6.89 | 10.34 | | 13.78 | 6.89 | 6.89 |
| Pigment dispersion liquid 2-5 | | | | 22.75 | | | | | | | | | |
| Pigment dispersion liquid 2-6 | | | | | | | | | | | 15.11 | | |
| Polymerizable compound 1 | 1.37 | 1.37 | 1.37 | 1.5 | 1.48 | 1.48 | 1.37 | 1.37 | 1.37 | 1.37 | 1.37 | | 1.37 |
| Polymerizable compound 2 | | | | | | | | | | | | 1.37 | |
| Alkali soluble resin 1 | 3.52 | 3.52 | 3.52 | 4.9 | 7.81 | 7.81 | 3.52 | 3.52 | 3.31 | 3.73 | 3.38 | 3.52 | 3.52 |
| Photopolymerization initiator 1 | 0.86 | 0.86 | 0.86 | 0.92 | 0.92 | 0.92 | 0.86 | 0.86 | 0.86 | 0.86 | 0.86 | 0.86 | |
| Photopolymerization initiator 2 | | | | | | | | | | | | | 0.86 |
| Surfactant 1 | 0.42 | 0.42 | 0.42 | 0.42 | 0.42 | 0.42 | 0.42 | | | | | | |
| Polymerization inhibitor 1 | 0.001 | 0.001 | 0.001 | 0.001 | 0.001 | 0.001 | 0.001 | | | | | | |
| Organic solvent 1 | 19.93 | 19.93 | 19.93 | 21.41 | 43.57 | 43.57 | 19.93 | | | | | | |
| Organic solvent 2 | | | | | | | | | | | | | |

TABLE 4-continued

| | | | | | | |
|---|---|---|---|---|---|---|
| Surfactant 1 | 0.42 | 0.42 | 0.42 | 0.42 | 0.42 | 0.42 |
| Polymerization inhibitor 1 | 0.001 | 0.001 | 0.001 | 0.001 | 0.001 | 0.001 |
| Organic solvent 1 | 19.93 | 21.13 | 18.72 | 20.74 | 19.93 | 10.93 |
| Organic solvent 2 | | | | | | 9.00 |

Abbreviations of respective components in the table are as below.

Pyrrolopyrrole dye 1: Structure below (Synthesized by the method disclosed in JP2009-263614A) (compound having a maximum absorption wavelength in a wavelength range of 800 to 900 nm)

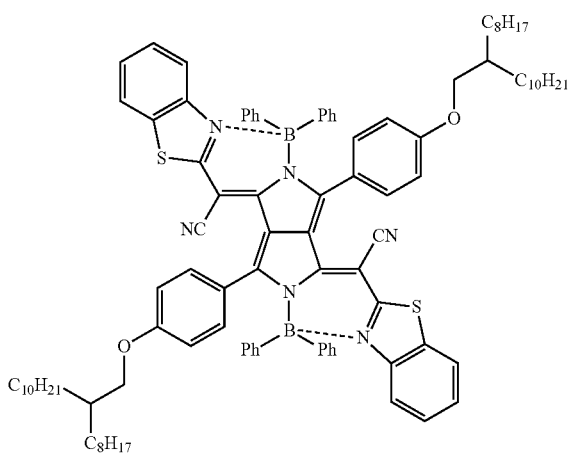

Pyrrolopyrrole dye 2: Structure below (Synthesized by the method disclosed in JP2009-263614A) (compound having a maximum absorption wavelength in a wavelength range of 800 to 900 nm

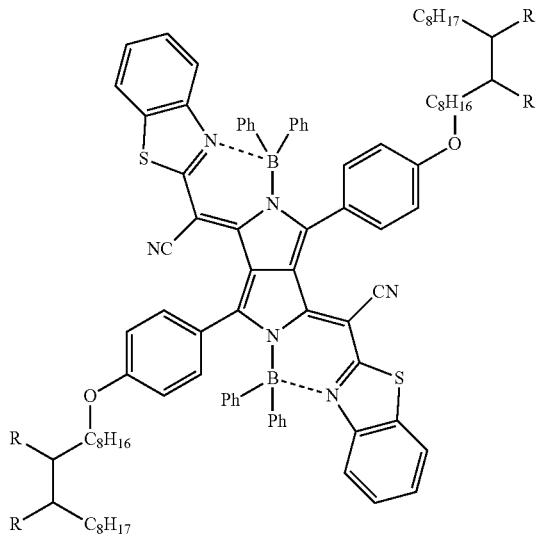

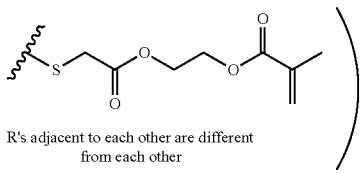

Polymerizable compound 1: M-305 (triacrylate is 55 to 63 mass %) (manufactured by Toagosei Co., Ltd.) below structure

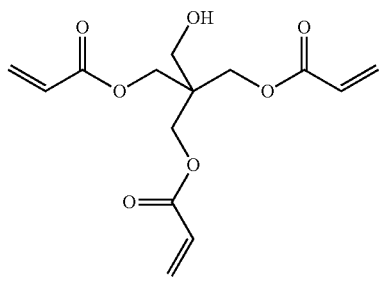

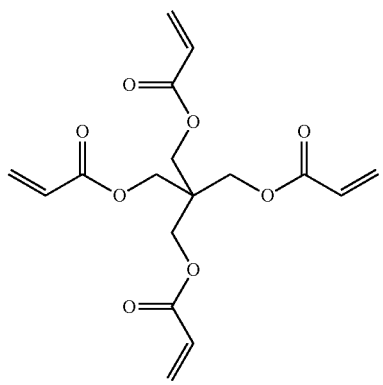

Polymerizable compound 2: Dipentaerythritol hexaacrylate (A-DPH manufactured by Shin-Nakamura Chemical Co., Ltd.)

Photopolymerization initiator 1: IRGACURE-OXE01 (manufactured by BASF SE Corp., Structure below)

Photopolymerization initiator 2: IRGACURE-OXE02 (manufactured by BASF SE Corp.)

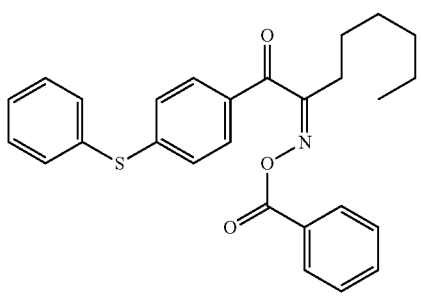 [SMILES: CCCCCC/C(=N/OC(=O)c1ccccc1)C(=O)c1ccc(Sc2ccccc2)cc1]

Surfactant 1: MEGAFACE F-781F (manufactured by DIC Corporation, fluorine-containing polymer-type surfactant)
Polymerization inhibitor 1: p-methoxyphenol
Organic solvent 1: Propylene glycol methyl ether acetate
Organic solvent 2: Cyclohexanone
Silicon wafers were coated with coloring compositions of Manufacturing Examples 1 to 13 by using a spin coater such that film thicknesses after drying were 1.0 μm, and a heating treatment (prebaking) was performed for 120 seconds by using a hot plate of 100° C.

Subsequently, a photo mask in which pixel patterns in a square shape having 1.4 μm on each side were formed by using the i-ray stepper exposure device FPA-3000i5+(manufactured by Canon Inc.) was used, an optimum exposure amount for resolving the pixel patterns in a square shape was determined by increasing from 50 to 750 mJ/cm$^2$ by 50 mJ/cm$^2$, and exposure was performed in this optimum exposure amount.

Thereafter, the silicon wafer on which the exposed coated film was formed was placed on a horizontal rotation table of a spin and shower developing machine (DW-30 type, manufactured by Chemitronics Co., Ltd.), puddle development was performed by using CD-2060 (manufactured by FUJI-FILM Electronic Materials) at 23° C. for 60 seconds, and a coloration pattern was formed on the silicon wafer.

A rinse treatment was performed with pure water on the silicon wafer on which the coloration pattern was formed, and spray drying was performed.

A heating treatment (post baking) was performed for 300 seconds by using a hot plate of 200° C., so as to form the infrared ray transmission filters 113.

Example 200

Manufacturing of Infrared Sensor

The infrared sensor illustrated in FIG. 2 was manufactured by using the near infrared ray filters of Examples 1 to 3. An object was able to be detected by using this infrared sensor.

The color filter 112 was manufactured in the same manner as the examples of JP2014-043556A. The planarizing layer 116 was manufactured in the method shown in paragraphs 0101 to 0103 of JP2014-191190A. The infrared ray transmission filters 113 were manufactured in the method shown in Example 100. The bandpass filter 120 was manufactured in the method described below.

<Preparation of Low Refractive Dispersion Liquid B-1>

According to the disclosure in paragraphs 0032 to 0034, and 0042 (Example 1-1) of JP2013-253145A, a low refractive dispersion liquid was obtained.

Rosary-shaped colloidal silica particles were included in the obtained low refractive dispersion liquid.

<Preparation of High Refractive Dispersion Liquid B-2>

The mixture liquid of the composition below was mixed and dispersed for three hours with a beads mill (a high pressure dispersing machine with pressure reducing mechanism NANO-3000-10 (manufactured by Beryu corp.)) by using zirconia beads in a diameter of 0.3 mm, so as to prepare a high refractive dispersion liquid B-2.

Titanium dioxide: 28.9 parts

Dispersion resin 1: structure below: 6.4 parts

Organic solvent (propylene glycol methyl ether acetate (PGMEA)): 64.7 parts

<Preparation of Low Refractive Composition 1>

Low refractive dispersion liquid B-1: 75.3 parts

Surfactant (10 mass % PGMEA solution of MEGAFACE F-781F (fluorine-containing polymer-type surfactant, manufactured by DIC Corporation)): 0.1 parts Organic solvent (Ethyl lactate): 24.6 parts <Preparation of High Refractive Composition 1>

High refractive dispersion liquid B-2: 84.7 parts 45 mass % PGMEA solution of alkali soluble resin 1 below: 0.9 parts Epoxy resin (EX211L manufactured by Nagase ChemteX Corporation): 2.9 parts Epoxy resin (JER157S65 manufactured by Mitsubishi Chemical Corporation): 0.7 parts Surfactant (10 mass % PGMEA solution of MEGAFACE F-781F (fluorine-containing polymer-type surfactant, manufactured by DIC Corporation): 3.4 parts Polymerization inhibitor (p-methoxyphenol): 0.002 parts Organic solvent (PGMEA): 7.4 parts Dispersion resin 1: Structure below

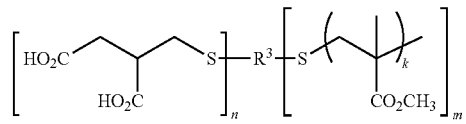

(n = 3.5, m = 2.5, k = 14)

-continued

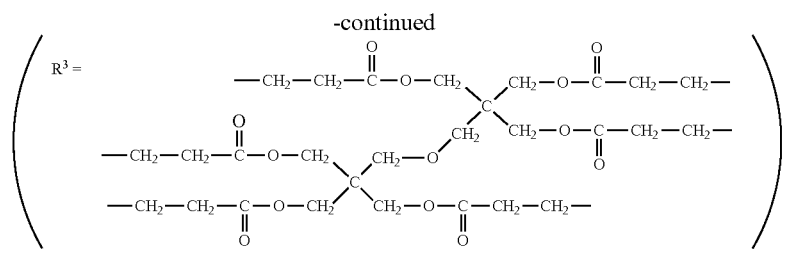

Alkali soluble resin 1: Structure below

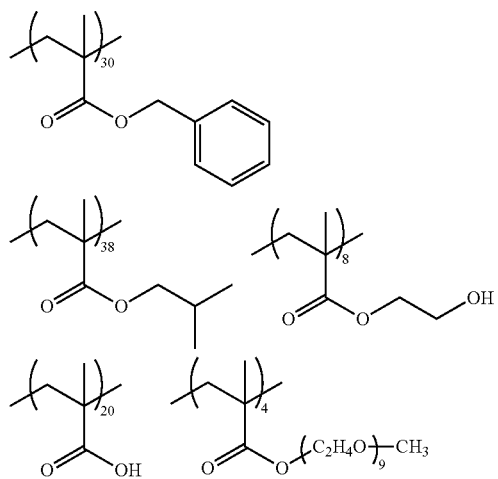

<<Measurement of Refractive Index of Composition>>

Refractive indexes of the low refractive composition and the high refractive composition were measured as below.

A glass wafer in a diameter of 200 mm was coated with a composition by a spin coating method, and heating was performed for two minutes with a hot plate of 100° C. Heating was performed with a hot plate at 200° C. for 5 minutes, so as to obtain a cured film (film thickness: 1.0 μm).

With respect to the glass wafer with a cured film obtained above, a refractive index of a transparent film to light having a wavelength of 635 nm was measured by using ellipsometry manufactured by J. A. Woollam Co., Inc.

A refractive index of a low refractive composition 1 was 1.2, and a refractive index of a high refractive composition 1 was 1.9.

<<Manufacturing of Bandpass Filter>>

The low refractive areas and the high refractive areas were alternatively laminated on the planarizing layer 116 by using the low refractive composition 1 and the high refractive composition 1, so as to have a laminate configuration shown in the table below. The low refractive composition 1 was applied by using a spin coater and dried with a hot plate at 100° C. for 120 seconds, so as to form a film. The high refractive composition 1 was applied by using a spin coater, and dried with a hot plate at 200° C. for 3 minutes, so as to form a film. Numbers in the left column of the table are laminate orders. Number 1 is on an incident side and Number 23 is on a sensor side. That is, respective layers were laminated on the planarizing layer 116 in an order from Number 23, so as to manufacture a bandpass filter.

The coating amounts and the number (laminate number) of times of coating were adjusted such that the respective thicknesses of the high refractive areas and the low refractive areas become desired thicknesses shown in the table below.

TABLE 5

|    | Bandpass filter              | Film thickness (nm) |
|----|------------------------------|---------------------|
| 1  | High refractive composition 1 | 116 |
| 2  | Low refractive composition 1  | 187 |
| 3  | High refractive composition 1 | 110 |
| 4  | Low refractive composition 1  | 55  |
| 5  | High refractive composition 1 | 17  |
| 6  | Low refractive composition 1  | 74  |
| 7  | High refractive composition 1 | 28  |
| 8  | Low refractive composition 1  | 206 |
| 9  | High refractive composition 1 | 105 |
| 10 | Low refractive composition 1  | 180 |
| 11 | High refractive composition 1 | 112 |
| 12 | Low refractive composition 1  | 187 |
| 13 | High refractive composition 1 | 215 |
| 14 | Low refractive composition 1  | 37  |
| 15 | High refractive composition 1 | 11  |
| 16 | Low refractive composition 1  | 152 |
| 17 | High refractive composition 1 | 21  |
| 18 | Low refractive composition 1  | 23  |
| 19 | High refractive composition 1 | 108 |
| 20 | Low refractive composition 1  | 22  |
| 21 | High refractive composition 1 | 27  |
| 22 | Low refractive composition 1  | 232 |
| 23 | High refractive composition 1 | 21  |

Figure 6:
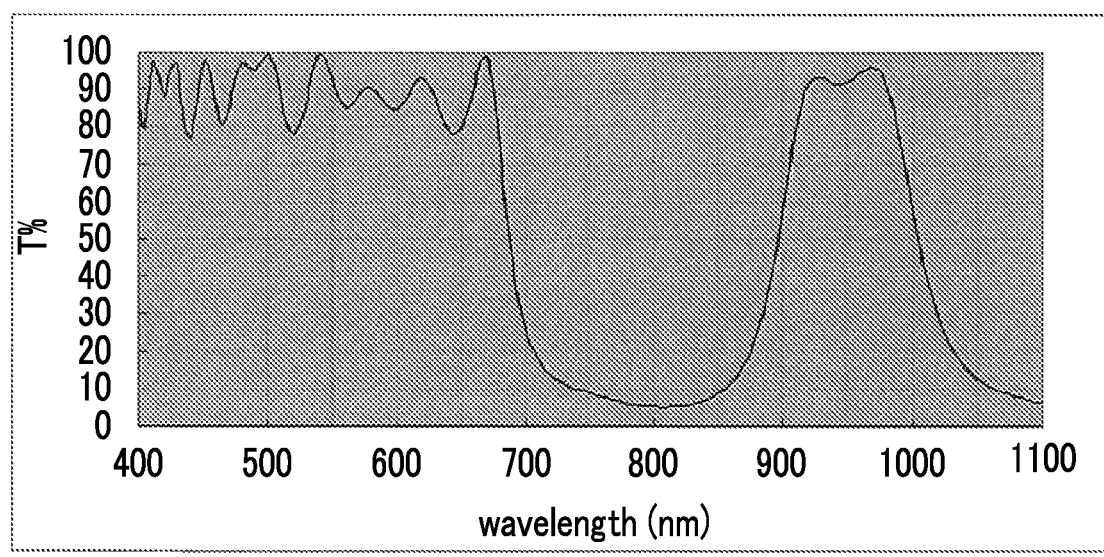
FIG. 6 is a diagram illustrating a relationship between a wavelength of a bandpass filter and a transmittance in an example.

A laminate was formed by laminating the high refractive compositions 1 and the low refractive compositions 1, so as to have the same layer configuration as the bandpass filter described above on the glass wafer in a diameter of 200 mm, such that a laminate was manufactured. With respect to the obtained laminate, transmittance in a wavelength range of 400 to 1,100 nm was measured by using a spectrophotometer (ref. glass substrate) of an ultraviolet-visible-near infrared ray spectrophotometer (U-4100 manufactured by Hitachi High-Technologies Corporation). Results thereof are shown in FIG. 6. In FIG. 6, a vertical axis indicates transmittance (Unit: %), and Wavelength on a lateral axis indicates a wavelength (Unit: nm).

EXPLANATION OF REFERENCES

1: lens optical system
10: solid-state imaging device
20: signal processing unit
30: signal switching unit
40: controller
50: signal accumulating unit
60: light emitting controller
70: infrared LED
80, 81: image output unit
100, 100a: infrared sensor
110: solid-state imaging device
111: near-infrared ray absorption filter 112: color filter
113: infrared ray transmission filter
114: area
115: microlens
116: planarizing layer
120: bandpass filter
hυ: incidence ray

What is claimed is:

1. A photosensitive resin composition comprising:
a compound represented by Formula (1) below,

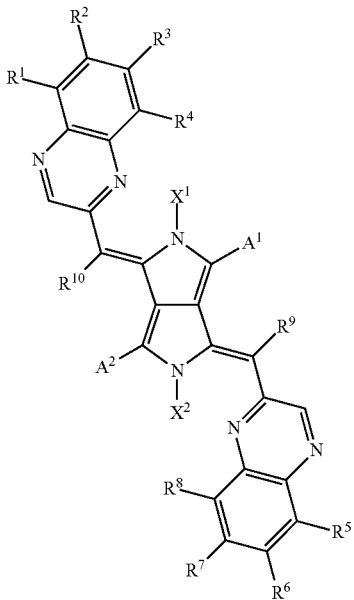

(1)

in Formula (1), $X^1$ and $X^2$ each independently represent a hydrogen atom or a substituent, $A^1$ and $A^2$ each independently represent a substituent, $R^1$ to $R^{10}$ each independently represent a hydrogen atom or a substituent, and at least one of $R^1$, $R^2$, $R^3$, $R^4$, $R^5$, $R^6$, $R^7$, and $R^8$ is a halogen atom, an alkyl group, an alkoxy group, an aryl group, a cyano group, or a group represented by -$L^{100}$-$X^{100}$, wherein $L^{100}$ represents a single bond or a divalent linking group, and $X^{100}$ represents a reactive group.

2. The photosensitive resin composition according to claim 1, further comprising:
a curable compound.

3. The photosensitive resin composition according to claim 1, wherein in Formula (1), at least one of $R^1$, $R^2$, $R^3$, $R^4$, $R^5$, $R^6$, $R^7$, and $R^8$ is a halogen atom.

4. The photosensitive resin composition according to claim 1, wherein in Formula (1), $R^9$ and $R^{10}$ are a cyano group.

5. The photosensitive resin composition according to claim 1, wherein in Formula (1), $X^1$ and $X^2$ each independently represents a group represented by Formula (2) below,

(2)

in Formula (2), $R^{21}$ and $R^{22}$ each independently represents a substituent, $R^{21}$ and $R^{22}$ may be bonded to each other to form a ring, and * represents an atomic bond.

* * * * *